(12) United States Patent
Trapp et al.

(10) Patent No.: US 8,383,098 B2
(45) Date of Patent: *Feb. 26, 2013

(54) MULTIPOTENT NEURAL STEM CELLS

(75) Inventors: Bruce Trapp, Bentleyville, OH (US); Robert Miller, Cleveland Heights, OH (US)

(73) Assignee: Case Western REserve University, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 12/871,743

(22) Filed: Aug. 30, 2010

(65) Prior Publication Data

US 2012/0045832 A1 Feb. 23, 2012

Related U.S. Application Data

(62) Division of application No. 11/601,565, filed on Nov. 17, 2006, now Pat. No. 7,803,364.

(60) Provisional application No. 60/738,119, filed on Nov. 17, 2005.

(51) Int. Cl.
*A61K 35/30* (2006.01)
*C12N 5/00* (2006.01)
*A61K 35/00* (2006.01)

(52) U.S. Cl. ....... 424/93.6; 424/93.1; 424/570; 435/325

(58) Field of Classification Search .................. None
See application file for complete search history.

(56) References Cited

U.S. PATENT DOCUMENTS

| | | |
|---|---|---|
| 6,795,776 B1 | 9/2004 | Weinmann et al. |
| 6,830,927 B2 | 12/2004 | Rao et al. |
| 6,890,724 B2 | 5/2005 | Anderson et al. |
| 7,217,565 B2 | 5/2007 | Buck et al. |
| 7,803,364 B2 * | 9/2010 | Trapp et al. .................. 424/93.6 |
| 2002/0164309 A1 | 11/2002 | Carpenter |
| 2004/0028685 A1 | 2/2004 | Kinch et al. |
| 2004/0092010 A1 | 5/2004 | Ruiz I Altaba et al. |
| 2005/0221479 A1 | 10/2005 | Nakayama et al. |
| 2005/0226852 A1 | 10/2005 | Toda et al. |

FOREIGN PATENT DOCUMENTS

WO WO 2004/020597 A2 3/2004

OTHER PUBLICATIONS

Cattaneou et al., "Non-Virally Mediated Gene Transfer into Human Central Nervous System Precursor Cells", Molecular Brain Research, 1996; 42:161-166.

Doetsch, et al., "Regeneration of a Germinal Layer in the Adult Mammalian Brain", Proc. Natl. Acad. Sci., 1999;96:11619-11624.
Doetsch, et al., "Egf Converts Transit-Amplifying Neurogenic Precursors in the Adult Brain Into Multipotent Stem Cells", Neuron, vol. 36, 1021-1034, Dec. 19, 2002.
Fargeas, Christine, et al., "AC133 Antigen, CD133, Prominin-1, Prominin-2, Etc.: Prominin Family Gene Products in Need of a Rational Nomenclature", Stem Cells 2003;21:506-508.
Fargeas, Christine, et al., "Characterization of Prominon-2, a New Member of the Prominin Family of Pentaspan Membrane Glycoproteins", The Journal of Biological Chemistry, vol. 278, No. 10, Issue of Mar. 7, pp. 8586-8596, 2003.
Fargeas, Christine, et al., "Nomenclature of prominin-1 (CD133) Splic variants—an update", Tissue Antigen 69, 602-606, 2007.
Galli et al., "Regulation of Neuronal Differentiation in Human CNS Stem Cell Progeny by Leukemia Inhibitor Factor", Dev. Neurosci., 2000;22:86-95.
Galli, et al., "Neural Stem Cells, an Overview", Circulation Research, 2003;93:598-608.
La Russa, Vincent F. et al., "Cancer Investigation", Stem Cells 21:437-448, 2003.
McKusick, Victor A., "Prominin, Mouse, Homolog-Like1 ; PromL1, AC133, CD133, Antigen; CD133", Created Dec. 22, 1999, retrieved from http://omim.org/entry/604365.
Melanson-Drapeau, Lysanne, et al., "Oligodendrocyte Progenitor Enrichment in the Connexin32 Null-Mutant Mouse", The Journal of Neuroscience, Mar. 1, 2003, 23(5):1759-1768.
Miller, Leigh-Anne D., "Role of Sonic Hedgehog in Patterning of Tracheal-Bronchial Cartilage and the Peripheral Lung", Developmental Dynamics 231:57-71, 2004.
Munoz-Elias, Guillermo, et al., "Marrow Stromal Cells, Mitosis, and Neuronal Differentiation: Stem Cell and Precursor Functions", Stem Cells 2003;21:437-448.
Shmelkov, Sergey, V., "AC133/CD133/Prominin-1", The International Journal of Biochemistry & Cell Biology, vol. 37, Issue 4, Apr. 2005, pp. 715-716.
Terada et al., "Beta IV Tubulin is Selectively Expressed by Oligodendrocytes in the Central Nervous System", Glia, 2005;50:212-222.
Vescovi et al., "Isolation and Intracerebral Grafting of Nontransformed Multipotent Embryonic Human CNS Stem Cells", Journal of Neurotrauma, 1999;16:689-693.
Wu, Chaunshen, et al., "β4 Tubulin Identified a Primitive Cell Source for Oligodendrocytes in the Mammalian Brain", The Journal of Neuroscience, Jun. 17, 2009, 29(24):7649-7657.
Zhou et al., "The bHLH Transcription Factors OLIG2 and OLIG1 Couple Neuronal and Glial Subtype Specification", Cell, vol. 109, 61-73, Apr. 5, 2002.

* cited by examiner

*Primary Examiner* — Doug Schultz
(74) *Attorney, Agent, or Firm* — Tarolli, Sundheim, Covell & Tummino LLP

(57) ABSTRACT

An isolated multipotent neural stem cells has a phenotype identified by expression of the protein β-tubulin IV and Olig2 and the absence of the proteins NG2, PLP, and GFAP.

9 Claims, 14 Drawing Sheets

SEQUENCE LISTING

<160> NUMBER OF SEQ ID NOS: 16

<210> SEQ ID NO 1
<211> LENGTH: 20
<212> TYPE: PRT
<213> ORGANISM: Rattus norvegicus

<400> SEQUENCE: 1

Thr Thr Leu Tyr Glu Lys Phe Thr Tyr Ala Gly Ile Asp Cys Ser Ala
1               5                   10                  15

Glu Glu Ala Ala
            20

<210> SEQ ID NO 2
<211> LENGTH: 10
<212> TYPE: PRT

<213> ORGANISM: Rattus norvegicus

<400> SEQUENCE: 2

Thr Ala Val Cys Asp Ile Pro Pro Glu Arg
1               5                   10

<210> SEQ ID NO 3
<211> LENGTH: 9
<212> TYPE: PRT
<213> ORGANISM: Rattus norvegicus

<400> SEQUENCE: 3

Tyr Leu Thr Val Ala Ala Val Phe Arg
1               5

<210> SEQ ID NO 4
<211> LENGTH: 9
<212> TYPE: PRT
<213> ORGANISM: Rattus norvegicus

<400> SEQUENCE: 4

Tyr Leu Thr Val Ala Ala Ile Phe Arg
1               5

<210> SEQ ID NO 5
<211> LENGTH: 10
<212> TYPE: PRT
<213> ORGANISM: Rattus norvegicus

<400> SEQUENCE: 5

Phe Pro Gly Gln Leu Asn Ala Asp Leu Arg
1               5                   10

<210> SEQ ID NO 6
<211> LENGTH: 10
<212> TYPE: PRT
<213> ORGANISM: Rattus norvegicus

<400> SEQUENCE: 6

Leu Ala Val Asn Met Val Pro Phe Pro Arg
1               5                   10

<210> SEQ ID NO 7
<211> LENGTH: 10
<212> TYPE: PRT
<213> ORGANISM: Rattus norvegicus

<400> SEQUENCE: 7

Ile Ser Glu Gln Phe Thr Ala Met Phe Arg
1               5                   10

<210> SEQ ID NO 8
<211> LENGTH: 11
<212> TYPE: PRT
<213> ORGANISM: Rattus norvegicus

<400> SEQUENCE: 8

Lys Leu Ala Val Met Asn Val Pro Phe Pro Arg
1               5                   10

<210> SEQ ID NO 9
<211> LENGTH: 12
<212> TYPE: PRT
<213> ORGANISM: Rattus norvegicus

<400> SEQUENCE: 9

Ile Met Asn Thr Phe Ser Val Met Pro Ser Pro Lys
1               5                   10

<210> SEQ ID NO 10
<211> LENGTH: 15
<212> TYPE: PRT
<213> ORGANISM: Rattus norvegicus

<400> SEQUENCE: 10

Ala Val Leu Val Asp Leu Glu Pro Gly Thr Met Asp Ser Val Arg
1               5                   10                  15

<210> SEQ ID NO 11
<211> LENGTH: 14
<212> TYPE: PRT
<213> ORGANISM: Rattus norvegicus

<400> SEQUENCE: 11

Leu His Phe Phe Met Pro Gly Phe Ala Pro Leu Thr Ser Arg
1               5                   10

<210> SEQ ID NO 12
<211> LENGTH: 15
<212> TYPE: PRT
<213> ORGANISM: Rattus norvegicus

<400> SEQUENCE: 12

Ala Ile Leu Val Asp Leu Glu Pro Gly Thr Met Asp Ser Val Arg
1               5                   10                  15

<210> SEQ ID NO 13
<211> LENGTH: 15
<212> TYPE: PRT
<213> ORGANISM: Rattus norvegicus

<400> SEQUENCE: 13

Ala Ile Leu Val Asp Leu Glu Pro Gly Thr Met Asp Ser Val Arg
1               5                   10                  15

<210> SEQ ID NO 14
<211> LENGTH: 14
<212> TYPE: PRT
<213> ORGANISM: Rattus norvegicus

<400> SEQUENCE: 14

Asn Ser Ser Tyr Phe Val Glu Trp Ile Pro Asp Asn Val Lys
1               5                   10

<210> SEQ ID NO 15
<211> LENGTH: 15
<212> TYPE: PRT
<213> ORGANISM: Rattus norvegicus

<400> SEQUENCE: 15

Ala Leu Thr Val Pro Glu Leu Thr Gln Gln Met Phe Asp Ser Lys
1               5                   10                  15

<210> SEQ ID NO 16
<211> LENGTH: 21
<212> TYPE: PRT
<213> ORGANISM: Rattus norvegicus -continued

```
<400> SEQUENCE: 16

Met Glu Val Gly Trp Tyr Arg Ser Pro Phe Ser Arg Val Val His Leu
1               5                   10                  15

Tyr Arg Asn Gly Lys
            20
```

US 8,383,098 B2

MULTIPOTENT NEURAL STEM CELLS

RELATED APPLICATION

The present application is a divisional of U.S. patent application Ser. No. 11/601,565, filed Nov. 17, 2006 now U.S. Pat. No. 7,803,364, which claims priority from U.S. Provisional Patent Application Ser. No. 60/738,119 filed Nov. 17, 2005, which is herein incorporated by reference in its entirety.

The work described in this application was supported, at least in part, by NIH Grant No. R01 NS029818. The United States government may have certain rights in this invention.

TECHNICAL FIELD

The present invention is directed to isolated and purified neural stem cells, and to methods of detecting, enriching, and culturally expanding neural stem cells.

BACKGROUND OF THE INVENTION

A number of conditions and diseases of the central (brain and spinal cord) and peripheral nervous system adversely affect humans. These conditions and diseases include, for example, spinal cord injury, amyotrophic lateral sclerosis (ALS), Parkinson's disease, stroke, traumatic brain injury, brain tumors, multiple sclerosis (MS), and Fabry Disease. Clinical management strategies frequently focus on the prevention of further neurological damage or injury rather than replacement or repair of the damaged neurological tissue (e.g., neurons, glial cells). These strategies can include treatment with exogenous steroids and synthetic, non-cellular pharmaceutical drugs and can have varying degrees of success, which may depend on the continued administration of the steroid or synthetic drug.

For this reason, there is a great deal of evolving interest in neural progenitor cells. Up until the present time, it was generally thought that multipotent neural progenitor cells commit early in the differentiation pathway to either neural restricted cells or glial restricted cells. These in turn are thought to give rise to mature neurons, or to mature astrocytes and oligodendrocytes. Multipotent neural progenitor cells in the neural crest also differentiate to neurons, smooth muscle, and Schwann cells. It is hypothesized that various lineage-restricted precursor cells renew themselves and reside in selected sites of the central nervous system, such as the spinal chord. Cell lineage in the developing neural tube has been reviewed in the research literature by Kalyani et al. (Biochem. Cell Biol. 6:1051, 1998).

Putative multipotent neuroepithelial cells (NEP cells) have been identified in the developing spinal cord. Kalyani et al. (Dev. Biol. 186:202, 1997) reported NEP cells in the rat. Mujtaba et al. (Dev. Biol. 214:113, 1999) reported NEP cells in the mouse. Differentiation of NEP cells is thought to result in formation of restricted precursor cells having characteristic surface markers.

Putative neural restricted precursors (NRP) were characterized by Mayer-Proschel et al. (Neuron 19:773, 1997). These cells express cell-surface PS-NCAM, a polysialylated isoform of the neural cell adhesion molecule. They reportedly have the capacity to generate various types of neurons, but do not form glial cells.

Putative glial restricted precursors (GRPs) were identified by Rao et al. (Dev. Biol. 188: 48, 1997). These cells apparently have the capacity to form glial cells but not neurons.

Ling et al. (Exp. Neurol. 149:411, 1998) isolated progenitor cells from the germinal region of rat fetal mesencephalon. The cells were grown in EGF, and plated on poly-lysine coated plates, whereupon they formed neurons and glia, with occasional tyrosine hydroxylase positive (dopaminergic) cells, enhanced by including IL-1, IL-11, LIF, and GDNF in the culture medium.

Wagner et al. (Nature Biotechnol. 17:653, 1999) reported cells with a ventral mesencephalic dopaminergic phenotype induced from an immortalized multipotent neural stem cell line. The cells were transfected with a Nurr1 expression vector, and then cocultured with VM type 1 astrocytes. Over 80% of the cells obtained were claimed to have a phenotype resembling endogenous dopaminergic neurons.

Mujtaba et al. (supra) reported isolation of NRP and GRP cells from mouse embryonic stem (mES) cells. The NRPB were PS-NCAM immunoreactive, underwent self-renewal in defined medium, and differentiated into multiple neuronal phenotypes. They apparently did not form glial cells. The GRPs were A2B5-immunoreactive, and reportedly differentiated into astrocytes and oligodendrocytes, but not neurons.

SUMMARY OF THE INVENTION

The present invention relates to isolated multipotent neural stem cells (i.e., βT4 cells) and to the use of isolated multipotent neural stem cells in therapeutic applications and as a research tool. The isolated multipotent neural stem cells are identified by the expression of the protein β-tubulin IV (βT4) and Olig2 and the absence of the proteins neural/glial cell 2 (NG2), proteolipid protein (PLP), and glial fibrillary acidic protein (GFAP). The multipotent neural stem cells are also capable of differentiating into neural cells of more than one lineage.

Another aspect of the present invention includes a method of detecting a multipotent neural stem cell from central nervous system (CNS) tissue. CNS tissue is harvested from a human subject and then contacted with at least one antibody that binds to βT4, at least one antibody that binds to NG2, at least one antibody that binds to PLP, and at least one antibody that binds to Olig2 and/or an antibody that binds to GFAP. Next, neural stem cells which positively bind the at least one βT4 antibody and Olig2, and which do not bind the at least one NG2 antibody, the at least one PLP antibody, and the at least one GFAP antibody is identified.

In a further aspect of the present invention, a method is provided for enriching a population of neural stem cells. A population of uncultured neural cells containing at least one neural stem cell that expresses βT4 and Olig2 and does not express NG2, PLP and GFAP, is obtained. The cells are then formed into primary neurospheres by placing them in a neurosphere forming medium. Cells of the neurospheres are then contacted with reagent that kills actively dividing cells. The remaining cells are then formed into secondary neurospheres.

Yet another aspect of the present invention provides a method for the in vitro differentiation of a neural stem cell into a neural cell. A population of neural stem cells that express βT4 and Olig2 and that do not express NG2, PLP and GFAP is first selected. Then, at least one proliferation-inducing growth factor is administered to the cells. The proliferation-inducing growth factor is capable of inducing the proliferation of the population into at least one neural cell, such as a neuron, astrocyte or oligodendrocyte.

A further aspect of invention relates to a therapeutic application for treating a central nervous system disorder. The therapeutic application includes administering to a subject having the central nervous system disorder a quantity of multipotent neural stem cells. The multipotent neural stem cells are identified by the expression of the protein β-tubulin IV (βT4) and Olig2 and the absence of the proteins neural/glial cell 2 (NG2), proteolipid protein (PLP), and glial fibrillary acidic protein (GFAP).

Yet another application relates to an assay system for screening of potential agents (e.g., small molecules, proteins, peptides, nucleic acids, etc.) effective to modulate the proliferation, differentiation, and/or expression of multipotent neural stem cells. The assay system can be adapted to identify agents that are capable of modulating the multipotent neural stem cell, either in vitro or in vivo. In the assay system, multipotent neural stem cells that express βT4 and Olig2 and do not express NG2, PLP and GFAP, are cultured with an agent that is being tested. The effect of the agent on the multipotent neural stem cells is then determined.

A further aspect of the invention relates to a method of detecting the presence or activity of an agent, which modulates the proliferation, differentiation, and/or expression of multipotent neural stem cells. In the method, multipotent neural stem cells that express βT4 and Olig2 and do not express NG2, PLP and GFAP, are contacted with a sample that includes an agent suspected of modulating the proliferation, differentiation, and/or expression of multipotent neural stem cells. The effect of the sample is then determined, for example, by morphology, mRNA expression, and antigen or protein expression.

Yet a further aspect of the invention relates to a method of testing the ability of an agent to modulate the proliferation, differentiation, and/or expression of multipotent neural stem cells. In the method, multipotent neural stem cells that express βT4 and Olig2 and do not express NG2, PLP and GFAP, are contacted with an agent under test. The effect of the agent is then determined, for example, by morphology, mRNA expression, and antigen or protein expression.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 6D, MS from box in FIG. 6B). Some subventricular βT4 cells have a bipolar morphology with oval cell bodies (FIG. 6E, arrows); other non-bipolar βT4 cells often have round cell bodies with several fine processes. βT4 cells tend to appear in clusters (FIG. 6F, arrows) or doublets (FIG. 6F, arrowheads) and appear to be increased in MS lesions (FIGS. 6D-F), when compared to control (FIG. 6C). Note that the SVZ in MS lesions is wider (FIG. 6D) than the SVZ of control brain (FIG. 6C). Weaker βIV tubulin staining is also found on oligodendrocytes in myelinated white matter (FIG. 6C, arrowheads).

FIG. 8F) aspects of the lateral ventricle, but very few in the germinal matrix zone (FIGS. 8B-C and Fig. E). rβT4 cells are rare in the superior aspect of the lateral ventricle (FIG. 8B). By 17 months of age (FIG. 8H, frontal horn), βT4 cells can be detected in the SVZ throughout the lateral ventricle.

DETAILED DESCRIPTION

Figure 1:
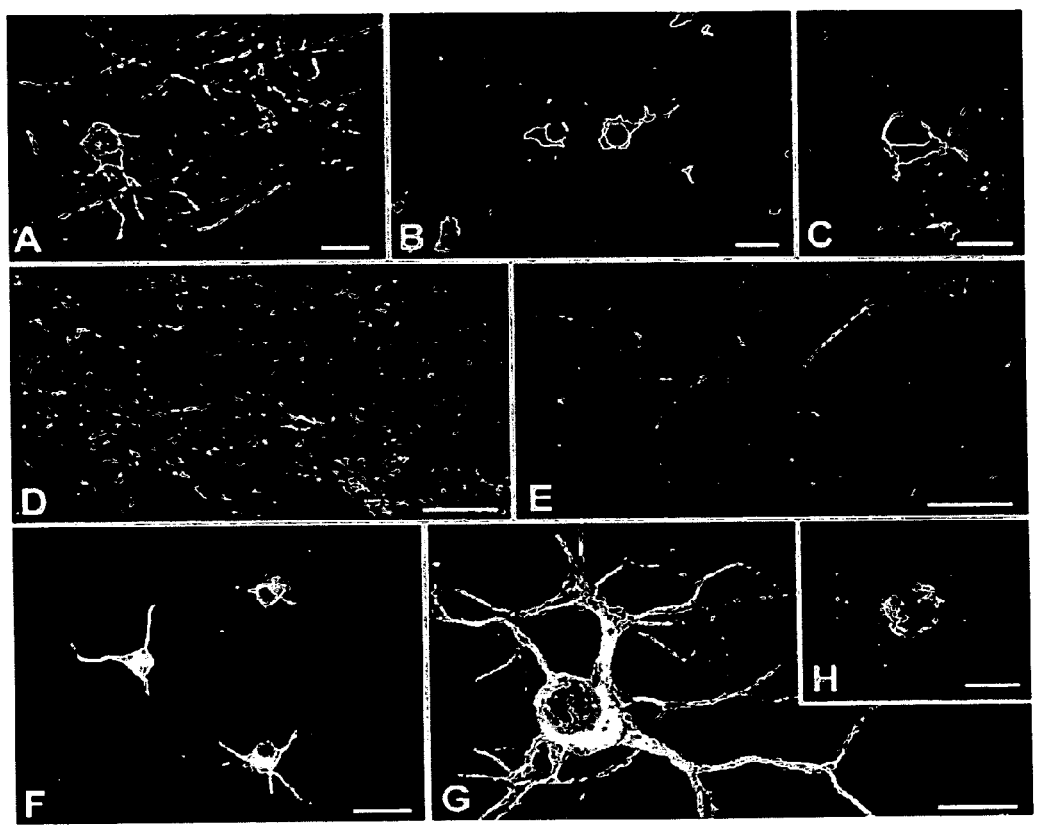
FIG. 1 illustrates Tie-2 C-terminal antibodies label oligodendrocytes in P10 rat brain sections and mixed glial cultures. Double-labeling for Tie-2 and oligodendrocyte markers CNP (A) CC 1 (B) and PLP/DM 20 (C) indicated that oligodendrocytes were labeled by Tie-2 C-terminal antibodies. Some cells had numerous short PLP/DM20-labeled processes (C), which identified them as premyelinating oligodendrocytes. Oligodendrocyte progenitor cells labeled for NG2 (D) and astrocytes labeled for GFAP (E) did not express detectable Tie-2 staining. In mixed glial cultures after 5 days in culture, Tie-2 C-terminal immunoreactivity labeled the oligodendrocyte cell body and processes (F), which at higher magnification (G) had a filamentous appearance characteristic of cytoskeletal staining. Tie-2 C-terminal antibodies also labeled the mitotic spindles of cells in these cultures (H), suggesting that a MT-related structure was stained. All images are confocal micrographs from z-series projections of 5-10 optical slices. Scale bars=10 μm in A-C, G; 25 μm in D-F; 5 μm in H.

The present invention is directed to isolated and purified human multipotent neural stem cells, to a method of detecting, enriching, and culturally expanding multipotent neural stem cells, and to characterization of and uses for such cells.

The multipotent neural stem cell is an undifferentiated neural cell that can be induced to proliferate using the methods of the present invention. The neural stem cell is capable of self-maintenance, meaning that with each cell division, one daughter cell will also be a stem cell. The non-stem cell progeny of a neural stem cell are termed progenitor cells. The progenitor cells generated from a single multipotent neural stem cell are capable of differentiating, for example, into neurons, astrocytes and oligodendrocytes. Hence, the neural stem cell is "multipotent" because its progeny have multiple differentiative pathways.

Multipotent neural stem cells of the present can be characterized by a particular phenotype, i.e., a particular protein expression pattern. More particularly, the multipotent neural stem cells may be identified by expression of the β-tubulin TV (βT4) protein and the neural basic helix-loop-helix (bHLH) transcription factor Oligodendrocyte 2 (Olig2) and the absence of proteins neural/glial cell 2 (NG2), proteolipid protein (PLP), and glial fibrillary acidic protein (GFAP). Additionally, the multipotent neural stem cells (i.e., βT4 cells) may be characterized by a low rate of cellular division and resistance to the antimetabolic effects or antimitotic effect of antimetabolic agents or antimitotic agents, such as cytosine-β-D-arabinofuranoside (Ara-C). The βT4 cells may be located in, and isolated, for example, from a particular brain region, such as the subventricular zone (SVZ) of the telencephalon.

The neural tissue from which the βT4 cells of the present invention can be obtained include any animal that has neural tissue, such as birds, amphibians, mammals and the like. In an aspect of the invention the source of neural tissue can be from mammals, such as mice and humans.

Brain regions of particular interest include any area from which neural stem cells can be obtained. Areas of the brain can include the cerebral cortex, hippocampus, cerebellum, midbrain, brainstem, spinal cord and ventricular tissue. For example, areas of the brain can include regions in the basal ganglia, preferably the striatum, which consists of the caudate and putamen, or various cell groups, such as the globus pallidus, the subthalamic nucleus, the nucleus basalis, or the substantia nigra pars compacta. In one example, the neural tissue is obtained from ventricular tissue, such as the subventricular zone (SVZ), that is found lining CNS ventricles and also includes the subependyma. The term "ventricle" refers to any cavity or passageway within the CNS through which cerebral spinal fluid flows. Thus, the term not only encompasses the lateral, third, and fourth ventricles, but also encompasses the central canal, cerebral aqueduct, and other CNS cavities.

The multipotent neural stem cells of the present invention may also be derived from fetal tissue, for example, following elective abortion, or from a post-natal, juvenile or adult organ donor. Neural tissue can be obtained by biopsy, or from patients undergoing neurosurgery in which neural tissue is removed, for example, during epilepsy surgery, temporal lobectomies and hippocampalectomies.

Another aspect of the invention relates to a method of detecting a multipotent neural stem cell (i.e., βT4 cell) from CNS tissue. CNS tissue may be harvested from a mammal, such as a human, and then contacted with at least one antibody capable of binding to βT4; at least one antibody that binds to NG2; at least one antibody that binds to PLP; and at least one antibody that binds to GFAP or Olig2. Neural stem cells which positively bind to the at least one βT4 antibody and Olig2 antibody, and which do not bind the at least one NG2 antibody, the at least one PLP antibody, and the at least one GFAP antibody, may be identified.

This aspect of the present invention relies upon isolating a particular cell type from the CNS tissue. The person skilled in the art would readily understand that this may be achieved in various ways. For example, cells from the neural tissue can be dissected from the SVZ and subsequently processed to isolate neural stem cells therefrom. Neural tissue from the SVZ may also be selectively dissociated and neural stem cells isolated or recovered therefrom.

Optionally, neural stem cells may be selectively isolated from a CNS tissue preparation that comprises heterogeneous tissue types. For example, a larger region of brain tissue, which may contain tissues other than the SVZ cell layer, may be dissected and neural stem cells selectively isolated therefrom by, for example, recovering only cells having the phenotype of the neural cells of the present invention. As will be discussed in more detail below, this may be achieved by, for example, using affinity separation techniques with affinity reagents having specificity for cell surface markers specific for neural stem cells.

In an aspect of the invention, neural stem cells (i.e., βT4 cells) may be dissociated, preferably to single cells, and then separated. The neural stem cells can be obtained from the neural tissue and screened for cells exhibiting at least one characteristic or trait of a neural stem cell. For example, CNS tissue may be collected from the SVZ of a human or animal brain. Such a dissection and recovery of tissue is easily performed by the skilled artisan in this field by any suitable routine method. The dissociation step may be performed by any suitable method, such as an enzymatic and/or mechanical treatment, and is not restricted in any way as long as the desired single cells are obtained as a result thereof. Examples of such methods include, e.g., trituration, trypsin treatment, collagenase treatment and hyaluronidase treatment. By way of example, the dissociation may be performed by enzymatic treatment with trypsin. The dissociation of tissue may alternatively be performed by any other method easily chosen by the skilled artisan in view of the prevailing conditions.

The screening or detecting of the resulting cells, such as single cells, may be performed by any suitable method depending on the characteristic, trait or property of the neural stem cell. For example, the screening or detection may be performed by use of the expression of a specific cell surface marker, such as a protein. Such expression may include the expression of βT4 and Olig2. Additionally, neural stem cells may be screened or detected by the expression or, more accurately, the lack thereof, of a particular protein or proteins. For instance, cells may be screened for the presence of NG2, PLP and GFAP. Thus, neural stem cells of the present invention may be identified or detected where the screened cells do not express NG2, PLP and GFAP and, rather, express at least one βT4 protein.

By way of example, βT4 cells in the SVZ of rat brain were identified using two different antibodies to the C-terminal portion of Tie 2, the receptor for angiopoetin. The cells were negative for GFAP and Iba, markers for astrocytes and microglia. SVZ βT4 cells were, however, positive for Olig2, a b-HLH transcription factor expressed by SVZ cells that can give rise to oligodendrocyte progenitor cells.

βT4 cells were also identified in fetal human brains with βIV tubulin antibodies. It is believed that βT4 cells are related to the second wave of gliogenesis that occurs during late fetal and early postnatal periods in rodents. Fetal SVZ βT4 cells were negative for GFAP, Iba, NG2 and PLP indicating that they do not express astrocytic, microglial, OPC or oligodendrocyte markers. The lack of GFAP also suggests that βT4 cells differ from multipotent stem cells identified previously. In addition to these glial cell markers, fetal human βT4 cells were negative for the immature neuronal marker Tuj-1 (neuron specific class III β-tubulin), neuronal nuclei (NeuN) and polysialyated neural cell adhesion molecule (PSA-NCAM) PSA-NCAM antibodies stained the majority of cells in the major germinal matrix zone, dissociating PSA-NCAM cells and βT4 cells at this location.

A further aspect of the invention relates to a method of forming a substantially homogenous enriched population of neural stem cells. In the method, a population of uncultured cells containing at least one neural stem cell that expresses βT4 and Olig2, and that does not express NG2, PLP and GFAP is obtained from neural tissue. Cells can be obtained from donor tissue by dissociation of individual cells from the connecting extracellular matrix of the tissue. For example, tissue from a particular neural region may be removed from the brain using a sterile procedure, and the cells dissociated using any method known in the art including treatment with enzymes such as trypsin, collagenase and the like, or by using physical methods of dissociation such as with a blunt instrument. In an aspect of the invention, dissociation of fetal cells can be carried out in tissue culture medium, while dissociation of juvenile and adult cells can be carried out in low $Ca^{2+}$ artificial cerebral spinal fluid (aCSF). Dissociated cells may be centrifuged at low speed, between 200 and 2000 rpm, usually between 400 and 800 rpm, and then re-suspended in culture medium. The neural stem cells (i.e., rβT4 cells) can then be cultured in suspension or on a fixed substrate. Cell suspensions may then be seeded in any receptacle capable of sustaining cells, particularly culture flask, culture plates or roller bottles, and more particularly in small culture flasks such as 25 $cm^2$ culture flasks. Cells cultured in suspension may then be re-suspended at a desired concentration.

The dissociated neural stem cells are then formed into neurospheres by placing the dissociated cells into any known culture medium that is capable of promoting formation of neurospheres. Such culture medium can include, for example, HEM, DMEM, RPMI, F-12, and combinations thereof. The culture medium can include supplements which are required for cellular metabolism, such as glutamine and other amino acids, vitamins, minerals and useful proteins, such as transferrin and the like. The culture medium may also contain antibiotics to prevent contamination with yeast, bacteria and fungi such as penicillin, streptomycin, gentamicin and the like. In some cases, the medium may contain serum derived from bovine, equine, chicken and the like. However, a medium for promotion of the formation of neurospheres is typically serum-free culture, as serum tends to induce differentiation and contains unknown components (i.e., is undefined). A defined culture medium can also be used if the cells are to be used for transplantation purposes. For example, the culture medium can comprise a mixture of DMEM, F12, and a defined hormone and salt mixture.

Conditions for culturing can be close to physiological conditions. The pH of the culture medium should be close to physiological pH, preferably between a pH of about 6 and about 8, for example, a pH of about 7 to about 7.8, or a pH of about 7.4. Physiological temperatures can range between about 30° C. to about 40° C. Cells can be cultured at temperatures between about 32° C. and about 38° C., for example between about 35° C. and about 37° C.

The culture medium can be supplemented with at least one neurosphere inducing growth factor and/or compound. As used herein, the term "growth factor" refers to a protein, peptide or other molecule or compound having a growth, proliferative, differentiative, or trophic effect on neural stem cells and/or neural stem cell progeny. Examples of growth factors can include, for example, bone morphogenetic proteins (BMPs), platelet-derived growth factor (PDGF), Sonic hedgehog (Shh), insulin-like growth factor 1 (IGF-1), epidermal growth factor (EGF), amphiregulin, acidic fibroblast growth factor (aFGF or FGF-1), basic fibroblast growth factor (bFGF or FGF-2), transforming growth factor alpha (TGFα), nerve growth factor (NGF), N2 (Invitrogen), thyrotropin releasing hormone (TRH), transforming growth factor betas (TGFβs), and combinations thereof. In one aspect of the growth factors included in the culture medium can include EGF and FGF.

Growth factors are usually added to the culture medium at concentrations ranging between about 1 fg/ml to about 1 mg/ml. Concentrations between about 1 ng/ml to about 100 ng/ml are usually sufficient. Simple titration experiments can easily be performed to determine the optimal concentration of a particular growth factor.

Within about 3 to about 4 days in the presence of a growth factor, multipotent neural stem cells (i.e., βT4 cells) can form neurospheres. In the continued presence of growth factor, such as EGF or the like, βT4 cells within the neurosphere can slowly divide resulting in an increase in the size of the neurosphere and the number of undifferentiated cells. A portion (e.g., about less than about 25%) of the neurospheres so formed are immunoreactive for βT4 and Olig2 but not immunoreactive for GFAP, NG2 and PLP. Antibodies are available to identify βT4, GFAP, NG2 and PLP.

Figure 10:
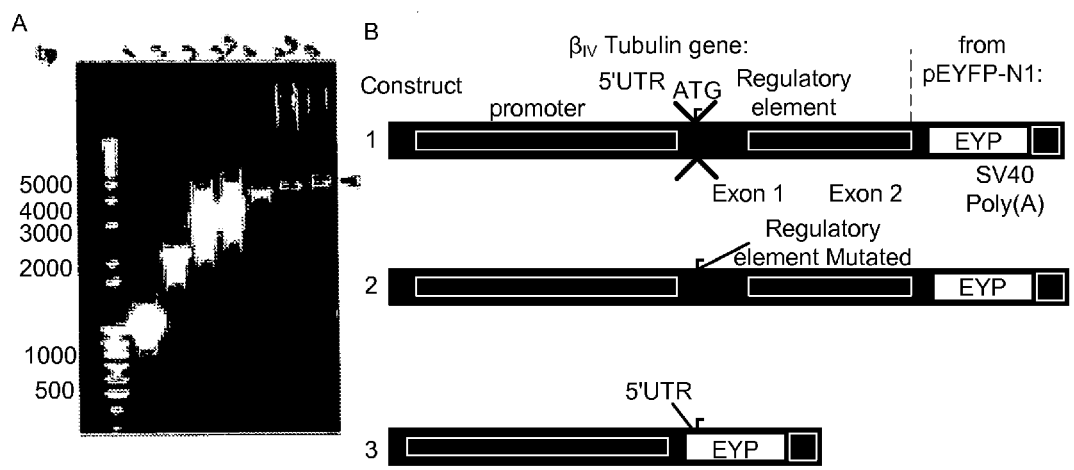
FIGS. 10(A-B) illustrate construction of EYFP transgenes using the βT4 promoter. The longest fragment obtained by PCR upstream from $β_{IVa}$ tubulin exon 1 was 5 kb (A), and used in 3 constructs (B). The first (B, 1) included exon 1, intron 1, and part of exon 2, inserted ahead of EYFP and SV40 polyA signal in expression vector pEYFP-N1 (B). In the second (B, 2), a translational regulatory element was inactivated. In the third (B, 3), only the exon 1 5'UTR was used (3), utilizing the translation start site from the EYFP vector.

After about 4 to about 5 days in the absence of a substrate, the proliferating neurospheres can lift off the floor of the culture dish and tend to form the free-floating clusters characteristic of neurospheres. Floating neurospheres are depicted in FIG. 10A and shown in FIGS. 10B-C. The proliferating precursor cells of the neurosphere continue to proliferate in suspension. After about 3 to about 10 days in vitro, and more particularly after about 6 to about 7 days in vitro, the proliferating neurospheres can be fed every about 2 to about 7 days, for example, about 2 to about 4 days by gentle centrifugation and resuspended in a complete medium containing at least one growth factor.

The neurospheres so formed (i.e., primary neurospheres) can then be purified or enriched by treating them with an agent that kills actively dividing cells while not substantially affecting cells that exhibit slow proliferation, such as the multipotent neural cell (i.e., βT4 cells) in accordance with the invention. The agent can include, for example, cytosine β-D-arabinofuranoside (Ara-C). The Ara-C can be administered to the neurospheres after dissociation of the cells of the primary neurospheres for an amount of time effective to the kill the actively dividing dissociated cells. For example, the Ara-C can be administered for about 4 days to kill actively dividing cells.

The remaining dissociated cells are then formed into secondary neurospheres by placing the remaining dissociated cultured cells in a culture medium that promotes formation of neurosphere (e.g., DMEM/F12 media supplemented with EGF, FGF, and N2) and allowed to grow, for example, about 3 to about 4 days. The resulting neurosphere so formed comprise an enriched population of neural stem cells. For example, 96% of the total neurospheres so formed are immunoreactive for βT4 and Olig2 but not immunoreactive for GFAP, NG2 and PLP.

If desired, the neurospheres can be passaged to reinitiate proliferation. After 6-7 days in vitro, the culture flasks may be shaken well and the neurospheres allowed to settle on the bottom corner of the flask. The neurospheres may then be transferred to a 50 ml centrifuge tube and centrifuged at low speed. The medium is aspirated, and the neurospheres are re-suspended in a small amount of complete medium. Individual cells in the neurospheres can be separated by physical dissociation of the neurospheres with a blunt instrument, for example, by triturating the neurospheres with a pipette, especially a fire polished Pasteur pipette, to form a single cell suspension of neural stem cell progeny. The cells may then be counted and replated at the desired density to reinitiate proliferation. Single cells from the dissociated neurospheres may then be suspended in complete medium containing growth factor, and a percentage of these cells proliferate and form new neurospheres largely composed of undifferentiated cells. This procedure can be repeated weekly to result in a logarithmic increase in the number of viable cells at each passage. The procedure, can be continued until the desired number of neural stem cells is obtained.

This ability to enhance the enrich the population of neural stem cells can be invaluable when stem cells are to be harvested for later transplantation back into a patient, thereby making the initial surgery (1) less traumatic because less tissue would have to be removed and (2) more efficient because a greater yield of stem cells per surgery would proliferate in vitro.

Additionally, the patient's stem cells, once enriched in vitro, could also be genetically modified in vitro using the techniques described below. The in vitro genetic modification may be more desirable in certain circumstances than in vivo genetic modification techniques when more control over the transfection with the genetic material is required.

Neural stem cells (i.e., βT4 cells) can be cryopreserved until they are needed by any method known in the art. The cells can be suspended in an isotonic solution, preferably a cell culture medium, containing a particular cryopreservant. Such cryopreservants include dimethyl sulfoxide (DMSO), glycerol and the like. These cryopreservants are used at a concentration of for example about 5% to about 15%, about 8% to about 10%. Cells are frozen gradually to a temperature of about −10° C. to about −150° C., for example about −20° C. to about −100° C. or about −70° C. to about −80° C.

In another aspect of the invention, the number neural stem cell progeny proliferated in vivo from the mammalian CNS can be potentially increased by injecting a growth factor or combination of growth factors, such as EGF, FGF, Shh, or a combination thereof, into the ventricles of the donor in vivo. For example, at least one growth factor may be infused into the lateral or subventricular forebrain region(s) of a person suffering from, e.g., MS. Infusion of at least one growth factor can increase the efficiency and proliferation of the neural stem cells in vivo and thus, in the case of a person suffering from MS, promote differentiation and proliferation of neural stem cells into oligodendrocytes capable of remyelinating diseased axons.

In still another aspect, neural stem cells may be harvested from a particular area of a patient's brain, e.g., from or near a lesion in a person suffering from MS. Harvested neural stem cells may then be propagated and expanded in vitro via, for example, a neurosphere assay. Once the neural stem cells have obtained a desired concentration, the cells may then be infused back into the affected area(s) of the patient's brain. After delivery to the patient's brain, the neural cells are then able to differentiate into other neural cells, i.e., oligodendrocytes, capable of remyelinating the diseased portion(s) of the patient's brain.

Another aspect of the invention relates to a method of differentiating isolated multipotent neural stem cells in vitro to form a neural cell population. In the differentiation method in accordance with the invention, a population of neural stem cells (i.e., βT4 cells) which expresses βT4 and Olig2 and which does not express NG2, PLP and GFAP, may be selected initially. Then, at least one proliferation-inducing growth factor may be administered to the cells. The proliferation-inducing growth factor is capable of inducing the proliferation of the population into at least one neural cell, such as a neuron, astrocyte or oligodendrocyte.

Differentiation of the neural stem cells can be induced by any method known in the art which activates the cascade of biological events which lead to growth, which include the liberation of inositol triphosphate and intracellular $Ca^{2+}$, liberation of diacyl glycerol and the activation of protein kinase C and other cellular kinases, and the like. Treatment with phorbol esters, differentiation-inducing growth factors and other chemical signals can induce differentiation. Differentiation can also be induced by plating the cells on a fixed substrate such as flasks, plates, or coverslips coated with an ionically charged surface such as poly-L-lysine and poly-L-ornithine and the like.

Other substrates may be used to induce differentiation such as collagen, fibronectin, laminin, matrigel, and the like. Differentiation can also be induced by leaving the cells in suspension in the presence of a proliferation-inducing growth factor, without reinitiating proliferation (i.e., without dissociating the neurospheres).

One illustrative method for inducing differentiation of the neural stem cell progeny comprises culturing the cells on a fixed substrate in a culture medium. A proliferation-inducing growth factor can then be administered to the cells. The proliferation inducing growth factor can cause the cells to adhere to the substrate (e.g., polyomithine-treated plastic or glass), flatten, and begin to differentiate into different cell types. The culture medium can contain serum such as 0.5-1.0% fetal bovine serum (FBS), but for certain uses, if defined conditions are required, serum would not be used. Within about 2 to about 3 days, most or all of the neural stem cell progeny may begin to lose immunoreactivity for βT4 and begin to express antigens specific for neurons, astrocytes or oligodendrocytes, as determined by immunocytochemistry techniques well known in the art.

Immunocytochemistry (e.g., dual-label immunofluorescence and immunoperoxidase methods) utilizes antibodies that detect cell proteins to distinguish the cellular characteristics or phenotypic properties of neurons from astrocytes and oligodendrocytes. In particular, cellular markers for neurons include NSE, NF, MAP-2; and for glia, GFAP (an identifier of astrocytes), galactocerebroside (GalC) (a myelin glycolipid identifier of oligodendrocytes), and the like.

Immunocytochemistry can also be used to detect the expression of neurotransmitters, or in some cases the expression of enzymes responsible for neurotransmitter synthesis. For the identification of neurons, antibodies can be used that detect the presence of acetylcholine (ACh), dopamine, epinephrine, norepinephrine, histamine, serotonin or 5-hydroxytryptamine (5-HT), neuropeptides such as substance P, adrenocorticotrophic hormone, vasopressin or anti-diuretic hormone, oxytocin, somatostatin, angiotensin II, neurotensin, and bombesin, hypothalamic releasing hormones such as TRH and luteinizing releasing hormone, gastrointestinal peptides such as vasoactive intestinal peptide (VIP) and cholecystokinin (CCK) and CCK-like peptide, opioid peptides such as endorphins like β endorphin and enkephalins such as met- and leu-enkephalin, prostaglandins, amino acids such as GABA, glycine, glutamate, cysteine, taurine and aspartate and dipeptides such as carnosine. Antibodies to neurotransmitter-synthesizing enzymes can also be used, such as glutamic acid decarboxylase (GAD) which is involved in the synthesis of GABA, choline acetyltransferase (ChAT) for ACh synthesis, dopa decarboxylase (DDC) for dopamine, dopamine-β-hydroxylase (DBH) for norepinephrine, and amino acid decarboxylase for 5-HT. Antibodies to enzymes that are involved in the deactivation of neurotransmitters may also be useful such as acetyl cholinesterase (AChE) which deactivates ACh. Antibodies to enzymes involved in the reuptake of neurotransmitters into neuronal terminals such as monoamine oxidase and catechol-o-methyl transferase for dopamine, for 5-HT, and GABA transferase for GABA may also identify neurons. Other markers for neurons include antibodies to neurotransmitter receptors such as the AChE nicotinic and muscarinic receptors, adrenergic receptors $\alpha^1$, $\alpha_2$, $\beta^1$ and $\alpha_2$, the dopamine receptor and the like.

The developmental fate of neural stem cells in accordance with the present invention can also be followed using transgenic Cre-loxP technology. Cre recombinase preferentially catalyzes intramolecular recombination between two adjacent loxP sequences. Fate mapping utilizing Cre/LoxP technology can be achieved by expressing Cre under the control of a developmentally regulated promoter in transgenic animals or cells that contain a reporter gene whose expression is dependent upon the activity of Cre. The reporter construct is generally composed of 1) a ubiquitously active promoter, such as beta-actin or ROSA26, 2) a stop sequence that usually contains strong polyadenylation signals, a stop codon and 5' spliced donor site all flanked by LoxP sites, and 3) a reporter gene, such as enhanced green fluorescent protein (EGFP). In cells/tissues not expressing Cre recombinase, the reporter is not expressed due to the presence of the "stop" sequence. However, in cells/tissues in which the developmentally regulated promoter is activated, Cre catalyzes the removal of the LoxP-flanked sequence, enabling expression of the reporter in the cell of origin and all of its progeny.

To control the temporal expression of the reporter, a Cre fusion protein that is activated by binding of a ligand can be utilized. For example, Cre fused with a mutated ligand binding domain of the human estrogen receptor results in a Cre protein that is activated by tamoxifen but not estradiol. Tamoxifen binding permits nuclear translocation of Cre where it is able to catalyze loxP excision. By this method the fate of cells at specific time points in development can be identified and followed. By way of example, a number of $CreER^T$ transgenic mice have been developed for lineage tracing of neuroectodermal cells expressing a number of developmentally regulated proteins, including glial fibrillary acidic protein, proteolipid protein, nestin, Math1, and gli.

In situ hybridization histochemistry can also be performed, using cDNA or RNA probes specific for the peptide neurotransmitter or the neurotransmitter synthesizing enzyme mRNAs. These techniques can be combined with immunocytochemical methods to enhance the identification of specific phenotypes. If necessary, the antibodies and molecular probes discussed above can be applied to Western and Northern blot procedures respectively to aid in cell identification.

Type I astrocytes, which are differentiated glial cells that have a flat, protoplasmic/fibroblast-like morphology, are preferably identified by their immunoreactivity for GFAP but not A2B5. Type II astrocytes, which are differentiated glial cells that display a stellate process-bearing morphology, are preferably identified using immunocytochemistry by their phenotype GFAP(+), A2B5(+) phenotype.

Cells that do not express intermediate filaments specific for neurons or for astrocytes begin to express markers specific for oligodendrocytes in a correct temporal fashion. That is, the cells first become immunoreactive for O4, galactocerebroside (GalC, a myelin glycolipid) and finally the myelin proteins, MBP, PLP, MAG, and MOG. These cells also possess a characteristic oligodendrocyte morphology.

This embodiment of the present invention provides a method of influencing the relative proportion of these differentiated cell types by the addition of exogenous growth factors during the differentiation stage of the neural stem cells. By using dual-label immunofluorescence and immunoperoxidase methods with various neuronal- and glial-specific antibodies, the effect of the exogenous growth factors on the differentiating cells can be determined.

The biological effects of growth and trophic factors are generally mediated through binding to cell surface receptors. The receptors for a number of these factors have been identified and antibodies and molecular probes for specific receptors are available. Neural stem cells can be analyzed for the presence of growth factor receptors at all stages of differentiation. In many cases, the identification of a particular receptor will define the strategy to use in further differentiating the cells along specific developmental pathways with the addition of exogenous growth or trophic factors.

Exogenous growth factors can be added alone or in various combinations to cultures containing the neural stem cells (i.e., βT4 cells) of the present invention. They can also be added in a temporal sequence (i.e., exposure to a first growth factor influences the expression of a second growth factor receptor). Among the growth factors and other molecules that can be used to influence the differentiation of the neural stem cells in vitro are FGF-1, FGF-2, ciliary neurotrophic factor (CNTF), NGF, BDNF, neurotrophin 3, neurotrophin 4, interleukins, leukemia inhibitory factor (LIP), Shh, cyclic adenosine monophosphate, forskolin, tetanus toxin, high levels of potassium, amphiregulin, TGF-α, TGF-β, insulin-like growth factors, dexamethasone (glucocorticoid hormone), isobutyl 3-methylxanthine, somatostatin, growth hormone, retinoic acid, and PDGF. These growth factors, along with other factors, such as transcription factors (e.g., Olig1, Olig2, Mash1, Nkx2.2 and Dlx2), may also find use in the present invention.

In another embodiment of the present invention, neural stem cells (i.e., βT4 cells) may be genetically modified. The term "genetic modification" as used herein refers to the stable or transient alteration of the genotype of a neural stem cell, neural progenitor cell, or differentiated neural cell by intentional introduction of exogenous DNA. DNA may be synthetic, or naturally derived, and may contain genes, portions of genes, or other useful DNA sequences. The term "genetic modification" as used herein is not meant to include naturally occurring alterations such as that which occurs through natural viral activity, natural genetic recombination, or the like.

Exogenous DNA may be introduced to a neural stem cell, for example, by viral vectors (retrovirus, modified herpes viral, herpes-viral, adenovirus, adeno-associated virus, lentivirus, and the like) or direct DNA transfection (lipofection, calcium phosphate transfection, DEAE-dextran, electroporation, and the like). The genetically modified cells of the present invention possess the added advantage of having the capacity to fully differentiate to produce neurons or macroglial cells in a reproducible fashion using a number of differentiation protocols. The neural stem cells may be derived from transgenic animals. There are several methods presently used for generating transgenic animals. Methods based on site-specific recombination systems have been described to obtain randomly integrated single copy transgenes by excising excess linked copies from the genome (Srivastava and Ow, 1999 Proc. Natl. Acad. Sci. USA, 96:11117-11121; Srivastava and Ow, 2001 Plant Mol. Biol. 46:561-566) and to insert DNA at a known chromosome location in the genome (O'Gorman et al., 1991 Science, 251:1351-55; Baubonis and Sauer, 1993 Nucl. Acids Res., 21:2025-29). These methods make use of site-specific recombination systems that are freely reversible. These reversible systems include the following: the Cre-lox system from bacteriophage P1 (Baubonis and Sauer, 1993, supra; Albert et al., 1995 Plant J., 7:649-59), the FLP-FRT system of *Sacchromyces cerevisiae* (O'Gorman et al., 1991, supra), the R-RS system of *Zygosaccharomyces rouxii* (Onouchi et al., 1995 Mol. Gen. Genet. 247: 653-660), a modified Gin-gix system from bacteriophage Mu (Maeser and Kahmann, 1991 Mol. Gen. Genet., 230:170-76), the β-recombinase-six system from a *Bacillus subtilis* plasmid (Diaz et al., 1999 J. Biol. Chem. 274: 6634-6640), and the γδ-res system from the bacterial transposon Tn1000 (Schwikardi and Dorge, 2000 FEBS let. 471: 147-150). Cre, FLP, R, Gin, β-recombinase and γδ are the recombinases, and lox, FRT, RS, gix, six and res the respective recombination sites (reviewed by Sadowski, 1993 FASEB J., 7:750-67; Ow and Medberry, 1995 Crit. Rev. Plant Sci. 14: 239-261).

The recombination systems above have in common the property that a single polypeptide recombinase catalyzes the recombination between two sites of identical or nearly identical sequences. Each recombination site consists of a short asymmetric spacer sequence where strand exchange takes place, flanked by an inverted repeat where recombinases bind. The asymmetry of the spacer sequence gives an orientation to the recombination site, and dictates the outcome of a recombination reaction. Recombination between directly or indirectly oriented sites in cis excises or inverts the intervening DNA, respectively. Recombination between sites in trans causes a reciprocal translocation of two linear DNA molecules, or co-integration if at least one of the two molecules is circular. Since the product-sites generated by recombination are themselves substrates for subsequent recombination, the reaction is freely reversible. In practice, however, excision is essentially irreversible because the probability of an intramolecular interaction, where the two recombination-sites are closely linked, is much higher than an intermolecular interaction between unlinked sites. The corollary is that the DNA molecule inserted into a genomic recombination site will readily excise out.

In contrast to the freely reversible recombination systems, there are recombination systems that can catalyze irreversible reactions. In one such system from bacteriophage λ, the λ integrase recombines non-similar sequences known as attB and attP to from attL and attR, respectively. This reaction requires DNA supercoiling of the target sites, and accessory proteins IHF and FIS. The reverse reaction, from attL×attR to form attB and attP, requires an additional excision-specific protein known as XIS. Mutant integrase proteins can perform intramolecular, but not intermolecular, reactions without these requirements. Using these mutant λ integrases, Lorbach et al. (2000 J. Mol. Biol., 296:1175-81) demonstrated DNA inversions in recombination targets introduced into the human genome.

Other techniques include retroviral-mediated transfer, or gene transfer in embryonic stem cells. These techniques and others are detailed by Hogan et al. in *Manipulating the Mouse Embryo, A Laboratory Manual* (Cold Spring Harbor Laboratory Ed., 1986). Use of these transgenic animals has certain advantages including the fact that there is no need to transfect healthy neurospheres. Cells derived from transgenic animals will exhibit stable gene expression.

A significant challenge for cellular transplantation in the CNS is the identification of the donor cells after implantation within the host. A number of strategies have been employed to mark donor cells, including tritated labels, fluorescent dyes, dextrans, and viral vectors carrying reporter genes. However, these methods suffer from inherent problems of toxicity, stability, or dilution over the long term. The use of neural cells derived from transgenic animals may provide an improved means by which identification of transplanted neural cells can be achieved. A transgenic marking system provides a more stable and efficient method for cell labeling. In this system, promoter elements, for example for GFAP and MBP, can direct the expression of the *E. coli* β-galactosidase reporter gene in transgenic mice. In these systems, cell-specific expression of the reporter gene occurs in astrocytes (GFAP-lacZ) and in oligodendrocytes (MBP-α) in a developmentally-regulated manner. The Rosa26 transgenic mice, for example, is one example of a transgenic marking system in which all cells ubiquitously express β-galactosidase.

In an aspect of the invention, once propagated, the neurosphere cells may be mechanically dissociated into a single cell suspension and plated on petri dishes in a medium where they are allowed to attach overnight. The neural stem cells may then genetically modified. If the neural stem cells are generated from transgenic animals, then they may or may not be subjected to further genetic modification, depending upon the properties desired of the cells. Any useful genetic modification of the cells is within the scope of the present invention. For example, neural stem cells may be modified to produce or increase production of a biologically active substance such as a neurotransmitter or growth factor or the like. The genetic modification may be performed either by infection with recombinant retroviruses or transfection using methods known in the art (see Maniatis et al., *in Molecular Cloning: A Laboratory Manual*, Cold Spring Harbor Laboratory, N.Y. (1982)). Briefly, the chimeric gene constructs will contain viral, for example retroviral long terminal repeat (LTR), simian virus 40 (SV40), cytomegalovirus (CMV); or mammalian cell-specific promoters such as tyrosine hydroxylase (TH, a marker for dopamine cells), DBH, phenylethanolamine N-methyltransferase (PNMT), ChAT, GFAP, NSE, the NF proteins (NF-L, NF-M, NF-H, and the like) that direct the expression of the structural genes encoding the desired protein. In addition, the vectors will include a drug selection marker, such as the *E. coli* aminoglycoside phosphotransferase gene, which when coinfected with the experimental gene, confers resistance to geneticin (G418), a protein synthesis inhibitor.

When the genetic modification is for the production of a biologically active substance, the substance will generally be one that is useful for the treatment of a given CNS disorder. For example, it may be desired to genetically modify cells so they secrete a certain growth factor product. As used herein, the term "growth factor product" refers to a protein, peptide, mitogen, or other molecule having a growth, proliferative, differentiative, or trophic effect. Growth factor products useful in the treatment of CNS disorders include, but are not limited to, Shh, BMPs, NGF, BDNF, the neurotrophins (NT-3, NT4/NT-5), CNTF, amphiregulin, FGF-1, FGF-2, EGF, TGFα, TGFβs, PDGF, IGFs, and the interleukins.

βT4 cells can also be modified to express a certain growth factor receptor (r) including, but not limited to, p75 low affinity NGFr, CNTFr, the trk family of neurotrophin receptors (trk, trkB, trkc), EGFr, FGFr, and amphiregulin receptors. Cells can be engineered to produce various neurotransmitters or their receptors such as serotonin, L-dopa, dopamine, norepinephrine, epinephrine, tachykinin, substance-P, endorphin, enkephalin, histamine, N-methyl D-aspartate, glycine, glutamate, GABA, ACh, and the like. Useful neurotransmitter-synthesizing genes include TH, DDC, DBH, PNMT, GAD, tryptophan hydroxylase, ChAT, and histidine decarboxylase. Genes that encode for various neuropeptides, which may prove useful in the treatment of CNS disorders, include substances, neuropeptide-Y, enkephalin, vasopressin, VIP, glucagon, bombesin, CCK, somatostatin, calcitonin gene-related peptide, and the like.

After successfully transfected/infected cells are selected they can be cloned using limiting dilution in 96 multi-well plates and assayed for the presence of the desired biologically active substance. Clones that express high levels of the desired substance may be grown and their numbers expanded in T-flasks. The specific cell line can then be cyropreserved. Multiple clones of genetically modified precursor cells may then be obtained.

The genetically modified precursor cells can be implanted for cell/gene therapy into the CNS of a recipient in need of the biologically active molecule produced by the genetically modified cells. Transplantation techniques are detailed below.

Alternatively, the genetically modified cells can be subjected to various differentiation protocols in vitro prior to implantation. For example, genetically modified cells may be removed from the culture medium which allows proliferation and differentiated using any of the protocols described above. The protocol used will depend upon the type of genetically modified cell desired. Once the cells have differentiated, they may again be assayed for expression of the desired protein. Cells having the desired phenotype can be isolated and implanted into recipients in need of the protein or biologically active molecule that is expressed by the genetically modified cell.

In yet another embodiment of the present invention, the neural stem cells (i.e., βT4 cells) may be transplanted into patients suffering from a CNS disorder.

It is well recognized in the art that transplantation of tissue into the CNS offers the potential for treatment of neurodegenerative disorders and CNS damage due to injury. Transplantation of new cells into the damaged CNS has the potential to repair damaged circuitries and provide neurotransmitters thereby restoring neurological function. However, the absence of suitable cells for transplantation purposes has prevented the full potential of this procedure from being met. "Suitable" cells are cells that meet the following criteria: (1) can be obtained in large numbers; (2) can be proliferated in vitro to allow insertion of genetic material, if necessary; (3) are capable of surviving indefinitely but stop growing after transplantation to the brain; (4) are non-immunogenic, preferably obtained from a patient's own tissue; and (5) are able to form normal neural connections and respond to neural physiological signals. The multipotent neural stem cells of the present invention, which are obtainable from embryonic or adult CNS tissue, meet all of the desirable requirements of cells suitable for neural transplantation purposes and are a particularly suitable cell line as the cells have not been immortalized and are not of tumorigenic origin.

The neural stem cells and/or their progeny can be administered to any animal with abnormal neurological or neurodegenerative symptoms obtained in any manner, including those obtained as a result of mechanical, chemical, or electrolytic lesions, as a result of experimental aspiration of neural areas, or as a result of aging processes.

Neural stem cells may be harvested from a person suffering from a CNS disease and then expanded in culture as described above. Alternatively, the present invention allows the use of neural stem cells prepared from donor tissue which is xenogeneic to the host. Since the CNS is a somewhat immunoprivileged site, the immune response is significantly less to xenografts, than elsewhere in the body. Additionally, since neural stem cells typically do not exhibit, or exhibit very little, major histocompatibility complex (MHC) gene expression, immunoreactivity to xenogenic neural stem cells may be significantly diminished. In general, however, in order for xenografts to be successful it is preferred that some method of reducing or eliminating the immune response to the implanted tissue be employed. Thus, recipients will often be immunosuppressed, either through the use of immunosuppressive drugs such as cyclosporin, or through local immunosuppression strategies employing locally applied immunosuppressants.

As an alternative to employing immunosuppression techniques, methods of gene replacement or knockout using homologous recombination in embryonic stem cells, and extended to gene replacement or knockout in cell lines, can be applied to precursor cells for the ablation of major histocompatibility complex (MHC) genes. Neural stem cells or neural progenitor cells lacking MHC expression would allow for the grafting of enriched neural cell populations across allogeneic, and perhaps even xenogeneic, histocompatibility barriers without the need to immunosuppress the recipient. Alternatively, the immunogenicity of the graft may be reduced by preparing neural stem cells from a transgenic animal that has altered or deleted MHC antigens.

Upon suitable expansion of cell numbers, the neural stem cells may be harvested, genetically modified if necessary, and readied for direct injection into the recipient's CNS. Neural stem cells, when administered to the particular neural region, preferably form a neural graft which forms normal neuronal or synaptic connections with neighboring neurons. Additionally, the implanted cells may maintain contact with other transplanted or existing glial cells which may in turn form myelin sheaths around the neurons' axons, and provide a trophic influence for the neurons. As these transplanted cells form connections, they re-establish the neuronal networks which have been damaged due to disease and aging.

Survival of the graft in the living host can be examined using various non-invasive scans such as computerized axial tomography (CAT scan or CT scan), nuclear magnetic resonance or magnetic resonance imaging (NMR or MRI) or more preferably positron emission tomography (PET) scans.

Functional integration of the graft into the host's neural tissue can be assessed by examining the effectiveness of grafts on restoring various functions, including but not limited to tests for endocrine, motor, cognitive and sensory functions. Motor tests which can be used include those which quantitate rotational movement away from the degenerated side of the brain, and those which quantitate slowness of movement, balance, coordination, akinesia or lack of movement, rigidity and tremors. Cognitive tests include various tests of ability to perform everyday tasks, as well as various memory tests, including maze performance.

Neural stem cell progeny can also be produced and transplanted using the above procedures to treat demyelination diseases. Human demyelinating diseases for which the cells of the present invention may provide treatment include disseminated perivenous encephalomyelitis, MS (Charcot and Marburg types), neuromyelitis optica, concentric sclerosis, acute, disseminated encephalomyelitides, post encephalomyelitis, postvaccinal encephalomyelitis, acute hemorrhagic leukoencephalopathy, progressive multifocal leukoencephalopathy, idiopathic polyneuritis, diphtheric neuropathy, Pelizaeus-Merzbacher disease, neuromyelitis optica, diffuse cerebral sclerosis, central pontine myelinosis, spongiform leukodystrophy, and leukodystrophy (Alexander type).

Areas of demyelination in humans is generally associated with plaque like structures. Plaques can be visualized by magnetic resonance imaging, and accessible plaques may be the target area for injection of neural stem cells and/or their progeny. Standard stereotactic neurosurgical methods may be used to inject neural stem cell suspensions both into the brain and spinal cord. Generally, the cells can be obtained from any of the sources discussed above.

For example, oligodendrocyte progenitor cells derived from the neural stem cells of the present invention may be proliferated and differentiated in vitro and may then be injected into demyelinated target areas in the recipient. Appropriate amounts of type I astrocytes may also be injected. Type I astrocytes are known to secrete PDGF which promotes both migration and cell division of oligodendrocytes.

In an aspect of the invention, the treatment of demyelination disease can use undifferentiated neural stem cell progeny. Neurospheres grown in the presence of a proliferation-inducing growth factor can be dissociated to obtain individual precursor cells which are then placed in injection medium and injected directly into the demyelinated target region. The cells then differentiate in vivo.

The injection of neural stem cells (i.e., βT4 cells) in remyelination therapy provides, amongst other types of cells, a source of immature oligodendrocytes and OPCs. This is a significant feature because oligodendrocytes are capable of remyelinating axons in patients with MS.

The injection of neural stem cells (i.e., βT4 cells) is also significant in remyelination therapy because the neural stem cells may be able to differentiate into type I astrocytes at the implant site. This is a significant feature because immature, as opposed to mature, type I astrocytes are known to migrate away from the implant site when implanted into a mature recipient, and become associated with blood vessels in the recipient's CNS. This is at least partially due to the fact that immature astrocytes are intrinsically more motile than mature astrocytes. Type I astrocytes differentiating at or near the stem cell implant site should have maximal motility and thereby optimize the opportunity for oligodendrocyte growth and division at sites distant from the implant. The localization of the astrocytes near blood vessels is also significant from a therapeutic standpoint since (at least in MS) most plaques have a close anatomical relationship with one or more veins.

Any suitable method for the implantation of neural stem cells near the demyelinated targets may be used so that the cells can become associated with the demyelinated axons. Glial cells are motile and are known to migrate to, along, and across their neuronal targets thereby allowing the spacing of injections. Remyelination by the injection of stem cells is a useful therapeutic in a wide range of demyelinating conditions. It should also be borne in mind that in some circumstances remyelination may not result in permanent remyelination, and repeated injections will be required.

In one embodiment of the present invention, neural stem cells (i.e., βT4 cells) can be induced to proliferate and differentiate in vivo by administering to the host any growth factor(s) or pharmaceutical composition(s) capable of inducing proliferation and differentiation of the cells. These growth factors include any growth factor known in the art, including the growth factors described above for in vitro proliferation and differentiation. Pharmaceutical compositions include any substance that blocks the inhibitory influence and/or stimulates neural stem cells and stem cell progeny to proliferate and ultimately differentiate. Thus, the techniques described above to proliferate, differentiate, and genetically modify neural stem cells in vitro can be adapted to in vivo techniques to achieve similar results. Such in vivo manipulation and modification of these cells allows cells lost, due to injury or disease, to be endogenously replaced, thus obviating the need for transplanting foreign cells into a patient. Additionally, the cells can be modified or genetically engineered in vivo so that they express various biological agents useful in the treatment of neurological disorders.

Administration of growth factors can be done by any method, including injection cannula, transfection of cells with growth hormone-expressing vectors, injection, timed-release apparati which can administer substances at the desired site, and the like. Pharmaceutical compositions can be administered by any method, including injection cannula, injection, oral administration, timed-release apparati and the like. The neural stem cells can be induced to proliferate and differentiate in vivo by induction with particular growth factors or pharmaceutical compositions which will induce their proliferation and differentiation. Therefore, this latter method circumvents the problems associated with transplantation and immune reactions to foreign cells.

Growth factors can be administered in any manner known in the art in which the factors may either pass through or by-pass the blood-brain barrier. Methods for allowing factors to pass through the blood-brain barrier include minimizing the size of the factor, or providing hydrophobic factors which may pass through more easily.

The fact that neural stem cells are located in the tissues lining ventricles of mature brains offers several advantages for the modification and manipulation of these cells in vivo and the ultimate treatment of various neurological diseases, disorders, and injury that affect different regions of the CNS. Therapy for these diseases can be tailored accordingly so that stem cells surrounding ventricles near the affected region are manipulated or modified in vivo using the methods described herein. The ventricular system is found in nearly all brain regions and thus allows easier access to the affected areas. If one wants to modify the neural stem cells in vivo by exposing them to a composition comprising a growth factor or a viral vector, it is relatively easy to implant a device that administers the composition to the ventricle and, thus, to the neural stem cells. For example, a cannula attached to an osmotic pump may be used to deliver the composition. Alternatively, the composition may be injected directly into the ventricles. The neural stem cells and/or their progeny can then migrate into regions that have been damaged as a result of injury or disease. Furthermore, the close proximity of the ventricles to many brain regions would allow for the diffusion of a secreted neurological agent by the stem cells or their progeny.

For the treatment of MS and other demyelinating or hypomyelinating disorders, and for the treatment of ALS or other motor neuron diseases, growth factors or other neurological agents may be delivered to the central canal.

In addition to treating CNS tissue immediately surrounding a ventricle, a viral vector, DNA, growth factor, or other neurological agent can be easily administered to the lumbar cistern for circulation throughout the CNS. Other ways of passing the blood-brain barrier include in vivo transfection of neural stem cells and stem cell progeny with expression vectors containing genes that code for growth factors, so that the cells themselves produce the factor. Any useful genetic modification of the cells is within the scope of the present invention. For example, in addition to genetic modification of the cells to express growth factors, the cells may be modified to express other types of neurological agents such as neurotransmitters. Preferably, the genetic modification is performed either by infection of the cells lining ventricular regions with recombinant retroviruses or transfection using methods known in the art including $CaPO_4$ transfection, DEAE-dextran transfection, polybrene transfection, by protoplast fusion, electroporation, lipofection, and the like. Any method of genetic modification, now known or later developed can be used. With direct DNA transfection, cells could be modified by particle bombardment, receptor mediated delivery, and cationic liposomes. When chimeric gene constructs are used, they generally will contain viral, for example retroviral long terminal repeat (L6TR), simian virus 40 (SV40), cytomegalovirus (CMV); or mammalian cell-specific promoters such as those for TH, DBH, phenyletlhanolamine N-methyltransferase, ChAT, GFAP, NSE, the NF proteins (NF-L, NF-M, NF-H, and the like) that direct the expression of the structural genes encoding the desired protein.

If a retroviral construct is to be used to genetically endogenous neural stem cells, then it is preferable to induce the proliferation of these cells using the methods described herein. For example, an osmotic infusion pump could be used to deliver growth factors to the central canal several days prior to infection with the retrovirus. This assures that there will be actively dividing neural stem cells which are susceptible to infection with the retrovirus.

When the genetic modification is for the production of a biologically active substance, the substance will generally be one that is useful for the treatment of a given CNS disorder. For example, it may be desired to genetically modify cells so they secrete a certain growth factor product. Growth factor products useful in the treatment of CNS disorders are listed above. Cells can also be modified in vivo to express growth factor receptors, neurotransmitters or their receptors, neurotransmitter-synthesizing genes, neuropeptides, and the like, as discussed above.

Any expression vector known in the art can be used to express the growth factor, as long as it has a promoter, which is active in the cell, and appropriate termination and polyadenylation signals. These expression vectors include recombinant vaccinia virus vectors including pSCII, or vectors derived various viruses such as from Simian Virus 40 (SV40, i.e., pSV2-dhfr, pSV2neo, pko-neo, pSV2gpt, pSVT7 and pBABY), from Rous Sarcoma Virus (RSV, i.e., pRSVneo), from mouse mammary tumor virus (MMTV, i.e., pMSG), from adenovirus (pMT2), from herpes simplex virus (HSV, i.e., pTK2 and pHyg), from bovine papillomavirus (BPV, i.e., pdBPV and pBV-1MTHA), from Epstein-Barr Virus (EBV, i.e., p205 and pHEBo) or any other eukaryotic expression vector known in the art.

In another embodiment of the present invention, neural stem cells cultured in vitro can be used for the screening of potential neurologically therapeutic compositions. These compositions can be applied to cells in culture at varying dosages, and the response of the cells monitored for various time periods. Physical characteristics of the cells can be analyzed by observing cell and neurite growth with microscopy. The induction of expression of new or increased levels of proteins such as enzymes, receptors and other cell surface molecules, or of neurotransmitters, amino acids, neuropeptides and biogenic amines can be analyzed with any technique known in the art which can identify the alteration of the level of such molecules. These techniques include immunohistochemistry using antibodies against such molecules, or biochemical analysis. Such biochemical analysis includes protein assays, enzymatic assays, receptor binding assays, enzyme-linked immunosorbant assays (ELISA), electrophoretic analysis, analysis with high performance liquid chromatography (HPLC), Western blots, and radioimmune assays (RIA). Nucleic acid analysis such as Northern blots can be used to examine the levels of mRNA coding for these molecules, or for enzymes which synthesize these molecules.

Alternatively, cells treated with these pharmaceutical compositions can be transplanted into an animal, and their survival, ability to form neuronal connections, and biochemical and immunological characteristics examined as previously described.

Another embodiment of the present invention includes the use of neural stem cells (i.e., βT4 cells) as CNS models. For the preparation of CNS models, neural stem cells and/or stem cell progeny may be proliferated using the methods described above. Upon removal of a proliferation-inducing growth factor, proliferation of multipotent neural stem cells ceases. The neurospheres can be differentiated using the methods described above, for example by adhering the neurospheres to a substrate such as poly-ornithine-treated plastic or glass where the precursor cells begin to differentiate into neurons and glial cells. Thus, the proliferation-inducing growth factor acts as an extrinsic signaling molecule that can be added or removed at will to control the extent of proliferation.

When the proliferation-inducing growth factor is removed, the growth-factor responsive stem cell progeny can be co-cultured on a feeder layer. Many types of feeder layers may be used, such as fibroblasts, neurons, astrocytes, oligodendrocytes, tumor cell lines, genetically altered cell lines or any cells or substrate with bioactive properties. The feeder layer generally produces a broader range of phenotypes. In this instance, the feeder layer acts as a substrate and source of both membrane bound and soluble factors that induce and alter the differentiation of the stem cell-generated progeny.

The neural stem cells and/or their progeny can also be used in methods of determining the effect of a biological agent or agents thereon. The term "biological agent" refers to any agent, such as a virus, protein, peptide, amino acid, lipid, carbohydrate, nucleic acid, nucleotide, drug, pro-drug or other substance that may have an effect on neural cells whether such effect is harmful, beneficial, or otherwise. Biological agents that are beneficial to neural cells are referred to herein as "neurological agents", a term which encompasses any biologically or pharmaceutically active substance that may prove potentially useful for the proliferation, differentiation, lineage commitment, or functioning of CNS cells or treatment of neurological disease or disorder. For example, the term may encompass certain neurotransmitters, neurotransmitter receptors, growth factors, growth factor receptors, and the like, as well as enzymes used in the synthesis of these agents. Examples of biological agents include growth factors such as Shh, FGF-1, FGF-2, EGF and EGF-like ligands, TGFα, IGF-1, NGF, PDGF, and TGFβs; trophic factors such as BDNF, CNTF, and glial-derived neurotrophic factor (GDNF); regulators of intracellular pathways associated with growth factor activity such as phorbol 12-myristate 13-acetate, staurosporine, CGP-41251, tyrphostin, and the like; hormones such as activin and TRH; various proteins and polypeptides such as interleukins, the Bcl-2 gene product, bone morphogenic protein (BMP 2), macrophage inflammatory proteins; oligonucleotides such as antisense strands directed, for example, against transcripts for EGF receptors, FGF receptors, and the like; heparin-like molecules such as heparan sulfate; and a variety of other molecules that have an effect on neural stem cells or stem cell progeny including amphiregulin, retinoic acid, tumor necrosis factor alpha, and other chemicals or small molecules.

The ability of various biological agents to increase, decrease or modify in some other way the number and nature of the neural stem cells or stem cell progeny proliferated in the presence of a proliferative factor can be screened on cells proliferated by various methods, such as those described above. Using a neurosphere assay identical to or similar to the one described above, for example, it is possible to screen for biological agents that increase the proliferative ability of neural stem cells which would be useful for generating large numbers of cells for transplantation purposes. It is also possible to screen for biological agents, which inhibit neural stem cell or progenitor cell proliferation and/or differentiation.

Changes in proliferation may be observed by an increase or decrease in the number of neurospheres that form and/or an increase or decrease in the size of the neurospheres (which is a reflection of the rate of proliferation—determined by the numbers of precursor cells per neurosphere). Thus, the term "regulatory factor" is used herein to refer to a biological factor that has a regulatory effect on the proliferation of stem cells and/or precursor cells. For example, a biological factor would be considered a "regulatory factor" if it increases or decreases the number of stem cells that proliferate in vitro in response to a proliferation-inducing growth factor. Alternatively, the number of neural stem cells that respond to proliferation-inducing factors may remain the same, but addition of the regulatory factor affects the rate at which the stem cell and stem cell progeny proliferate. A proliferative factor may act as a regulatory factor when used in combination with another proliferative factor.

Other examples of regulatory factors include heparan sulfate, TGFβs, activin, BMP-2, CNTF, retinoic acid, TNFα, MIP-1α, MIP-1β, MIP-2, NGF, PDGF, interleukins, and the Bcl-2 gene product. Antisense molecules that bind to transcripts of proliferative factors and the transcripts for their receptors also regulate stem cell proliferation. Other factors having a regulatory effect on stem cell proliferation include those that interfere with the activation of the c-fos pathway, including phorbol 12 myristate 13-acetate (PMA; Sigma), which up-regulates the c-fos pathway and staurosporine (Research Biochemical International) and CGP-41251 (Ciba-Geigy), which down regulate c-fos expression and factors, such as tyrphostin and the like, which suppress tyrosine kinase activation.

Using these screening methods, it is possible to screen for potential drug side-effects on neural stem cells by testing for the effects of the biological agents on cell and progenitor cell proliferation, and on progenitor cell differentiation or the survival and function of differentiated CNS cells. If it is desired to test the effect of the biological agent on a particular differentiated cell type or a given make-up of cells, the ratio of desired cell types obtained after differentiation can be manipulated by separating the different types of cells by, for example, the use of antibodies known to bind and thus select for a particular cell type.

The effects of the biological agents are identified on the basis of significant differences relative to control cultures with respect to criteria such as the ratios of expressed phenotypes, cell viability and alterations in gene expression. Physical characteristics of the cells can be analyzed by observing cell and neurite morphology and growth with microscopy. The induction of expression of new or increased levels of proteins such as enzymes, receptors and other cell surface molecules, or of neurotransmitters, amino acids, neuropeptides and biogenic amines can be analyzed with any technique known in the art which can identify the alteration of the level of such molecules.

The factors involved in the proliferation of stem cells and the proliferation, differentiation and survival of stem cell progeny, and/or their responses to biological agents can be isolated by constructing cDNA libraries from stem cells or stem cell progeny at different stages of their development using techniques known in the art. The libraries from cells at one developmental stage are compared with those of cells at different stages of development to determine the sequence of gene expression during development and to reveal the effects of various biological agents or to reveal new biological agents that alter gene expression in CNS cells. When the libraries are prepared from dysfunctional tissue, genetic factors may be identified that play a role in the cause of dysfunction by comparing the libraries from the dysfunctional tissue with those from normal tissue. This information can be used in the design of therapies to treat the disorders. Additionally, probes can be identified for use in the diagnosis of various genetic disorders or for use in identifying neural cells at a particular stage in development.

The present invention is further illustrated by the following examples, which are not intended to be limiting.

EXAMPLES

Example 1

β Tubulin is Selectively Expressed by Oligodendrocytes in the Central Nervous System Materials and Methods Two different polyclonal rabbit antisera against the Tie-2 C-terminal were used for immunostaining and Western blots (sc-324, Santa Cruz Biotech, Santa Cruz, Calif.; Tie21-A, Alpha Diagnostic, San Antonio, Tex.). Both were produced independently against a peptide corresponding to the mouse Tie-2 C-terminal 20 amino acids (TTLYEKFTYAGIDC-SAEEAA) (SEQ ID NO: 1); this peptide is identical in rats and humans. An additional antibody against the N-terminal of Tie-2 (Tie22-A, Alpha Diagnostic) was also used.

Several antibodies were used to identify oligodendrocytes. Monoclonal mouse antibodies directed against CNP (SMI- 91, Sternberger Monoclonal, Lutherville, Md.), CC1 (Oncogene Research Products, Boston, Mass.), and CD9 (RPM.7, Pharmingen, San Diego, Calif.) were used; CC1 and CD9 antibodies both recognize membrane proteins selectively enriched in oligodendrocytes. Rat monoclonal antibodies against PLP (kindly provided by Dr. Macklin, Cleveland Clinic Foundation) and CD9 (KMC.8, Pharmingen) were also employed. MBP was detected using either a rabbit polyclonal serum (DAKO, Carpenteria, Calif.) or mouse monoclonal (SMI94, Sternberger Monoclonais). NG2 proteoglycan, a marker for OPCs, was detected using monoclonal mouse antibodies (Chemicon, Temecula, Calif.) or rabbit polyclonal antisera (Chemicon). Glial fibrillary acidic protein (GFAP) was detected using mouse monoclonal antibodies (Roche, Indianapolis, Ind.) or rabbit polyclonal antiserum (DAKO, Carpenteria, Calif.). Monoclonal mouse anti-$\beta_{IV}$ tubulin and pan-$\beta$-tubulin antibodies were obtained from Sigma-Aldrich (St Louis, Mo.).

Tissue Preparation, Immunostaining, and Confocal Microscopy

Sprague-Dawley (SD) rats aged 3-90 days (P3-PD90) were deeply anesthetized with ketamine (100 mg/kg) and xylazine (10 mg/kg), and perfused through the heart with 4% paraformaldehyde (PFA) in 0.08 M Sorensen's phosphate buffer. The brains were removed, post-fixed overnight at 4° C., and cryoprotected in 30% sucrose. The tissue was rapidly frozen, and 30-μm sections were cut on a freezing sliding microtome. Sections were immunostained by pretreating with 10% Triton X-100 in blocking solution and incubating in primary antibodies at 4° C. overnight or for up to 5 days as required to produce optimal staining. For brightfield microscopy, tissues were incubated in biotinylated secondary antibody (Vector Laboratories, Burlingame, Calif.), followed by avidin-peroxidase treatment (ABC reagent, Vector) used according to the manufacturer's instructions. Staining was developed using diaminobenzidine (DAB; Sigma) and enhanced with osmium tetroxide treatment.

For fluorescence and confocal microscopy, sections were double labeled as previously described. After the blocking step, sections were incubated at 4° in primary antibody combinations overnight or for ≦5 days as required for optimal staining. Secondary antibodies (Vector or Jackson ImmunoResearch Laboratories, Bar Harbor, Me.), conjugated directly or via biotin-avidin cross-bridges to fluorescein or Texas Red, were used to visualize target molecules. Sections were mounted in Vectashield mountant (Vector).

Fluorescently labeled tissues were examined using a confocal laser-scanning microscope (Leica TCS-NT, Heidelberg, Germany) equipped with a 63×1.4 NA lens. Z-series of optical sections were reconstructed using Scion Image software (Scion Corporation, Frederick, Md.) and prepared using Photoshop 7 (Adobe Systems, San Jose, Calif.).

Cell Culture and Immunocytochemistry

Primary mixed glial cell cultures were prepared from 2-day-old SD rat pups. Rat pups were decapitated and the meninges removed. The cortices were then dissociated by incubation in 0.06% trypsin, 0.0006% pancreatin with subsequent trituration. Cells were plated at $10^6$ cells/60-mm poly-L-lysine-coated dishes in Dulbecco's modified Eagle's medium (DMEM; Invitrogen, Carlsbad, Calif.) supplemented with 10% fetal bovine serum (FBS). After 18 h, the cultures were incubated in DMEM with N2 supplement (Invitrogen), 10 ng/ml human recombinant PDGF-AA (R&D System, Minneapolis, Minn.) and 10 ng/ml basic fibrinogen growth factor (bFGF) from bovine pituitary gland (Sigma) and incubated for 2 days. Cultures were then transferred to DMEM with 50 ng/ml 3,3',5-triiodo-L-thyronine (T3; Sigma) and 10 ng/ml rat recombinant ciliary neurotrophic factor (Sigma) for 3 days to allow OPCs to differentiate. Cells were then fixed with 4% PFA, permeabilized with 0.1% Triton X-100 and incubated with primary and secondary antibodies as described above.

Immunoprecipitation

Postnatal 10-day-old (P10) SD rats were killed, and the brains were rapidly removed. Tissue samples were homogenized in TENT buffer (20 mM Tris pH 8.0, 1 mM EDTA, 50 mM NaCl, 1% Triton X-100, 1 mM phenylmethyl sulfonyl fluoride [PMSF] 1 μg/ml aprotinin, and 1 μg/ml leupeptin). Samples were centrifuged at 15,000 rpm for 30 min at 4° C., and supernatants were collected for immunoprecipitation and Western blot analysis. For immunoprecipitation, the supernatants (1.5 mg/ml) were preadsorbed with protein G-Sepharose (Amersham Pharmacia Biotech, Piscataway, N.J.) and then centrifuged at 16,000 g. The samples were then mixed with 2 μg/ml Tie-2 antibodies (sc-324 or Tie21-A) or control rabbit IgG (Vector) and incubated overnight at 4° C. They were incubated in 10 μg/ml protein G-Sepharose 2 h at 4° C., and the antigen-antibody-Sepharose complex was pelleted at 16,000 g. They were washed five times in TENT buffer and used for immunoblotting or mass spectrometry analysis.

Western Blotting

Rat brain supernatants or immunoprecipitated samples were solubilized in Laemmli loading buffer and 30 μg samples separated on 10% sodium dodecyl sulfate-polyacrylamide gels (SDS-PAGE). Proteins were transferred to PVDF membrane, and the membranes were blocked with 5% mile in Tris-buffered saline containing 1% Triton X-100 (TBS-T). They were incubated with Tie-2 antibodies diluted in TBS-T, and secondary peroxidase-conjugated anti-rabbit antibody (Amersham Pharmacia). They were developed using an enhanced chemiluminescence (ECL kit (Pierce, Rockford, Ill.). Some samples immunoprecipitated with Tie-2 antibodies were electrophoresed and immunoblotted using βIV tubulin antibodies.

Two-Dimensional Electrophoresis and Mass Spectrometry

The immunoprecipitated samples were resuspended in solubilization buffer (7 M urea, 2 M thiourea, 4% w/v CHAPS, 5 mM dithreitol [DTT]. For separation on 2D gels, samples were run in the first dimension on immobilized pH gradient strips (Bio-Rad, Hercules, Calif.), followed by SDS-PAGE. The gels were stained with Coomassie blue, and target protein spot identified, carefully excised from the gel, and destained. The sample was reduced with dithiothreitol, alkylated with iodoacetamide, and then trypsinized to digest the protein. The resulting peptides were recovered by extraction and sequenced by LC-tandem mass spectrometry, using a Finnigan LCQ-Deca ion trap mass spectrometry. The data from the sequencing experiment were analyzed by searching the NCBI non-redundant database with the Sequest search program. All matching spectra were verified by manual interpretation.

Results

Tie-2 C-Terminal Antibodies Stain Rate Oligodendrocytes

Immunohistochemistry using Tie-2 C-terminal antibodies (sc324,Tie21-A) on sections from developing rat brains revealed staining from postnatal day 4 (P4) and onward. Tie-2 C-terminal immunoreactivity was detectable in cells of the corpus callosum at P4 and was most intense around the corpus callosum in brains at P8-P10. Confocal imaging demonstrated Tie-2 C-terminal immunoreactivity on cells positive for oligodendrocyte markers including CNP (FIG. 1A), CC1 (FIG. 1B), MBP (FIG. 1C), CD9, and PLP. Tie-2-associated Fluoroescence was present in the cell body and the processes of these cells, and often extended to myelin internodes (FIG. 1A). Tie-2-associated labeling was observed in premyelinating oligodendrocytes (FIG. 1C), which are characterized by their short, MBP-positive processes. Neither OPCs (FIG. 1D) nor astrocytes (FIG. 1E) expressed detectable Tie-2 staining. N-terminal specific antibodies for Tie-2 did not stain oligodendrocytes. In both DAB-stained sections and by immunofluorescence, sc324 and Tie21-A antibodies labeled a similar population cells. These results demonstrate that the Tie-2 C-terminal antibodies label oligodendrocytes in vivo.

In cell culture experiments, differentiating oligodendrocytes expressed intense Tie-2 staining with the C-terminal antibodies (FIG. 1F). OPCs were identified on the basis of their morphology and were not labeled. At higher magnification (FIG. 1G), the sc324/Tie21-A antibodies appeared to label filamentous structures in the oligodendrocyte cytoplasm. Filamentous staining was surprising as Tie-2 is a transmembrane protein and was expected on the cell surface, which was not observed. The Tie-2 C-terminal antibodies also reacted with the mitotic spindle apparatus of cells dividing in these cultures (FIG. 1H). Thus, while Tie-2 C-terminal antibodies sc324 and Tie21-A label recently differentiated oligodendrocytes, they appear to label microtubules.

Tie-2 C-Terminal Antibodies React with β-Tubulin

To elucidate properties of the molecule(s) labeled by Tie-2 C-terminal antibodies, Western blot experiments were performed using cortical samples from P10 brain (FIG. 2A). Only faint immunoreactivity corresponding to the 140-kD full-length Tie-2 protein was observed. In contrast, both Tie-2 C-terminal antibodies displayed strong immunoreactivity for another protein band of 55 kD (FIG. 2A). Both 140- and 55-kDa bands were eliminated by preincubation of the primary antibody with the Tie-2 C-terminal 20-amino acid peptide, indicating that a common epitope in both Tie-2 and the 55-kD peptides was recognized. This 55-kDa peptide may have represented a Tie-2 degradation product or an unrelated protein.

To identify the 55-kDa peptide, immunoprecipitates of brain lysate were separated by 2D electrophoresis and immunoblotted using Tie-2 C-terminal antibodies (FIG. 2B). In the 55-kDa region, several peptides were detected, including IgG heavy chains contributed by the rabbit immunoglobulin used in precipitation and detection. By comparing Tie-2 and immunoprecipitates using control rabbit IgG (FIG. 2B) a single spot was resolved at 55 kD with a pI of ~5 that was not present when immunoprecipitation was performed with control rabbit IgG (FIG. 2B, bottom). When the 55-kDa/pI 5 protein spot was recovered from the 2D gel and tryptically digested, 14 peptides were detected and sequenced (Table 1). These peptides included 109 amino acids from tubulin beta-15 (NCB Accession No. 135451) and covered 24% of that sequence. The oxidized methionines that were observed are a common artifact seen in the sequencing of gel-purified proteins. These peptides matched regions of rat β-tubulin isotypes. Several peptides had sequences common to multiple β-tubulin isotypes (peptides 1, 2, 4-7, 9-11). Peptides 3, 8 and 14 all contained sequences unique to rat class II β-tubulin (Accession No. A25113). Peptide 9 is unique to class IV (NP_954525.1), while peptide 12 is only found in class I β-tubulin (AAH47993.1). Peptide 13 (NSSYFVEWIPDNVK) (SEQ ID NO: 14) contains a D→N substitution that was not found in any rat, mouse, or human β-tubulin sequence currently listed and may represent a stain-specific polymorphism.

TABLE 1

Peptide Sequences Determined by LC-Tandem Mass Spectrometry

| Peptide No. | Measured Molecular Weight | M + H⁺, Da | Peptide Sequence by CAD$^a$ (calc MW, M + H⁺, Da) |
|---|---|---|---|
| 1 | 1029.1 | +2 | TAVCDIPPER (1028.5) (SEQ ID NO: 2) |
| 2 | 1039.4 | +2 | YLTVAAVFR (1039.6) (SEQ ID NO: 3) |
| 3 | 1053.6 | +2 | YLTVAAIFR (1053.6) (SEQ ID NO: 4) |
| 4 | 1131.0 | +2 | FPGQLNADLR (1130.6) (SEQ ID NO: 5) |
| 5 | 1160.0 | +2 | LAVNMoVPFPR (1159.6) (SEQ ID NO: 6) |
| 6 | 1245.8 | +2 | ISEQFTAMoFR (1245.6) (SEQ ID NO: 7) |
| 7 | 1288.2 | +2 | KLAVMMoVPFPR (1287.7) (SEQ ID NO: 8) |
| 8 | 1384.3 | +2 | IMoNTFSVMoPSPK (1383.7) (SEQ ID NO: 9) |
| 9 | 16.17.8 | +2 | AVLVDLEPGTMoDSVR (1617.8) (SEQ ID NO: 10) |
| 10 | 1637.4 | +2 | LHFFMoPGFAPLTSR (1636.8) (SEQ ID NO: 11) |
| 11 | 1648.1 | +2 | AILVDLEPGTMooDSVR (1647.8) (SEQ ID NO: 12) |
| 12 | 1660.4 | +2 | ALTVPELTQQVFDAK (1659.9) (SEQ ID NO: 13) |
| 13 | 1698.3 | +2 | NSSYFVEWIPDNVK (1697.8) (SEQ ID NO: 14) |
| 14 | 1723.9 | +2 | ALTVPELTQQMoFDSK (1723.9) (SEQ ID NO: 15) |

Mo, methionines sulfoxide;
Moo methionines sulfone.
$^a$One-letter amino acid codes are used.

One interpretation of these results is that Tie-2 antibodies recognized multiple β-tubulins. The terminal amino acids in Tie-2 (AEEAA) resembles those of classes 1, II, and IV β-tubulins, and may Provide a basis for antibody cross reactivity. This explanation, however, seems inconsistent with the oligodendrocyte-specific immunostaining, as all these isotypes are expressed in neurons. An alternative explanation is that Tie-2 C-terminal antibodies primarily recognize an oligodendrocyte-enriched β-tubulin isotype or unique tubulin conformation, and that immunoprecipitation pulls down MT fragments containing this and other co-assembled tubulins. Immunoprecipitated α-tubulins migrate to a different location on the D2 gel and would not be included in the mass spectrometry analysis.

$β_{IV}$ Tubulin is Selectively Enriched in Oligodendrocytes and Reacts with Tie-2 C-Terminal Antibodies β-tubulin occurs in all cells and several isotypes are expressed in the rodent CNS. The oligodendrocyte-specific staining pattern obtained with the Tie-2 C-terminal antibodies, however, suggests that the antibody predominantly stains an oligodendrocyte-enriched isotype of β-tubulin. Since βI and βII isotypes are present in multiple CNS cell types and βIII is a neuron-specific, these are unlikely candidates for Tie-2-based staining. In contrast, βIV tubulin expression has been described in a subset of non-neural cells in rat postnatal cerebellum and studies suggest that βIV mRNA is enriched in oligodendrocytes.

Immunohistochemical staining of rat brains for βIV tubulin produced a similar age-dependent labeling pattern to Tie-2 C-terminal antibodies. In sections from P5 rats, the most prominent labeled cells were small oligodendrocyte-like cells in the corpus callosum and adjacent cortex. At P15, numbers of βIV tubulin-positive cells in the corpus callosum and cortex were significantly increased and most extended multiple βIV tubulin-positive processes. In adults (i.e., older than P70), oligodendrocytes were not prominently labeled by βIV tubulin antibodies.

To confirm that βIV tubulin was enriched in oligodendrocytes, P10 coronal brain sections were double labeled with antibodies against βIV tubulin and cell-specific markers. PLP (FIG. 3A), CNP and MBP labeled the βIV tubulin-expressing cells, indicating that oligodendrocytes were labeled. Double labeling with Tie-2 C-terminal and βIV tubulin antibodies demonstrated colocalization of stained cells in P10 cerebrum (FIG. 3B). GFAP-positive astrocytes did not express detectable $β_{IV}$ tubulin (FIG. 3C), nor did NG2-labeled OPCs (FIG. 3D). Pan-β-tubulin antibodies produced a generalized staining pattern in which all cells were labeled, not just the oligodendrocytes (FIG. 3E). Immunoprecipitation with Tie-2 C-terminal antibodies and immunoblotting with βIV tubulin antibodies revealed a 55-kDA band (FIG. 3F).

Figure 3:
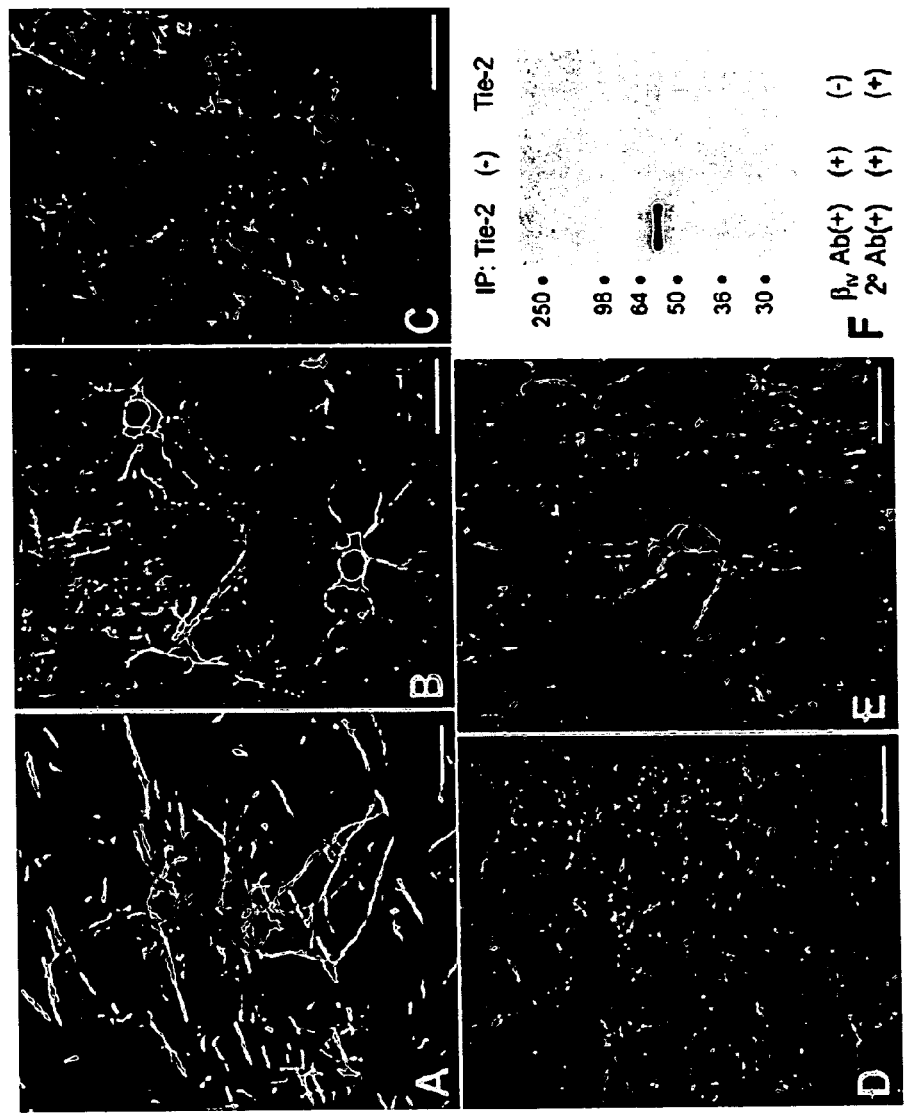
FIG. 3 illustrates βIV tubulin is expressed by oligodendrocytes. Confocal microscopy of P10 rat brain identified numerous cells that were intensely labeled by βIV tubulin antibodies (A-E). Double labeling indicated these cells were also positive for the oligodendrocyte marker CNP (A). βIV tubulin staining colocalized completely with Tie-2 C-terminal antibodies (B); minor differences in βIV tubulin and Tie-2 staining intensities are likely due to penetration differences between the antibodies. GFAP (C) and NG2 (D) did not label βIV positive cells. Staining with pan-β-tubulin antibodies (E) labeled all neurons and glia, whereas βIV tubulin was restricted to oligodendrocytes. When P10 cerebral lysate was immunoprecipitated with Tie-2 C-terminal antibodies and Western blotted (F), βIV tubulin antibody detected a 55-kDA band (lane 1) that was absent when lysates were precipitated with control rabbit IgG (lane 2) or the blots were processed without primary antibody (lane 3). Scale bars=10 μM in A; 25 μm in B-D.
Figure 4:
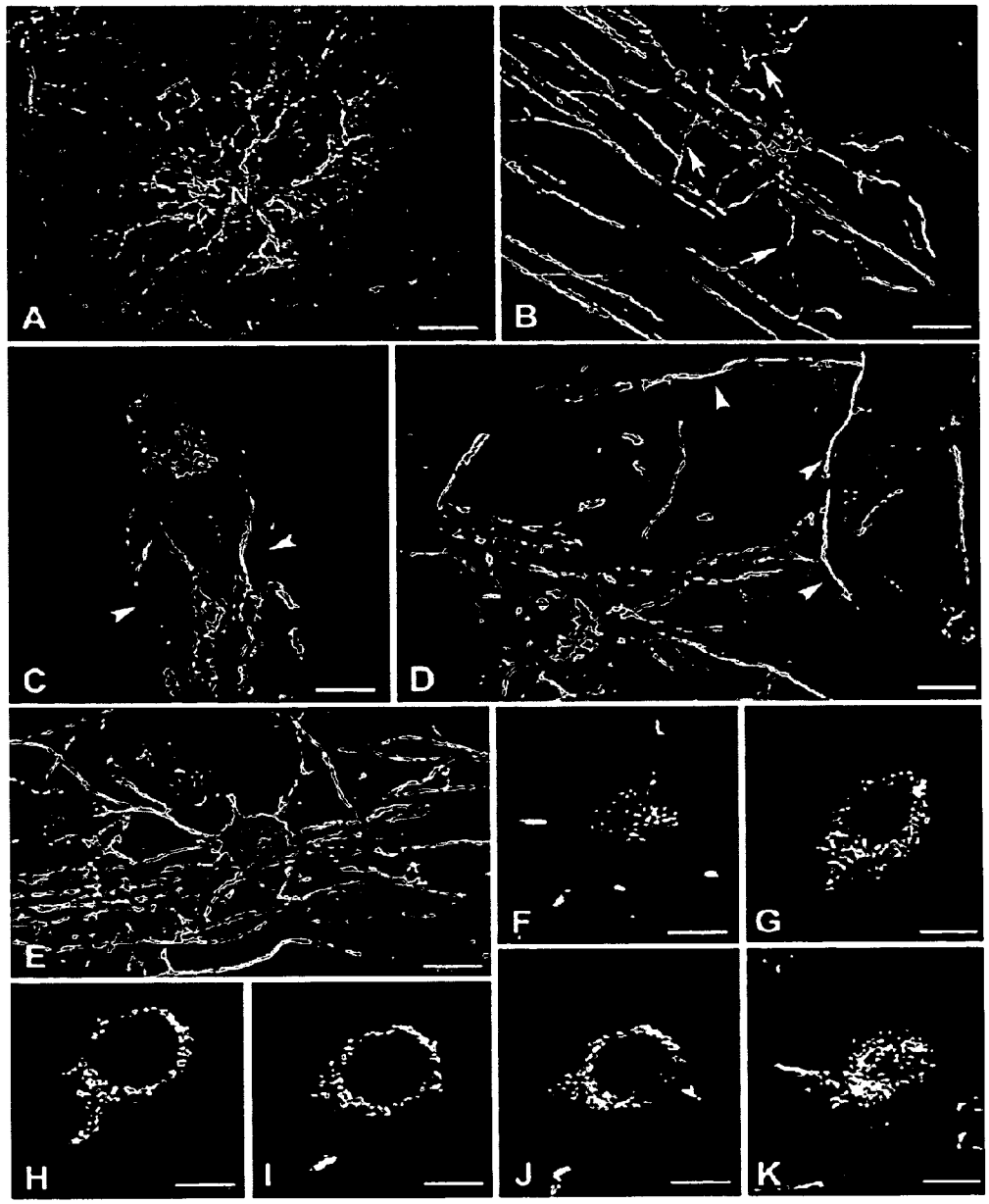
FIG. 4 illustrates βIV tubulin labels the processes and cell bodies of premyelinating and actively myelinating oligodendrocytes. Double labeling of P10 cortex for βIV tubulin (A) and CD9 (A) demonstrates βIV tubulin staining in the processes and perinuclear cytoplasm (N, nucleus) of a premyelinating oligodendrocyte. In myelinating oligodendrocytes (B,C), DIV tubulin staining delineates cytoplasmic processes (arrowheads) that extend from the oligodendrocyte cell body to the myelin internodes. The oligodendrocyte Golgi apparatus is also labeled by PLP antibodies, and appears as a series of dots scattered throughout the cell body (C, arrows). βIV staining extends in a line along the outer surface of each myelin internode (D, E), which represents the outer tongue process. Confocal z-series images of βIV labeled MTs (F-K are individual optical sections from the cell in E) demonstrated that MTs in the cell body did not emanate from a common microtubule organizing structure, such as the centrosome.
Figure 5:
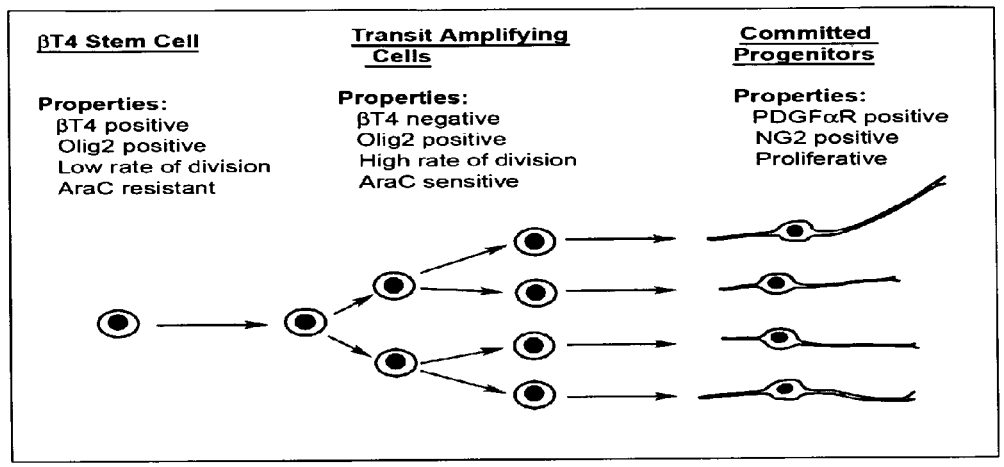
FIG. 5 is a schematic diagram showing characteristics of and relationships between the neural stem cells of the present invention (i.e., β-tubulin IV, βT4, cells), transit amplifying cells, and committed oligodendrocyte progenitor cells.

Within the oligodendrocyte lineage, βIV tubulin was not detected in OPCs (FIG. 3D), and was only detected after differentiation into premyelinating oligodendrocytes (FIG. 4A). βIV tubulin was not most abundant in the proximal processes of premyelinating cells (FIG. 4A). Staining was also detected in apoptotic oligodendrocytes (not shown). In myelinating oligodendrocytes, βIV tubulin was enriched in the cell bodies and extended into the distal processes that could be traced to the developing myelin internodes (FIG. 4B, C). A line of βIV staining also ran along the external surface of the compact myelin internode, parallel to the axon (FIG. 4D, arrows), corresponding to the oligodendrocyte outer tongue process.

By following individual oligodendrocyte cell bodies through confocal z-series (FIG. 4E-K), it was possible to observe the arrangements of cytoplasmic microtubules at many levels of the cell. Seven oligodendrocytes were analyzed in this way. From these views, the stained microtubules did not appeal anchored to a single MTOC. Consistent with this finding, the Golgi apparatus (labeled by PLP antibodies in FIG. 4C) appeared as numerous dots of staining that were scattered throughout the perinuclear cytoplasm. Because the Golgi apparatus binds to MT minus ends, this indicates that MT minus ends are dispersed within the cytoplasm, rather than concentrated at a single MTOC.

Discussion

This report demonstrates that βIV tubulin is enriched in oligodendrocytes during the premyelinating stage and initial myelination. Although antibodies directed against the Tie-2 C-terminal intensely labeled the same oligodendrocytes, the cytoskeletal pattern of staining and data from Western blots, immunoprecipitation, 2D electrophoresis and mass spectrometry all indicate that the Tie-2 C-terminal antibodies are detecting βIV tubulin demonstrates that the oligodendrocyte MT network is not centrosomally orientated. βIV tubulin therefore provides a valuable cytoskeletal marker for early stage of oligodendrocyte development. Whether βIV tubulin imparts a function that is essential to oligodendrocyte myelination remains to be determined.

Seven β-tubulin genes, (I, II, III, IVa, Ivb, V, and VI) exist in vertebrates and encode highly homologous proteins that co-assemble into MTs in vivo. Substantial differences in the C-terminals and single amino acid substitutions elsewhere differentiate each isotype. These differences contribute to isotype-specific posttranslational modification patterns and influence MT interactions with other molecules, such as MT-associated proteins (MAPs). In this study, we demonstrate that $β_{IV}$ tubulin is expressed by oligodendrocytes and assembled into MTs, and this is consistent with an earlier report that $β_{IV}$ tubulin mRNA is upregulated in remyelinating oligodendrocytes. Two βIV tubulin genes, designated $β_{IVa}$ and $β_{Ivb}$, exist in mammals. The protein products are nearly identical: the C-terminals differ by only one amino acid, and there are six amino acid substitutions (in mice) scattered elsewhere throughout the 445-amino acid polypeptide. None of the cryptic peptides generated for mass spectrometry in this study specified whether βIVa or βIvb tubulins was immunoprecipitated by Tie-2 antisera, and $β_{IV}$ tubulin antibodies recognize both isotypes. However, the predominant $β_{IV}$ tubulin mRNA in postnatal oligodendrocytes was ~2.3 kb (Schaeren-Wiemers et al., 1995), which corresponds in size to CNS-specific $β_{IVa}$ mRNA in mice and humans (Accession NM_006087.2, NM_009451.3; full-length rat βIVa sequence is not available). The $β_{Ivb}$ sequence is only ~1.6 kb (BC060597.1). Thus, during myelination, βIVa is likely to be the predominant $β_{IV}$ isotype expressed by oligodendrocytes.

Cell-specific patterns of tubulin isotype expression have been recognized for many years. In oligodendrocytes, $β_{IV}$ tubulin expression is specific for myelination, as $β_{IV}$ tubulin is not expressed by OPCs. Enrichment for $β_{IV}$ tubulin is often associated with stable or highly specialized MT networks, such as those of cilia, retinal rod cells, and neuritis. In oligodendrocytes, increased expression of $β_{IV}$ tubulin coincides with rapid cytoplasmic process outgrowth to establish myelin internodes, which necessarily involves MT stabilization to produce longer and more numerous MTs. Different β-tubulin isotypes co-assemble into MTs in vivo, which indicates that the β-tubulins are functionally interchangeable in their ability to form MTs. Cell use of particular isotypes may therefore reflect the evolutionary history of that cell rather than major functional differences between β-tubulin isotypes. Each β-tubulin class is highly conserved, however, suggesting that preservation of their structural differences is functionally important. Isotype-specific C-terminals interact differentially with some MAP, and isotype-related differences in MAP-promoted MT assembly have been reported. Oligodendrocytes upregulate MAP-1B, MAP-2c, MAP-2e (also called MAP2+13), MAP-4, and the four-repeat tau isoforms during myelination. Enrichment for βIV tubulin and these MAPs may promote formation of an MT network with stability and transport characteristics necessary for myelination.

The oligodendrocyte MT network undergoes substantial changes in organization during differentiation, expanding hundreds of micrometers to support transport into oligodendrocyte processes that reach and myelinate as many as 50 axons. Expansion and reorganization of the MT network is essential for myelination as targeting of both major myelin proteins is MT-dependent; PLP/DM-20 is transported in vesicles from the trans-Golgi network, while myelin basic protein mRNAs are transported in granules along MTs. MTs also mediate transport and organization of mitochondria, endoplasmic reticulum, and endosomes throughout the oligodendrocyte-myelin unit. Using βIV tubulin to selectively label the oligodendrocyte MT network, we were able to document the absence of a centrosomal MTOC in vivo. Previous in vitro studies showed that the centrosomal MTOC is lost as oligodendrocytes differentiate from OPCs. As in myelinating Schwann cells, perinuclear dispersion of MT minus ends decentralizes the Golgi apparatus and other minus-end associated organelles, as was observed in this study (FIG. 4D) and described by others. Release of MT minus ends from the centrosome is also necessary to produce free microtubules that can be transported into the distal cytoplasmic processes and outer tongue process. In Schwann cells, such changes in MT organization are regulated by the axon. In oligodendrocytes, development of a non-centrosomal MT network and upregulation of βIV tubulin expression occur in cultures without neurons.

Identifying oligodendrocytes that are in the premyelinating or early myelinating stages of differentiation is also important for studies of remyelination. βIV tubulin is expressed during early stages of myelination in rats, mice and human and in remyelinating oligodendrocytes in multiple sclerosis lesions. MAP2e and quaking proteins QKI5-7 have also been used to label cells undergoing oligodendrogenesis in multiple sclerosis brain; however, available MAP2e reagents label only human cells. βIV tubulin has been detected in oligodendroglioma cells, as is MAP 2e. Understanding the functional implications of $β_{IV}$ tubulin enrichment during oligodendrogenesis will require further study. Nevertheless, in the same way that $β_{III}$ tubulin has been an invaluable cell-specific cytoskeletal marker for neurons, even though the functional significance is not fully understood, βIV staining is also a valuable marker for oligodendrocytes.

Figure 6:
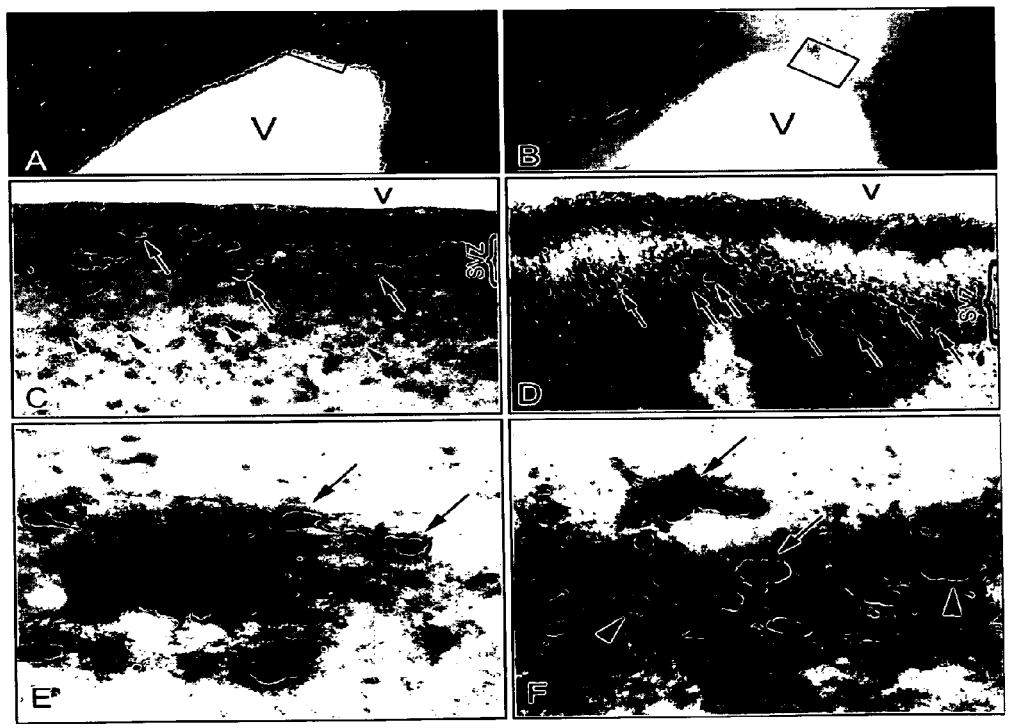
FIGS. 6(A-F) show βIV tubulin antibody-stained oligodendrocytes and a population of undifferentiated cells in the subventricular zone (SVZ). βT4 cells are increased in the SVZ of multiple sclerosis (MS) brains. In periventricular regions of both control (FIG. 6A) and MS (FIG. 6B) brains (stained for myelin), βIV tubulin antibody detects distinct populations of immature appearing cells (arrows) in the SVZ (control, from box in FIG. 6A.

Example 2

βT4 Cells Express Olig2 in the Human SVZ

βT4 cells in MS human brain were identified using two different antibodies to the C-terminal portion of Tie 2, the receptor for angiopoetin. A series of Western blot, immunoprecipitation and mass spectrometry experiments established that the major antigen recognized by these C-terminal Tie 2 antibodies was the βIV isotype of tubulin. When MS brain was examined, βIV tubulin antibodies stained oligodendrocytes and a population of undifferentiated cells in the SVZ (FIG. 6). These βT4 cells were detected in SVZs bordering MS lesions (FIGS. 6D-F), and appeared to be increased compared to adjacent myelinated regions of MS brains. In both control (FIG. 6C) and MS brains, βT4 cells often occur in doublets or clusters (FIG. 6E and FIG. 6F). Many extend short processes and some have bipolar shapes. In adult brain, oligodendrocyte cell bodies were weakly stained by βIV tubulin antibodies (FIG. 6C, arrowheads). SVZ cells were then phenotyped. They were neither NG2- nor PLP-positive indicating they were not oligodendrocyte progenitor cells (OPCs) or oligodendrocytes. They were negative for GFAP (FIG. 7A) and Iba, markers for astrocytes and microglia. SVZ βT4 cells were, however, positive for Olig2 (FIG. 7B), a b-HLH transcription factor expressed by SVZ cells that can give rise to oligodendrocyte progenitor cells. Oligodendrocytes were also Olig2-positive (FIG. 7C).

Example 3

Distribution of βT4 Cells in Developing Human Brain

Figure 8:
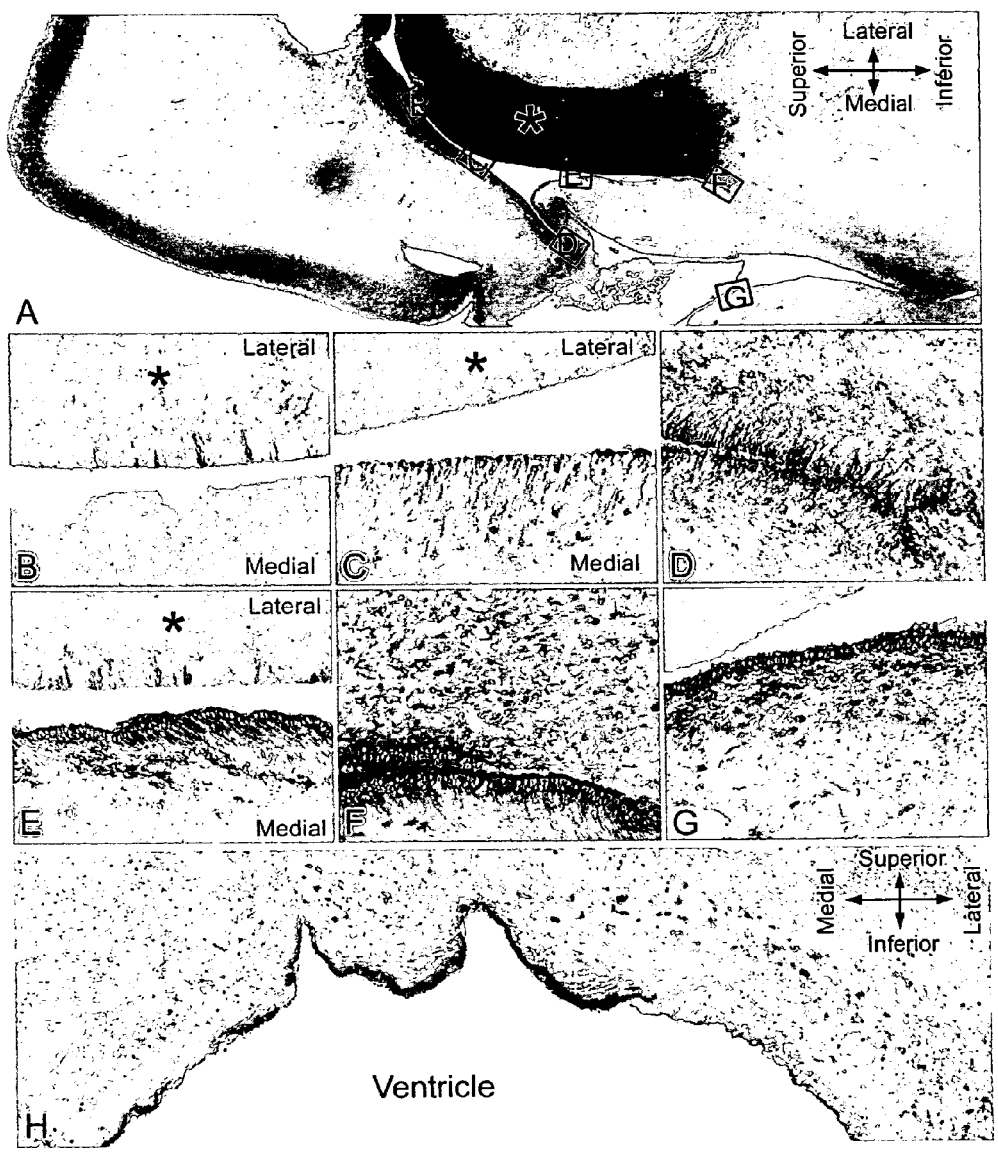
FIGS. 8(A-H) are H&E-stained micrographs showing the distribution of βT4 cells along the lateral ventricle during human fetal brain development. H&E staining shows the anatomic structure of a 19-week fetal brain section (FIG. 8A). The SVZ overlying the caudate nucleus (dark 'germinal matrix') is denoted by an asterisk. βT4 staining in six regions along the ventricle are shown (FIGS. 8B-G, locations from red boxes in FIG. 8A). The number of βT4 cells varies along the SVZ. There are numerous cells in the medial (FIGS. 8C-E) and ventral (inferior.

We hypothesized that if βT4 cells were related to oligodendrocyte progenitor production, they should be abundant in human fetal brain. We stained sections from human fetal brains with βIV tubulin antibodies. In sections from a 19-week post-conception fetus (FIGS. 8A-G), βT4 cells were abundant. The number of βT4 cells varied along the SVZ (FIGS. 8B-G). Surprisingly, the germinal matrix zone that borders the caudate nucleus at this age (FIG. 8A—dark blue band) contained very few βT4 positive cells. Medial to this zone, and on the other side of the ventricle, βT4 cells were abundant (FIG. 8C and FIG. 8E) and were found at higher density in more ventral regions (FIG. 8G). The distribution and density of βT4 cells during human fetal brain development appear to change dramatically as the fetal brain develops.

Figure 9:
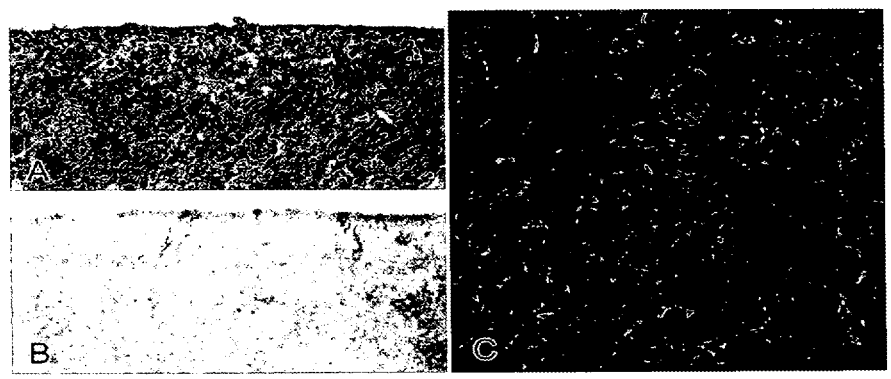
FIGS. 9(A-C) show a confocal micrograph of βT4 cells stained with polysialyated neural cell adhesion molecule (PSA-NCAM) antibodies. βT4 cells are negative for PSA-NCAM. In the germinal matrix zone, numerous PSA-NCAM-positive cells (FIG. 9A) but few βT4 cells (FIG. 9B) were detected. In other areas, confocal imaging of double-labeled tissue indicated that βT4 cells (FIG. 9C) and PSA-NCAM cells (FIG. 9C), were both present, but distinct cell populations.

It is believed that βT4 cells are related to the second wave of gliogenesis that occurs during late fetal and early postnatal periods in rodents. Fetal SVZ βT4 cells were negative for GFAP, Iba, NG2 and PLP indicating that they do not express astrocytic, microglial, OPC or oligodendrocyte markers. The lack of GFAP also suggests that βT4 cells differ from multipotent stem cells identified previously. In addition to these glial cell markers, fetal human βT4 cells were negative for the immature neuronal marker Tuj-1 (neuron specific class III β-tubulin), neuronal nuclei (NeuN) and polysialyated neural cell adhesion molecule (PSA-NCAM) (FIG. 9). PSA-NCAM antibodies stained the majority of cells in the major germinal matrix zone, dissociating PSA-NCAM cells and βT4 cells at this location (FIG. 9A and FIG. 9B). In other regions of the SVZ, βT4 and PSA-NCAM cells were both present, and in distinct cell populations (FIG. 9C).

Example 4

Fate Mapping βT4 Cell Progeny

Figure 2:
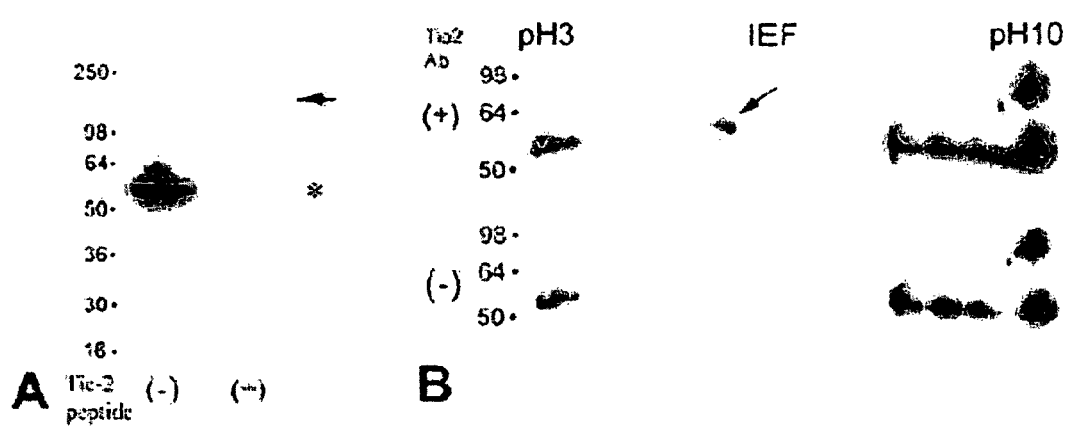
FIG. 2 illustrates Tie-2 C-terminal antibodies detect β-tubulin from rat brain. Western blot of P10 rat cerebral lysate (A lane 1, 30 μg protein/lane) using Tie-2 C-terminal antibodies identified a minor band at ~140 kDa corresponding to Tie-2 (arrow) and a 55-kD protein (asterisk). Both protein bands were eliminated by pretreatment with Tie-2 C-terminal peptide (lane 2). P10 brain lysate was immunoprecipitated, separated by 2D electrophoresis and Western blotted (B). Tie-2 antibodies detected a spot of ~55 kDA and pI ~5.0 (B, arrow, top) which was not present after immunoprecipitation with control rabbit IgG (B, bottom). Other spots on the gels represent rabbit IgG heavy chains used in the immunoprecipitation. Tryptic peptides extracted from this spot were sequenced by LC-tandem mass spectrometry (Table 1) and all 14 mapped β-tubulins.
Figure 11:
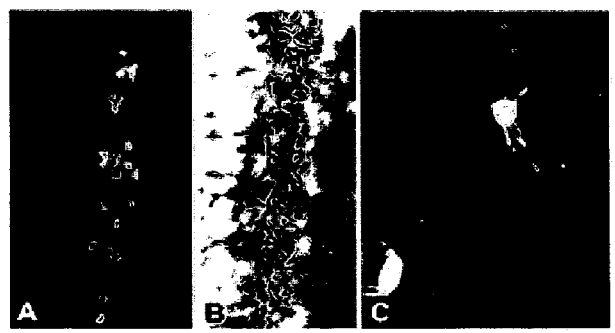
FIG. 11(A-C) illustrate βT4 promoter expression in postnatal transgenic mice. By confocal microscopy, EYFP was detected as clusters of small cells adjacent to the ventricle (A) at P0 (homozygous for construct 2 in FIG. 10B). The morphology and distribution of EYFP-expressing cells was similar to βT4 cells observed by βT4 immunostaining (B, wt mouse). At P15, myelin-forming oligodendrocytes in also expressed EYFP (C).

Fate mapping the progeny of βT4-expressing cells in vivo can be performed use Cre/loxP technology to selectively activate an EGFP transgene in these cells. The first step in this process is to generate mice in which the βT4 promoter drives a fusion protein of Cre recombinase and estrogen receptor (Cre-ER$^{T2}$). Two $β_{IV}$ tubulin genes exist in mammals, βIVa and βIVb. The predominant $β_{IV}$ tubulin mRNA in postnatal oligodendrocytes is βIVa. The mouse gene is named Tubb4 and is located on chromosome 17. We identified several BACs spanning this region. The longest fragment obtained by PCR was 5 kb upstream of exon 1 (FIG. 10A). We used this sequence to generate three promoter constructs to drive enhanced yellow fluorescent protein (EYFP) expression in transgenic mice. Construct 1 utilized the 5 kb upstream region (FIG. 10B) plus wild type sequences encoding βIVa tubulin exon 1, intron 1, and three codons of exon2, cloned ahead of the EYFP coding region into the pEYFP-N1 vector. Construct 2 was identical to Construct 1 except that the codons 2 and 3 were mutated (Arg2Leu, Glu3Gln). This was done because the wild type sequence has a self-regulatory effect that can prematurely halt translation and promote mRNA degradation (FIG. 10B-2). In Construct 3, the non-coding sequence of exon 1 was included followed by a start codon and the EYFP sequence (FIG. 10B-3). Mice were generated at the University of Cincinnati Transgenic Facility, and tail DNA screening identified several lines carrying each transgene. By fluorescence microscopy of newborn mice, EYFP fluorescence was detected in 1/5 lines with construct 1, 3/3 lines with construct 2 and 0/5 lines with construct 3. EYFP-expressing cells were clustered in the SVZ of the lateral ventricle and had the same distrib-ution and morphology as βT4 cells observed by immunostaining (compare FIGS. 11A and B). At later ages, myelin-forming oligodendrocytes express βT4 and these cells were EYFP positive (FIG. 11C).

These data indicate the 5 kb βT4 promoter that we have cloned faithfully reproduces the cell staining patterns observed with βT4 immunostaining. Because construct 2 yielded detectable expression in 3/3 lines tested, we concluded that the modifications to the regulatory element had a beneficial effect on expression from this promoter, and this construct 2 will be used for generation of βT4-Cre-ERT2 mice. Once βT4-creERT2 44 transgenic mice are generated, they will be crossed to Z/EG double reporter mice that express EGFP following Cre-mediated recombination. These mice were provided by Dr Brain Popko47 of the University of Chicago and are currently housed in our animal facility. These mice can be utilized in our characterization of βT4 cells.

Figure 12:
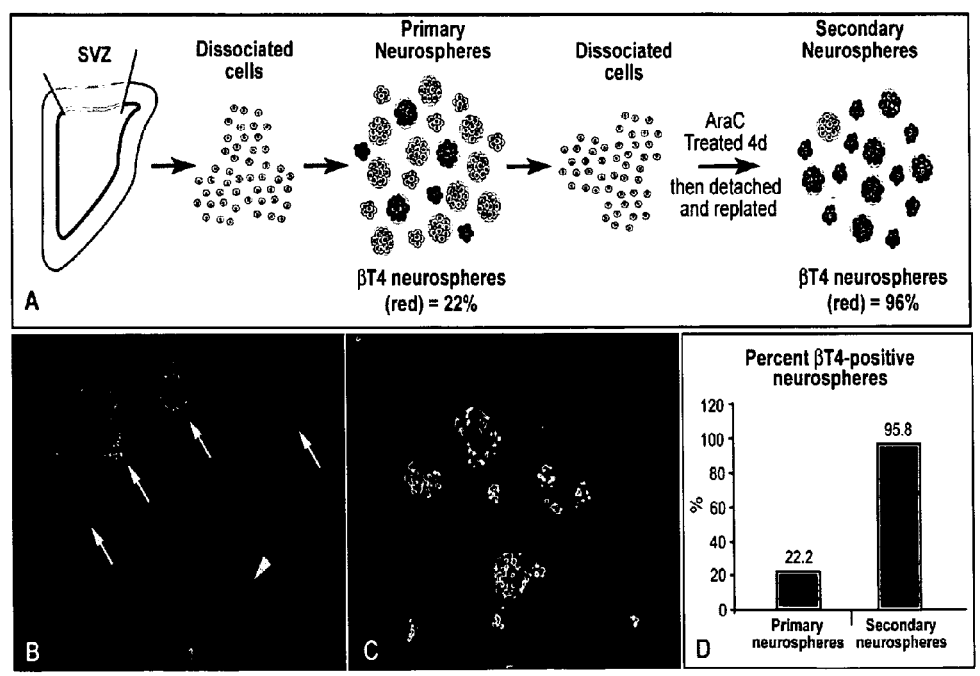
FIGS. 12(A-D) illustrate the isolation, culture and identification of βT4 cells harvested from the lateral and medial wall of the lateral ventricles from P4 rat brain. Cytosine-β-D-arabinofuranoside (Ara-C) treatment of primary neurospheres produced 96% pure βT4 cells secondary neurospheres. Our neurosphere assay procedures are described in the flow chart (FIG. 12A). The lateral ventricular walls from P4 rat are dissected into single cells and placed into neurosphere forming conditions. Primary neurospheres are attached to coverslips and stained for rβT4 (FIG. 12B) and DAPI (FIG. 12B). Neurospheres were detected by high density of nuclei (FIG. 12B). 22% of the total primary neurospheres were βT4-positive (FIG. 12B, arrowhead, and FIG. 12D). Primary neurospheres were dissociated, treated with Ara-C for 4 days and placed in neurosphere forming conditions. βT4 neurospheres represent 96% of the total secondary neurospheres (FIG. 12C, and FIG. 12D).
Figure 13:
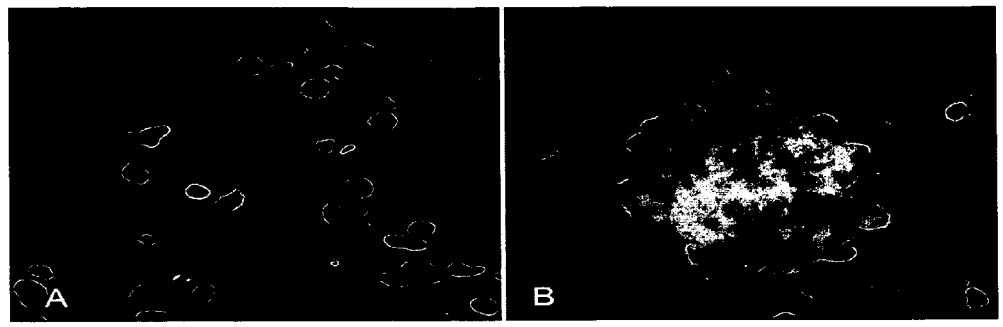
FIGS. 13(A-B) illustrate that few cells in βT4 neurospheres are BrdU-positive, but the majority are Olig2 positive. Following a 6-hour pulse with BrdU (A), only a few βT4 cells are BrdU-positive. In contrast, rapidly amplifying cells surrounding βT4 cells are intensely labeled by BrdU (A). The majority of cells in βT4 neurospheres (B) and many cells produced by βT4 neurospheres express the transcription factor Olig2 (B).

Example 5

βT4 Cells in Developing Rodent Brain
Establishment of a Neurosphere Assay System We have generated preliminary data on βT4 cell distribution during rodent brain development at E14-15 and postnatal day 4. We developed in vitro methods to study and enrich for βT4 cells. We harvested the lateral and medial wall of the lateral ventricles from P4 rat brain. As shown schematically in FIG. 12A, the tissue was dissociated into single cells and placed in neurosphere assay medium. Four days later, we attached the neurospheres to coverslips and stained for βT4. Approximately 20% of the primary neurospheres were enriched in βT4-positive cells (FIGS. 12B and D). As described above for human tissue sections, βT4 cells in primary neurospheres from neonatal rat SVZ do not express astrocytic, microglial, OPC, oligodendrocyte or neuronal markers (data not shown). βT4 cell-positive neurospheres were positive for Olig2 (FIG. 13B), a marker of precursors that give rise to oligodendrocytes and neurons. One major clue as to the possible role of βT4 cells in the SVZ came from BrdU labeling studies of primary neurospheres. In multiple experiments, only a few βT4 cells were BrdU-positive by a 20 hr BrdU pulse (FIG. 13A). Since one characteristic of multipotent stem cells is slow proliferation, this observation raised the possibility that βT4 cells were multipotent CNS stem cells. In an attempt to purify or enrich for βT4 cells, we treated P4 neurospheres (on coverslips) with cytosine-β-D-arabinofuranoside (Ara-C; for 4 days), which kills actively dividing cells. We dissociated the remaining cells and placed them in neurosphere-forming conditions for 4 days, plated the resulting neurospheres on coverslips and stained them for $β_{IV}$ tubulin. Ninety-six percent of the secondary neurospheres made from Ara-C-resistant primary neurospheres were βT4-positive (FIGS. 12C and D) and >83% of the cells in these secondary neurospheres were βT4-positive.

Figure 14:
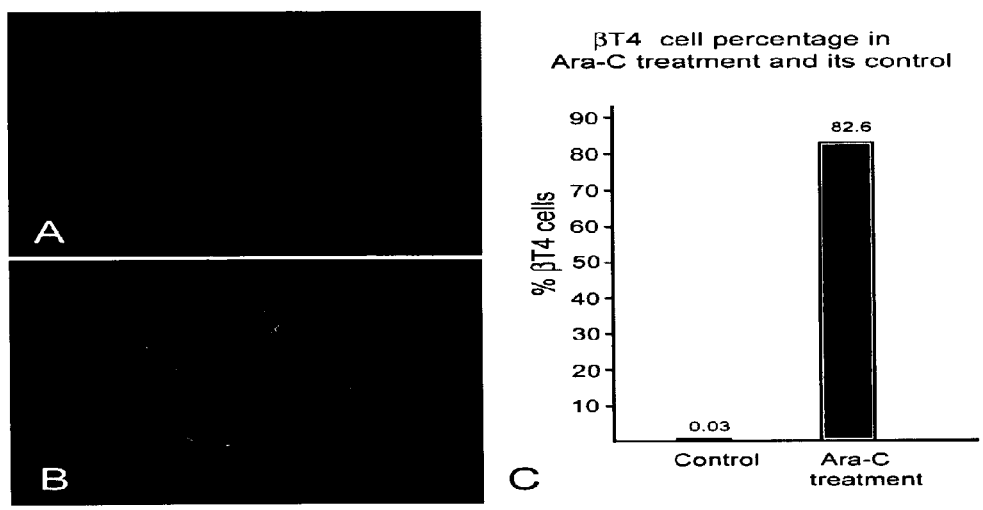
FIGS. 14(A-C) illustrate that βT4 cells are enriched after Ara-C treatment. In primary neurospheres grown on coverslips for 4 days (A), less than 1% of all cells (DAPI) were βT4-positive (C). In contrast, when grown for 4 days in Ara-C (B), over 80% of all cells were βT4-positive (C).

Dissociated primary neurosphere cells after 4 days of Ara-C treatment were >83% βT4-positive (FIG. 10C), indicating a significant enrichment from primary neurospheres without Ara-C treatment (<1% of total cells were βT4-positive; compare FIGS. 14A and B). This progression of in vitro experiments has established an assay for investigating the behavior of a highly enriched population of βT4 cells in vitro.

Figure 15:
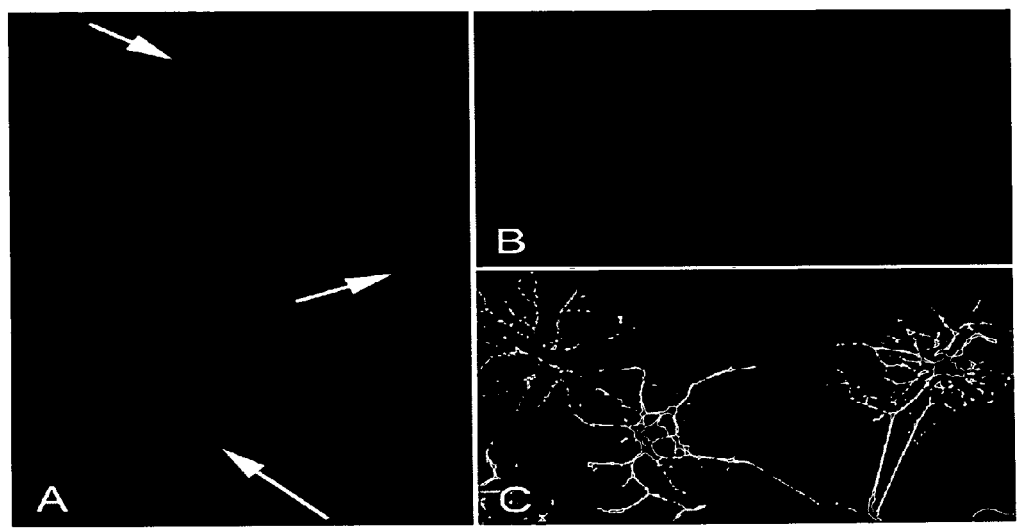
FIGS. 15(A-C) show confocal micrographs of βT4 neurospheres cultured under different growth conditions. Enriched βT4 secondary neurospheres give rise to oligodendrocytes, neurons and astrocytes. Secondary βT4 neurospheres were cultured in medium containing EGF 20 ng/ml, FGF 20 ng/ml and 1% N2 for 4-8 days. Tuj1-positive neurons (FIG. 15A), GFAP-positive astrocytes (FIG. 15B, red) and O4-positive oligodendrocytes (FIG. 15C) were detected in or near most neurospheres (shown as gray background in panel FIG. 15A, arrows).
Figure 16:
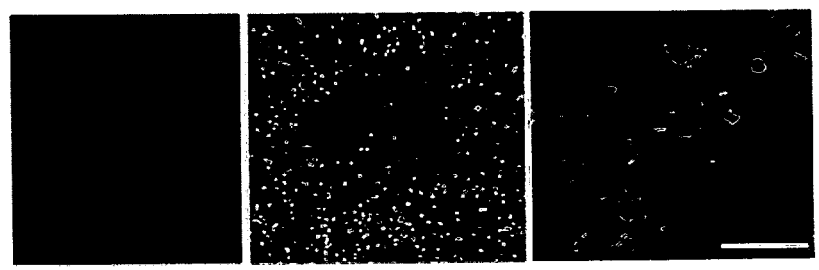
FIGS. 16(A-C) illustrate the growth and differentiation of secondary neurospheres can be modulated by growth factors. Secondary neurospheres shortly after plating onto coverslips show no outgrowth of cells (A, DAPI stain) and do not change after 4 days of culture in medium with 1% N2 supplement. Culture for the same period in the presence of N2, EGF (20 ng/ml) and FGF2 (20 ng/ml) results in outgrowth and proliferation of cells that are βT4-negative and BrdU-positive (B). Addition of Shh (1000 ng/ml) causes a marked increase in the number of neurospheres containing oligodendrocytes and neurons (C). Bar=200 μm (A, B); 50 μm (C).

The next question we asked is whether secondary, βT4-enriched neurospheres could produce mature CNS cells. We allowed them to grow in neurosphere medium for 7 days and then fixed them and stained for markers of oligodendrocytes (O4), astrocytes (GFAP) and neurons (TuJ1). All three cell types were detected in the cultures (FIG. 15). Astrocytes did appear to be the dominant cell type made, which was not surprising since these neurospheres were grown in a medium (EGF and FGF2) conducive to astrocyte differentiation. The secondary neurosphere assay provides an ideal setting for such studies. We have established baseline criteria for these assays and demonstrate feasibility of this approach. At the time of plating βT4 neurospheres are round and contain tightly packed βT4 cells (FIG. 16A). When grown in standard neurosphere medium (N2, EGF, FGF), induces a rapid expansion of secondary neurospheres identified by BrdU labeling and their migration away from the βT4 cell core (FIG. 16B).

When βT4 neurospheres are grown in N2 medium without growth factor supplement, they do not expand and retain the same appearance 4 days later (FIG. 16C). With this assay, we will determine whether growth factors or secreted products from activated immune cells affect βT4 neurosphere behavior. Using standard neurosphere medium and N2 only medium as positive and negative controls for cell growth, we tested the effects of two concentrations of sonic hedgehog on oligodendrocyte and neuron production. In the presence of FGF and EGF, the addition of Shh at 1000 ng/ml dramatically increased neuronal and oligodendrocyte production. Table 2 shows the influence of different additives on the percent of neurospheres containing TuJ1-positive neurons, O4-positive oligodendrocytes, or both.

TABLE 2

| Medium | TuJ1 | O4 | TuJ1 + O4 |
|---|---|---|---|
| N2 | — | — | — |
| N2, EGF, FGF | 28% | 58% | 19% |
| N2, EGF, FGF + Shh 500 ng/ml | 39% | 51% | 26% |
| N2, EGF, FGF + Shh 100 ng/ml | 97% | 100% | 97% |

This pilot experiment shows that the phenotype of cells produced by βT4 neurospheres can be modulated by growth factors.

Example 6

Location of βT4 Cells in Developing Rodent Brain and Their Ability to Produce Neurospheres The purpose of this experiment is to investigate the role of βT4 cells during rat brain development. Rat tissue is used because we can enrich for and study βT4 cells using a combination of neurosphere and tissue culture techniques. Gliogenesis occurs in two general waves in the telencephalon of the developing rodent brain. An early wave of progenitor cells is generated in the medial ganglionic eminence (MGE) at E13-15, and these cells migrate to select regions of the telencephalon. These progenitor cells express PDGFRα, NG2, and mRNA encoding PLP/DM20 and they can be followed in tissue slices in transgenic mice expressing EGFP behind the PLP/DM20 promoter. These MGE-derived progenitor cells produce telencephalic GABAergic interneurons and then oligodendrocytes. The cell or cells that produce this wave of progenitors are unknown. A second wave of telencephalic progenitor cells originate from the SVZ of the lateral ventricles during late fetal and early postnatal brain development. These progenitor cells express NG2, PDGFRα, Dlx2 and Mash1.

We hypothesize that the developmental appearance of βT4 cells correlates with the second wave of gliogenesis that occurs in late fetal and early postnatal rat brains. To test this hypothesis, the immunocytochemical distribution of βT4 cells during fetal and early postnatal development is first determined and, then, the requirement for βT4 cell detection for the generation of neurospheres in vitro is determined. Cells are dissociated from E10-11 telencephalon (when projection neurons are generated), E13-14 medial ganglionic eminence (first wave of glial progenitors) and P4, P21, and P60 lateral ventricle (late wave and mature brain). βT4 cells are present in P4 and P60 lateral ventricle SVZ and when both regions are dissociated, they produce βT4 cell neurospheres. The in vitro studies follow the paradigm shown in FIG. 9A. Cells are removed from appropriate areas, enzymatically and mechanically dissociated, placed in neurosphere-forming media for four days, plated on coverslips, and the percentage of neurospheres containing βT4 cells determined by immunocytochemistry. Parallel primary neurospheres on coverslips are treated for four days with Ara-C, dissociated into single cells, placed in neurosphere-forming culture for four days, plated on coverslips and then stained with tubulin βIV antibodies. The total number of secondary neurospheres and what percentage is βT4 cell-enriched is then determined.

The possibility that βT4 cells are multipotential CNS stem cells is supported by the enrichment of βT4 cells in secondary neurospheres following Ara-C treatment. A universal characteristic of multipotential stem cells is their slow rate of division. Our preliminary data supports the possibility that the non-βT4 neurospheres, which represented 78% of primary neurospheres produced from P4 lateral ventricle SVZ, were generated from rapidly dividing transit amplifying or early progenitor cells. To determine if secondary βT4 neurospheres can produce cells that form non-βT4 neurospheres, secondary βT4 neurospheres (formed after Ara-C treatment) are propagated on coverslips for 24 hrs. These cultures are then dissociated into single cells and placed into neurosphere forming conditions for 4 days. The resulting neurospheres are attached to the coverslips, and the percentage of neurospheres that are βT4-positive is determined. If βT4 cells produce transit amplifying or early progenitor cells capable of producing neurospheres, the majority of neurospheres generated should be βT4-negative, possibly at percentages (80%) seen in primary neurospheres.

Materials and Methods
Immunocytochemical Distribution of Rat βT4 Cells

4% paraformaldehyde-fixed and free-floating sections of fetal and early postnatal rat brain is used to determine the distribution of βT4 cells. Fetuses are obtained from timed pregnant Sprague-Dawley rats at embryonic days 10-11, 13-14, 18-19, and postnatal days 0, 4, 21 and 60. Sections are stained with βIV tubulin antibodies. Other molecules that may be expressed by βT4 cells are then characterized.

Primary Neurospheres

Neurospheres are generated from embryonic and early postnatal Sprague Dawley rats using established protocols approved by our Institutional Animal Care and Use Committee. Neurospheres are generated from E10-11 telencephalon, E13-14 MGE, and E18-19, P0, P4, P21 and P60 lateral ventricle. If the results of the immunocytochemical experiments described above find other SVZ areas highly enriched for βT4 cells, they are included in this experiment. The method for generating neurospheres described here is for P4 lateral ventricles. The lateral ventricular zone is isolated from coronal sections, then finely minced, trypsin- and DNase-treated, and then filtered, washed, pelleted, and dissociated into a suspension solution. The dissociated cell suspension ($10^5$ cells/ml) is placed in un-coated T-75 flasks in neurosphere-permissive solution (20 ng/ml EGF, 20 ng/ml FGF, and 1% N2 supplement in DMEM/F12 media) and cultured for 4 days. Primary neurospheres are then visible and transferred to Poly-L-Lysine-coated coverslips, allowed to attach for 15 min, fixed with 4% paraformaldehyde for 30 min, pretreated with 0.1% triton-X100/PBS for 20 min and then stained by βIV tubulin antibodies. The total number of neurospheres and the percentage enriched in βT4 cells is then determined.

Secondary Neurospheres

Primary neurospheres are generated as described above, dissociated with trypsin and trituration, and then plated onto Poly-L-Lysine-coated coverslips. The coverslips are then incubated with Ara-C (10 μM Ara-C, 10 ng/mL EGF, 10 ng/mL FGF, 1% N2 in DMEM/F12) for 4 days, placed in T-75 flasks containing neurosphere-permissive medium, and allowed to grow for 3 days. These secondary neurospheres are then plated onto coverslips for 2 hrs, fixed in 4% paraformaldehyde and stained for DIV tubulin. The percentage of βT4-enriched neurospheres are then determined (3 coverslips each from three different preparations) for each brain area (E10-11 telencephalon, E13-14 MGE, and P4, P21 and P60 lateral ventricle).

To determine if βT4-enriched secondary neurospheres can produce non-βT4 neurospheres, βT4-enriched neurospheres are generated as described above, plated on coverslips and allowed to grow for 24 hrs. These cells are then detached, dissociated and placed in T-75 flasks for 3-4 days to grow a third generation of neurospheres. These neurospheres are plated on coverslips and stained for βT4 as described above. The percentage of βT4-negative neurospheres is then determined.

Example 7

βT4 Cells Contribute to Postnatal Myelination and What Regulates the Process

The purpose of this Example is to investigate the role of βT4 cells during rat brain development. Gliogenesis occurs in two general waves in the telencephalon of the developing rodent brain. An early wave of progenitor cells is generated in the medial ganglionic eminence (MGE) at E13-15, and these cells migrate to select regions of the telencephalon. These progenitor cells express PDGFRα, NG2, and mRNA encoding PLP/DM20 and they can be followed in tissue slices in transgenic mice expressing EGFP behind the PLP/DM20 promoter. These MGE-derived progenitor cells produce telencephalic GABAergic interneurons and then oligodendrocytes. The cell or cells that produce this wave of progenitors are unknown. A second wave of telencephalic progenitor cells originate from the SVZ of the lateral ventricles during late fetal and early postnatal brain development. These progenitor cells express NG2, PDGFRα, Dlx2 and Mash1. We hypothesize that the developmental appearance of βT4 cells will correlate with the second wave of gliogenesis that occurs in late fetal and early postnatal rat brains.

βT4 Cells Produce Oligodendrocyte Lineage Cells During Postnatal Development

Figure 7:
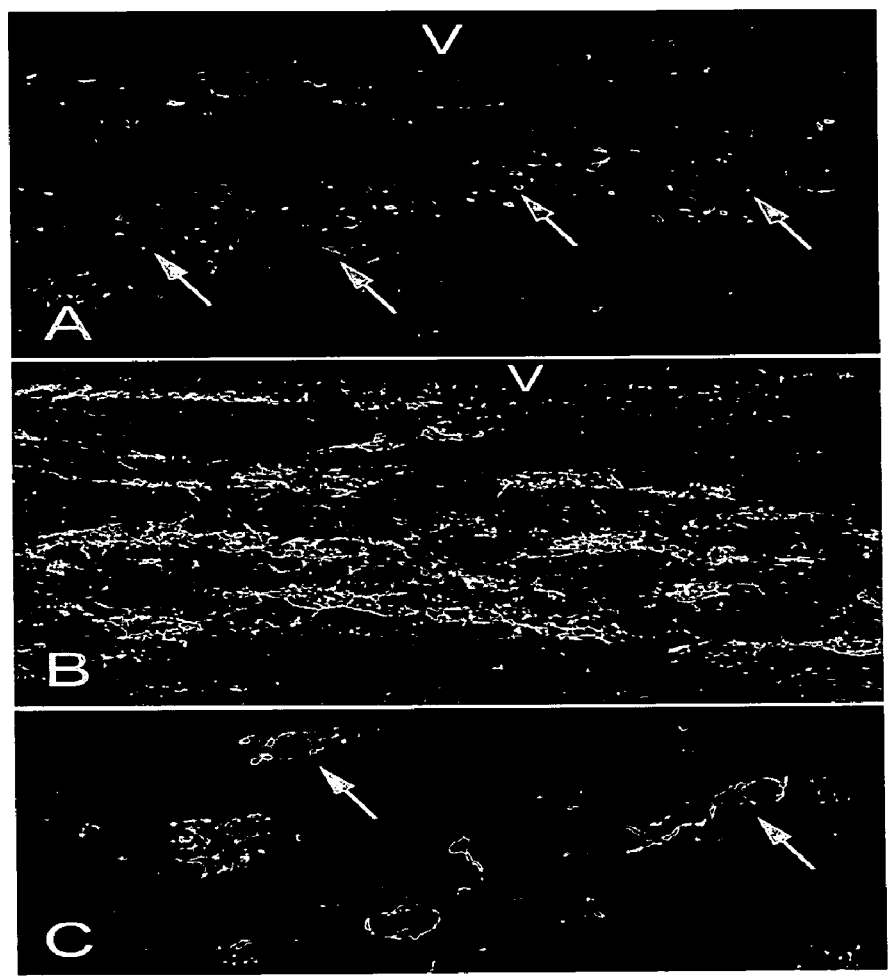
FIGS. 7(A-C) show confocal micrographs of a periventricular MS lesion labeled with βIV tubulin (FIGS. 7A-B), glial fibrillary acidic protein (GFAP) (FIG. 7A) and Olig2 (FIG. 7B). βT4 cells in the SVZ are different from other adult precursor cells previously described. They are negative for GFAP, but often positive for Olig2. βIV tubulin (FIG. 7C) and Olig2 (FIG. 7C) are also expressed on mature oligodendrocytes (FIG. 7C, arrows) in normal appearing white matter surrounding the lesion.

We will follow the progeny of SVZ βT4 Cells Using Cre-LoxP technology. We have isolated a 5 Kb promoter of the tubulin $β_{IVa}$ gene that faithfully expresses a reporter gene during mouse brain development (FIG. 7). We will use this promoter to express Cre recombinase in SVZ βT4 cells. The Cre construct will contain a fusion protein ($ER^{T2}$), which is stimulated by low concentrations of tamoxifen, but not estradiol. These mice will be crossed with the Z/EG double reporter mouse. To trace the progeny of βT4 cells, tamoxifen will be administered to double transgenic mice (βT4-Cre $ER^{T2}$/Z/EG). This will cause expression of EGFP in all cells that express tubulin $β_{IVa}$ and all cells derived from these cells.

In order to follow SVZ βT4 cell lineage specifically, we will focus upon examining various time points following tamoxifen administration at 1-2 weeks post conception. At this age, the only cell expressing tubulin βIVa is the SVZ βT4 cell. If these cells generate oligodendrocyte lineage cells, their progeny should be present in the forebrain at 4 weeks of age, a time point at which the forebrain is maximally populated with premyelinating and myelinating oligodendrocytes. Accordingly, examination of time points between 1-2 and 4 weeks post conception will reveal the tempo of development of individual cells along this lineage during the onset and peak of myelination in the forebrain. We will focus upon the cerebral cortex because we have previously demonstrated that oligodendrocyte lineage cells in this region display a spatial and temporal progression in differentiation and maturation. Retroviral labeling studies have demonstrated that the cells within the 0-1 weeks post conception SVZ achieve extensive migration and morphologic differentiation within one week. Retroviruses are preferentially incorporated into rapidly dividing cells, which most likely correspond to transit amplifying cells. There is little known about the period of maturation from a quiescent stem cell to a transit amplifying cell.

We have shown that βT4 immunoreactivity appears in oligodendrocytes of the corpus callosum at 4-5 post conception and is most intense at 8-10 weeks post conception. Thus, administration of tamoxifen at 7-10 weeks post conception will label both SVZ βT4 cells and oligodendrocytes. Examination of double transgenic mice treated with tamoxifen at both of these time points are necessary to confirm appropriate regulation of expression from the βT4-Cre $ER^{T2}$ construct and efficient recombination and reporter gene (EGFP) expression.

Expression of EGFP by the progeny of the SVZ βT4 cells enables us to characterize the morphology of the cells without additional histochemical manipulations. We will perform immunocytochemical phenotyping based upon the shape and location of EGFP-positive cells. Obvious cells and antigens include stem cells (βIV tubulin, Olig2 and other transcription factors), transit amplifying cells (transcription factors), OPC's (NG2, PDGFRα), and premyelinating and myelinating oligodendrocytes (PLP). We will also examine older animals, e.g., >three months of age. Such studies will permit us to assess changes in number and location of SVZ βT4 cells in the mature animal and provide baseline data for future studies of demyelination models.

Methods

The 5 Kb sequence upstream of the gene encoding the tubulin βIva isoform (Tubb4, Chromosome 17) will be cloned into the tamoxifen-dependent Cre recombinase vector, pCre-$ER^{T2}$. The efficacy of the resulting fusion protein will be tested by transfection into a reporter cell line. Transgenic mice will be generated at the University of Cincinnati Transgenic Facility and founder animals identified by analysis of tail DNA. βT4-CreER$^{T2}$ transgenic lines will be screened for Cre expression by RT-PCR and several hemizygous transgenic mouse lines will be used for matings with Z/EG double reporter transgenic mice. This mouse carries a transgene that utilizes the chicken beta actin promoter with upstream CMV enhancer elements, a loxP-flanked βgeo (lacZ and neomycin-resistance) fusion gene, three copies of the SV40 polyadenylation sequence and enhanced green fluorescent protein (EGFP). In the absence of Cre, βgeo is expressed, while in the presence of Cre, the floxed sequences are excised, and EGFP is expressed. Therefore, the cells that have undergone Cre-mediated recombination can be detected without additional histochemical detection methods.

Expression of Cre recombinase and activation of EGFP reporter will be achieved by a single oral gavage of tamoxifen (0.11 mg/g body weight, Sigma T-5648 diluted in corn oil (Sigma C-8267)). As noted above, tamoxifen will be administered to separate groups of animals at 1-2 weeks and 7-10 weeks post conception. Previous studies have shown that nuclear localization of Cre first appears 6 hours after administration and declines at ~30 hours. Double fluorescence studies (EGFP and immunohistochemistry for βT4) will be performed 24, 48 and 72 hours post-tamoxifen to assess veracity of Cre expression and efficiency and timing of recombination. Lineage tracing studies will utilize animals given tamoxifen at P1-2. We will perform pilot studies of EGFP expression on a small number of animals to determine the most informative specific time points, followed by detailed immunohistochemical examination of cohorts of animals. We anticipate detailed analysis of up to four time points in animals less than 4 weeks old and two time points for animals greater than 3 months of age. Animals will be sacrificed by intracardiac perfusion with 4% paraformaldehyde and sections prepared for analysis by methods developed in our laboratory to specifically follow oligodendrocyte lineage in rodents. Immunohistochemical analyses will utilize specific antibodies based upon the morphology and spatial distribution of the EGFP labeled cells. Antibodies will include βT4, Olig1/2, Dlx2, Mash1, Nkx2.2, NG2, PLP, GFAP, TuJ1, and NeuN. This panel will characterize putative transit amplifying cells as well as the major neuroectodermal lineages.

The use of Cre/loxP technology for lineage tracing in the central nervous system has been validated using a number of developmentally regulated promoters. In view of our preliminary findings on the ability of the Tubb4 promoter to drive expression of a YFP reporter into the appropriate βT4 expressing cells, we anticipate that this promoter will also drive Cre expression in a similar population of cells. It remains possible that the absolute number of cells expressing the reporter in the βT4-CreER$^{T2}$+Z/EG bigenic mice may be less than the total number of βT4 expressing cells due to inefficiencies in tamoxifen mediated nuclear translocation of Cre or in Cre-mediated recombination. However, because the purpose of these experiments is fate mapping, 100% efficiency in marking the cells is not necessary as long as the population of cells that undergoes recombination is representative of the total population of cells in which the βT4 promoter is active. In addition, the efficiency of recombination can be maximized by modulating the tamoxifen administration protocol. While unlikely based upon our 33T4-EYFP mice, it is also possible that there may be ectopic expression of Cre. This would lead to expression of the EFGP reporter in cells where the βT4 promoter is not normally active. This will be identified by fluorescence microscopy for EGFP and βT4 immunolabeling of brain sections at early time points. If this is the case, alternative rβT4 promoter/Cre constructs will be developed. For example, studies utilizing BACs to place CRE under the control of endogenous promoters has resulted in much tighter regulation of Cre expression. Since the tubulin $β_{IVa}$ (Tubb4) gene is relatively small (~7 kb), CRE can be directly introduced into BACs containing Tubb4 via standard BAC mutagenesis protocols.

βT4 Cell Expression of Novel Signaling Molecules

It is essential to characterize other molecules enriched in βT4 cells. To achieve this goal, we will perform an unbiased characterization of genes expressed by secondary neurospheres using microarray technology. Since over 83% of the cells in these neurospheres are βT4-positive, we will obtain a molecular profile of βT4 cells. We will use standard protocols established in the laboratory to quantify and classify gene transcripts into functional categories. A minimum of three separate array profiles will be obtained. To help establish whether genes are enriched in βT4 cells, we will compare these gene profiles with those obtained from microarray analysis of primary neurospheres. Molecules of interest will be localized immunocytochemically in secondary neurospheres and in developing mouse and human brain and in MS brains.

Methods

Total RNA will be isolated using the Picopure RNA isolation kit from Arcturus (CA) and run on the Agilent Bioanalyzer 2100 (Paulo Alto Calif., USA) for quality assessment. Five separate comparisons will be performed. Multiple secondary neurosphere preparations will be pooled for each analysis. Each sample will be labeled according to the Affymetrix eukaryotic small sample protocol. Briefly, a T7-(dT)24 primer is used to synthesize unlabeled cRNA. The cRNA is cleaned and used for a second round of amplification using biotinylated ribonucleotides. The labeled cRNA is purified and fragmented to 35-200 bp sizes for effective hybridization, which is assessed by hybridization to a Test 3 Genechip probe array. Affymetrix's recommended criteria for using a labeled target for hybridization is as follows: (1) the ratio of the signal generated that corresponds to the 3' region of a gene compared with the 5' signal needs to be less than 3:1 for β-actin and GAPDH; (2) the background is less than 700; (3) the noise is less than 10. Samples which pass the filtration criteria will be hybridized to the Rat U230 arrays, which contain 30,000 probe sets, and 28,000 known genes. Since false positive signals originate from genes expressed at low levels, we employ filtration criteria to remove all 'absent call probe sets'. Arrays will be analyzed using Affymetrix Microarray Suite 5.0 (MAS5.0) and GeneSpring 5.0 software from Silicone Genetics. Outliers will be eliminated using principle component analysis and univariate analysis. The Global Error Model in GeneSpring 5.0 performs variance component analysis to estimate standard errors and compare mean expression levels between experimental conditions. We will use 'Per Chip' normalizations that control for chip-wide variations in intensity and 'Per Gene' normalization (normalization to median) that accounts for the difference in detection efficiency between spots. Expression levels of genes in primary and secondary neurospheres will be compared using the unpaired T-test. To create further stringency and reliability of the results, Benjamini-Hochberg False Discovery rate (FDR) correction will be applied. All transcripts differentially expressed at $p<0.05$ passing the FDR correction will be classified into biologically meaningful groups based on gene ontology classification using EASE and pathway explorer programs. Expression levels and cellular distribution of the resultant transcripts will be verified by real time PCR (Roche Lightcycler, Roche USA) Western blots and immunohistochemistry. Comparative mapping of the transcripts will be done to find human transcripts corresponding to the rat genes. These genes will finally be compared for their expression and distribution in the human SVZ region.

Regulation of βT4 Cell Development

We will investigate the behavior and fate of βT4 cells in secondary neurospheres. These studies will characterize the growth factors that modulate βT4 cell number, transit amplifying cell phenotype or number, or lineage-committed progenitor cells produced by βT4 neurospheres. The ability to enrich for βT4 cells using the anti-metabolite Ara-C after neurosphere formation offers the opportunity to characterize and manipulate βT4 cells, the transit amplifying cell population derived from βT4 neurospheres, and the external factors that drive βT4 neurospheres to produce oligodendrocyte progenitor cells. Several growth factors can modulate specification of oligodendrocyte lineage in vivo and in vitro. Preliminary data indicates that βT4 cells are slowly dividing multipotential CNS stem cells, yielding TuJ1-positive neurons, O4-positive oligodendrocytes, and GFAP-positive astrocytes. As such, βT4 neurospheres should respond to growth factors that are known to control or modulate lineage specification.

Our preliminary experiments have documented the relative quiescence of the βT4 cells, determined by sparse BrdU labeling and by their resistance to the anti-mitotic agent, Ara-C. The expansion of neurospheres after Ara-C treatment indicates, however, that βT4 neurospheres produce a rapidly dividing cell, which generates progenitor cells that in turn have the ability to produce neurons, astrocytes and oligodendrocytes. To date, no markers have been identified which occur specifically and uniquely in all transit amplifying cells that produce glial progenitor cells. The transcription factors, Mash1, Dlx2, Nkx2.2 and Olig1/2, have been identified in rapidly dividing cells within the SVZ and in cells committed to the oligodendrocyte lineage. While not unique to the transit amplifying cells, these transcription factors currently offer the best chance for defining this intermediate, rapidly dividing cell population. βT4 cells are Olig2-positive (FIG. 13) but initially negative for progenitor cell markers (NG2, PDGFRα, PSA-NCAM, and O4). After Ara-C treatment, neurospheres will receive continuous BrdU treatment prior to fixation at 6, 12, 24 36 and 48 hours. Cultures will be stained for BrdU, transcription factors, and surface markers of OPCs. These experiments will allow us to determine the time frame in which βT4 neurospheres/cells produce rapidly dividing cells and how quickly markers of transit amplifying cells are turned on. We will determine how long it takes for committed progenitors to be specified. At 2, 4, and 7 days in vitro, we will also stain secondary neurospheres for the OPC markers NG2 and PDGFRα and for oligodendrocytes (PLP), neurons (TuJ1) and astrocytes (GFAP). Initially, these experiments will be performed in standard neurosphere medium (N2, PDGF and FGF). Our goal is to determine whether these growth factors affect βT4 cells, transit amplifying cells or committed progenitor cells. We will examine the effects of each of these factors on βT4 neurospheres, enriched after Ara-C treatment, using BrdU and markers for transit amplifying cells and lineage-committed progenitors, as described above. This will allow us to follow the effect of these growth factors on all three cell populations and determine if transit amplifying cell or committed progenitor cell phenotypes are altered. Since the last submission two observations have increased our interest in the role of Shh in βT4 cell behavior.

We will test each growth factor in N2 medium and Shh and BMP will be tested in combination with FGF and/or EGF.

Methods

Primary Neurospheres

Neurospheres will be generated from early postnatal Sprague Dawley rats using established protocols approved by our Institutional Animal Care and Use Committee. The lateral ventricular zone is isolated from coronal sections, then finely minced, trypsin- and DNase-treated, and then filtered, washed, pelleted, and dissociated into a suspension solution. The dissociated cell suspension (10 cells/ml) is placed in un-coated T-75 flasks in neurosphere-permissive solution (20 ng/ml EGF, 20 ng/ml FGF, and 1% N2 supplement in DMEM/F12 media) and cultured for 4 days.

Secondary Neurospheres

Primary neurospheres are generated as described above, dissociated with trypsin and trituration, and then plated onto Poly-L-Lysine-coated coverslips. The coverslips are then incubated with Ara-C (10 μM Ara-C, 10 ng/mL EGF, 10 ng/mL FGF, 1% N2 in DMEM/F12) for 4 days, placed in T-75 flasks containing neurosphere-permissive medium, and allowed to grow for 3 days. These secondary neurospheres are then plated onto coverslips various periods of time, fixed in 4% paraformaldehyde and immunophenotyped.

Growth Factor Studies

Secondary neurospheres will be generated from P4 rat brain. We will determine if the βT4 cells, or the phenotype or number of transit amplifying cells, are affected when Shh (0-250 ng/ml) BMP4 (0-1000 ng/ml), FGF2 (0-50 ng/ml) or EGF (0-100 ng/ml) are added to our basic culture medium (DMEM/F12 plus N2). We will determine if these growth factors affect βT4 cell number, transit amplifying cell number, or transit amplifying cell phenotype, by performing double-labeling immunocytochemistry for transcription factors described above and BrdU (time points described below). If any of the factors are observed to increase proliferation but suppress differentiation, then combinations of factors will be tested using concentrations determined to be suitable in the preceding experiments. If it is observed that BMP4 inhibits generation of oligodendrocyte progenitors, then the BMP inhibitor noggin will also be tested.

Immunocytochemistry

Ara-C-treated secondary neurospheres will be plated on coverslips with the various mediums described above. Initial studies will quantify and phenotype transit amplifying cells at 6, 12, 24, 36 and 48 hrs. Each coverslip will receive a 6 hr pulse of 10 μM BrdU prior to fixation with 4% paraformaldehyde. The tissue will be double-labeled for BrdU and the transcription factors Olig1, Olig2, Nkx2.2, Mash1 and Dlx2. These antibody combinations should establish a phenotype of the transit amplifying cells produced by βT4-enriched neurospheres. We will quantify the total number of BrdU-positive cells and the percentage of total and BrdU-positive cells that express individual transcription factors. We anticipate that not all growth factor concentrations and transcription factor combinations will be necessary. These studies will establish the growth factor requirements for producing various transit amplifying cell phenotypes. We will extend our analysis to later time points (7, 10 and 14 days) to study the production of cells committed to oligodendrocyte lineage using antibodies to NG2, O4 and PLP.

We have recently discovered that Shh significantly increases the number of oligodendrocytes and neurons in secondary neurospheres. We will identify whether this affect is on βT4 cells, transient amplifying cells of committed progenitor cells. To further study the actions of Shh, cyclopamine will be added to the Shh-treated neurospheres. Cyclopamine addition should inhibit effects directly induced by Shh. BMP may inhibit βT4 cell proliferation, transient amplifying cell division, or OPC generation. BMP affects may repress Olig2, and this effect should be reversible with the addition of noggin. FGF and EGF are both known to be mitogenic to stem and/or transit amplifying cells, in which case we expect an increase in the number of BrdU-positive cells. If an increase in the number of OPCs is seen upon addition of FGF2, then PD173074, which blocks the FGF2 receptor, can be used to confirm the requirement of these cells for FGF2. An FGF2-dependent oligodendrocyte lineage has recently been described, and it is possible that the βT4 cells contribute to this lineage. Addition of EGF to the βT4 neurospheres will most likely increase the proliferation of transit amplifying cells. The microarray analysis is designed to identify signaling molecules highly expressed in βT4 cells. We anticipate therefore that this analysis may identify receptors for other ligands that regulate cell differentiation. If confirmation studies demonstrate that receptors and their downstream signaling molecules are expressed by βT4 cells, we will design appropriate in vitro paradigms to test their affects on secondary neurospheres.

Example 8

Activation of βT4 Cells in the SVZ by Demylenation

The initial observation that sparked our interest in βT4 cells was their detection in SVZs of periventricular MS lesions. Preliminary data (FIG. 8) suggest that βT4 cells are increased in SVZs of MS lesions when compared to non-lesion areas in the same sections. While these data suggest that βT4 cell density is increased in response to demyelination, the timing and functional significance of βT4 cell increase during demyelination can only be inferred from characterization of fixed autopsy tissue. The purpose of this experiment is to determine if SVZ βT4 cells are increased following demyelination in the adult rat brain. We will use Cre-Lox P technology in mice to induce EGFP reporter expression, thereby labeling the progeny of βT4 cells, and allowing us to determine their role in repair of demyelination induced by lysolecithin or experimental autoimmune encephalomyelitis (EAE).

Lysolecithin

To examine the process of remyelination following non-immune-mediated demyelination, we will use the model of microinjecting lysolecithin into the cingulum of P60 mouse brain. Demyelination and remyelination is highly reproducible and these events occur in a timely manner. Axons are demyelinated by 7 days post-injection and new oligodendrocytes begin to appear three days later. Many demyelinated axons are surrounded by thin myelin sheaths two weeks post injection and remyelination is extensive 28 days post injection. As described above, we hypothesize that the demyelinated environment will "activate" βT4 cells and that these cells will serve as a source of OPCs needed for remyelination. It has been established that OPCs migrate into toxin induced demyelinated lesions. Two potential sources of these OPCs have been identified. Progenitor cells from the rostral migratory stream (RMS) and SVZ can be diverted into the lesion. We have chosen a site for demyelination that is quite distant from the RMS, so it is unlikely that these cells will contribute to lesion repair. The phenotype of the cell that produces these SVZ-derived progenitor cells is unknown. We will activate expression of βT4 driven EGFP by administrating tamoxifen after lysolecithin injection. We will phenotype the EGFP positive cells using double labeling immunocytochemistry with a focus on SVZ cells (βIV tubulin and transcription factors), OPCs (NG2), and premyelinating and remyelinating oligodendrocytes (PLP). These experiments will directly test the hypothesis that demyelination activates βT4 cells to produce transit amplifying cells, OPCs, and new oligodendrocytes.

EAE

Immune-mediated demyelination (EAE) will be induced in 8-10 week old female Cre-Lox P mice using $MOG_{35\text{-}55}$ peptides. Cre-lox mice will be generated in a background (C57BL/6) that demonstrates consistent demyelination in the corpus callosum when immunized with $MOG_{35\text{-}55}$ peptide in complete Freund's adjuvant. Neurobehavioral signs of EAE begin between day 12 and 17. At the onset of EAE, we will administer tamoxifen in a single dose that does not affect the severity of EAE. Mice will be sacrificed at varying times after onset of EAE: 5 days after onset (worsening phase of attack); 10 days after onset (plateau phase of attack); 20 days after onset (recovery phase of attack); and 30 days after onset (resolution phase of attack, with stable neurological deficit). To label dividing cells EAE mice will receive three i.p. injections of BrdU six hrs apart prior to sacrifice. While this protocol has labeled SVZ and OPC cells in the same model, we will empirically determine timing of additional BrdU administrations based on activation of EGFP in the SVZ. We will then phenotype EGFP-positive cells. Previous studies have identified remyelination 20 days after EAE onset. Analysis will follow that described for the lysolecithin studies. The comparison of these two models should allow us to distinguish whether immune-mediated inflammation associated with demyelination in EAE has an effect on βT4 cell behavior.

One of the unresolved questions in the activation of SVZ cells in response to demyelination in MS brains is the molecular mechanisms that initiate the process. It is feasible that inflammatory mediators play a role in activating βT4 cells. To test this possibility, we will produce secondary neurospheres from adult Cre-loxP mice and test the effect of various cytokines on their behavior. We will test supernatants derived from the SVZ of EAE mice (collected when SVZ βT4 cells are maximally activated). We will also test supernatants produced by myelin-antigen activated T cells, interferon (IFN)-γ-activated astrocytes and LPS activated microglia. We will determine if secondary neurospheres produce more cells in response to these conditioned media. We have developed an in vitro screening protocol for testing a library of 30,000 small molecules on primary neurospheres. This project is funded as part of a Collaborative Research Center of The National MS Society. We use a dye binding assay to quantify cell numbers in multi-well plates. When we get a hit we will establish a standard curve effect using different concentrations of conditioned medium. Once a maximal and reproducible response is established, we will phenotype the new cells and begin to isolate the molecule or molecules responsible for activating the βT4 cells. This analysis begins with molecular weight cuts using commercial columns. If activity is identified, we will test candidate proteins in the defined molecular weight range (this is how CXCL1 was identified). If this approach is not successful, we will identify molecules by gel electrophoresis and mass spectrometry. This is the approach we used to identify $β_{IV}$ tubulin as the antigen reacting with Tie 2 antibodies.

Materials and Methods

Toxin Induced Demyelination

Lysolecithin will be introduced stereotactically into 3-4-month old female Cre-Lox P mice as described previously. 2 µL of lysolecithin (1% solution; or sterile saline for control animals) will be introduced into the sub-cortical white matter—cingulum and corpus callosum—at the co-ordinates 1.1 mm posterior to Bregma, 1.0 mm lateral to Bregma, and 2.8 mm deep, through small holes drilled in the skull. Lysolecithin or saline will be injected at a rate of 1 µL/min using a 10 µL fixed-needle Hamilton syringe. The syringe will be left in place for 4 minutes to allow the injected solutions and tissue to equilibrate and the injection site filled with absorbable gel foam prior to suturing. Tamoxifen will be administered immediately following lysolecithin injections. Animals will be sacrificed at 2, 4, 7, 10, 14 and 28 days post-injection by intracardiac perfusion with 4% paraformaldehyde.

EAE

EAE will be induced in 8-10 week-old female Cre/loxP C57BL/6 transgenic mice using a previously described protocol that activated SVZ cells to migrate into demyelinated lesions and is well established in the lab of our colleague Dr. Ransohoff. Briefly, mice are immunized subcutaneously with 200 µg of a HPLC-purified peptide representing residues 35-55 of rat MOG (MEVGWYRSPFSRVVHLYRNGK; (SEQ ID NO: 16) BIO-SYNTHESIS), emulsified in incomplete Freund's adjuvant (IFA; Difco) supplemented with 400 µg of heat inactivated *Mycobacterium tuberculosis* (H37Ra). Mice also receive pertusis toxin (PT) i.v. at the time of immunization (200 ng) and 48 hrs later (200 ng). Mice are weighed and tested neurologically (1-5 scale) each day using methods previously established in the lab. Mice reaching a severity score of 4 will be humanely sacrificed if unable to maintain hydration. Mice will receive 3 ip injections of BrdU (60 mg/kg) 6 hrs apart at 10, 20 and 30 days post immunization and then sacrificed for analysis.

Immunocytochemistry

Paraformaldehyde-fixed brains will be cryoprotected, 30 µm free-floating sections will be cut on a freezing microtome, and sections including SVZ and lesion will be analyzed in a confocal microscope for EGFP and tubulin $β_{IV}$ (βT4 cells), the transcription factors Olig1/2, Dlx2, Mash1, and Nkx2.2 (transit amplifying cells), NG2 (OPC's) and PLP (premyelinating and myelinating oligodendrocytes). Demyelination, OPC distribution and remyelination will be characterized using standard immunocytochemical analysis of myelin proteins (PLP and MOG) and OPC surface antigens (NG2 and PDGFRα). We will also determine if cells committed to astrocytic (GFAP) or neuronal lineages (TuJ1) are EGFP-positive.

Immune Modulators Conditioned Medium from Encephalitogenic T Cells

Mice aged 8-10 weeks are immunized to induce EAE, as described above. Seven days post-immunization, draining lymph node cells isolated from $MOG_{35\text{-}55}$ immunized mice ($5\times10^5$/ml) were incubated in a 24-well plate in RPMI1640 supplemented with 10% FBS (Gibco-BRL), 2 mM L-glutamine, 1 mM sodium pyruvate, 100 IU/ml penicillin/streptomycin and $2\times10$ M 2-mercaptoethanol (Gibco-BRL) with the $MOG_{35\text{-}55}$ peptide immunogen (20 µg/ml) for 72 h. Supernatant are collected and used as lymphocyte conditioned medium for assay on secondary neurospheres.

Astrocyte Conditioned Medium (CM)

The process of culturing astrocytes is activating and the cells express a reactive astrocyte phenotype. CM from astrocyte explants will be prepared as described. In some experiments, astrocytes will be further stimulated with murine IFN-γ (R&D), at a concentration of 100 U/mL for 48 hrs, followed by washing to remove cytokine, and preparation of CM.

Microglial Conditioned Medium Following Activation In Vivo with LPS:

This protocol is in routine use in the lab. Mice are injected daily for 4 days with LPS (Sigma; 20 µg in 100 µl PBS) intraperitoneally (i.p.). Four hrs after final injection, animals are anesthetized with Nembutal and perfused through the left ventricle (HBSS without $Ca^{++}/Mg^{++}$) and brains are collected in 10 ml HBSS/brain containing 0.05% collagenase D (Roche, Indianapolis, Ind.), 0.1 µg/ml TLCK (Sigma), 10 µg/ml-Dispase (Roche) and 10 µM HEPES (Invitrogen, Carlsbad, Calif.). Brain tissues are dispersed with a glass dounce homogenizer (Fisher), mixed for 15 min at RT, centrifuged (7 min, 1500 rpm), washed, and resuspended in 70% isotonic Percoll (Amersham, Piscataway, N.J.). Four ml of the cell suspension is transferred to 15 ml polypropylene conical tubes with equal volumes of 37% isotonic Percoll, 30% Percoll and 2 ml of HBSS sequentially layered on top, before centrifugation (40 min, 1200 rpm, 18° C.). The 70%: 37% Percoll interphase is collected and cells washed. Microglia are then resuspended at $1 \times 10^6$ cells/ml in RPMI media containing 10% calf serum, 0.05 µg/ml gentamycin, 1× nonessential amino acids, and 2 mM L-glutamine, and cultured in 25 $cm^2$ flasks for 48 h before preparation of CM.

Immune Modulators

We anticipate that factors produced by encephalitogenic T cells, by astroglia and by microglia will all modulate the generation of OPCs from the βT4 population in secondary neurospheres, although in different fashion for different cell preparations. We and our colleagues have extensive experience analyzing and purifying cytokines from such CM preparations, so that identification of the factors responsible for regulating βT4 cells will be feasible, primarily by identifying likely candidates for specific responses of βT4 cells and conducting blockade experiments using neutralizing antibodies. Encephalitogenic T cells will make inflammatory cytokines such as IFN-γ, IL-2 and IL-10, but may also make neurotrophins, as recently reported. Microglia express a different set of neurotrophins and cytokines, as do astrocytes. The principle advantage of these CM experim-ents will be to correlate the results from these simplified systems with the outcomes of analyzing SVZ extracts from EAE mice, so that the cells and factors responsible for effects in vivo can be identified.

Example 9

Characterization of the Distribution of βT4 and Transit Amplifying Cells in Developing Human Brain The human brain undergoes a protracted period of gliogenesis between 18 weeks postconception and the first postnatal year, which corresponds to the "second wave" of telencephalic gliogenesis in the rodent (E18 to P14). In this experiment, we take advantage of this aspect of human development to characterize the temporal and spatial distribution and the immunophenotype of βT4 cells in brain regions where MS lesions occur in adulthood. Our experimental approach focuses upon answering the two major questions described below.

Distribution of βT4 Cells in the Developing Human Telencephalon

We propose that the abundance of fetal SVZ βT4 cells changes in a region specific manner to meet the demands of local gliogenesis; the density of SVZ βT4 cells then stabilizes with brain maturation during the first two years of life and remains quiescent until activated by pathological conditions such as demyelination. The distribution of βT4 cells is determined in four brain regions at different developmental ages: (1) SVZ overlying the caudate nucleus which represents the largest expansion of the SVZ ("germinal matrix") equivalent to the dorso-lateral SVZ of the rodent; (2) SVZ of corpus callosum and septum in the same sections; (3) SVZ of frontal horns of the lateral ventricle; and (4) SVZ of occipital horns of the lateral ventricle. Our preliminary studies indicate that βT4 cell density in these SVZ regions varies extensively during fetal brain development (FIG. 7). Characterization of several ventricular regions is of value for two reasons. First, since myelination in the telencephalon shows a temporal progression, a correlation of the prenatal sequence of βT4 cell appearance with the postnatal sequence of myelination would support the idea that βT4 cells play a role in an early phase of oligodendrocyte lineage. And second, the periventricular lesions are common in MS and all ventricular regions are involved.

Several developmental ages are examined: 18-22 weeks post conception (wpc); 26-30 wpc; 36-40 wpc (term pregnancy); and postnatal up to two years of age (pc age=2 years+ 38 weeks). These developmental ages show increasing degrees of maturation by routine histology. Age 18-22 wpc is a period characterized by a thick non-layered cortical plate composed of "neuroblasts" with no evidence of cytologic differentiation. Between 26 and 30 weeks, the SVZ of the caudate nucleus decreases in thickness, cortical layers become apparent and neuronal cell bodies become separated from each other by increased neuropil and begin to display a pyramidal morphology. During this period, the white matter and cortex is increasingly populated by oligodendrocyte lineage cells and a subset starts to express markers of premyelinating oligodendrocytes. Myelination rapidly increases at 36-40 weeks and continues through the first two years of life. We expect that in any SVZ region, the total number of βT4 cells in the SVZ will increase to a peak followed by a stabilization or decrease. We also predict that the peak in βT4 cells will occur prior to the time that premyelinating oligodendrocytes, as demonstrated by proteolipid protein immunohistochemistry, peak in overlying parenchyma.

Phenotype of Transit Amplifying Cells in βT4-Enriched SVZ Regions

Previous literature on the stem cell niche in the rodent SVZ indicates that stem cells, transit amplifying cells and committed progenitor cells share a close spatial relationship. We investigate the possible role of βT4 cells in the context of the immunophenotype of transit amplifying and committed progenitor cells that are found in βT4-enriched SVZs in humans. While the rodent studies define the potential of βT4 cells in different growth factor environments, it is only through a characterization of the phenotype and spatial relationships in humans in vivo that we can demonstrate the relevance of the in vitro studies to human brain. Characterization of βT4 and neighboring cells in the human brain is particularly informative because the relevant brain regions are larger and the developmental time period more protracted than in rodents. In addition, the long term goal of our work is to understand the pathogenesis of MS, a disease unique to humans.

βIV tubulin, transcription factors and markers specific for progenitor cells are co-localized in this experiment. We test whether the βT4 cells or their neighbors express the transcription factors that secondary rat neurospheres do. Studied transcription factors include Mash1, Dlx2, Olig1, Olig2, and Nkx2.2. Specific lineage-associated markers for progenitor cells are also examined. These include NG2 and PDGFRα for oligodendrocytes, GFAP and zebrin II/aldolase C for astrocytes, and β-III tubulin and NeuN for neurons. βT4 cells do not appear to co-express markers specific for committed progenitors. It is possible however that some transit amplifying cells will express markers of committed progenitor cells.

Example 10

Characterization of the Distribution and Density of βT4 Cells in Adult Human Brain and MS Lesions In this experiment we examine the properties of βT4 cells in periventricular MS lesions. Current evidence on lineage determination in the central nervous system indicates that lineage committed progenitors, such as OPCs, may have limited proliferation capacity. Prior findings show that NG2-positive OPC are decreased in density in chronically demyelinated MS lesions. For this reason it is important to identify a cell at an earlier stage of differentiation that has a greater capacity of self-renewal. Therapeutic interventions to increase the capacity for MS lesions to remyelinate have the potential for reducing the progressive disability endured by patients with MS.

There is accumulating evidence that adult human SVZ stem cells exist and are capable of producing neurons, oligodendrocytes and astrocytes in vitro, and animal data indicate that such cells can be activated by the local environment. Our preliminary data suggests that the SVZ increases in size bordering MS lesions and that βT4 cells increase in number. We hypothesize that βT4 cells are increased adjacent to MS lesions.

Distribution and Density of βT4 Cells in the SVZ of the MS Brain

If the βT4 cells in the SVZ MS lesions play a role in lesion repair, we predict that the SVZ in this region would be expanded and that more βT4 cells would be present. To test this hypothesis, the number of βT4 cells in periventricular MS lesions is compared with adjacent non-lesion areas and corresponding regions in age-matched control brains. This comparison provides a detailed description of the normal adult distribution of βT4 cells in the course of testing the hypothesis that βT4 cells are increased in MS lesions. The SVZ βT4 cells have been identified in virtually all MS lesions we have examined thus far (23 lesions from six patients) and preliminary data indicate that there is increased βT4 cell number and an expanded SVZ. The total number of βT4 cells per defined length of ventricular wall are first determined, and the precise anatomic locations of each MS lesion examined are then compared to the same area in aged matched control brains.

Transit Amplifying Cells be Identified in the SVZ of MS Lesions

The width of the SVZ is dramatically increased in periventricular MS lesions. This implies activation of SVZ cells that may be involved in generation of new cells. This is supported by the increase in βT4 cells that we have identified in these areas. The purpose of these studies is to determine if transit amplifying cells can be identified in the SVZ that borders periventricular MS lesions. A paradigm similar to that in Example 7, which includes colocalization of βIV tubulin, transcription factors and committed progenitor cell antigens, is used.

Several studies have explored the expression of transcription factors associated with oligodendrocyte production in experimental models of demyelination, but to date few studies have characterized SVZ cells in MS brains. For example, Olig1, Olig2 and Nkx2.2 expression were increased within demyelinating lesions, and some of these cells also expressed markers of oligodendrocyte progenitor cells. Olig1 knockout mice, which develop normally, show marked reduction in remyelination, indicating that oligodendrocyte lineage-associated transcription factors may have different functions in development and disease. Our preliminary data demonstrate that SVZ βT4 cells are increased near periventricular MS plaques and that these cells also express Olig2. These observations are confirmed and extended by quantifying cells that express other transcription factors (as described).

Distribution of βT4 Cells in MS Lesions Correlate with Lesion Activity and with Clinical Features of the Patient The approach in this experiment is to correlate data obtained from the phenotyping analysis described above with histologic classification of the lesions, performed during the initial characterization of all lesions examined (described in Materials and Methods, below) and the clinical parameters obtained from the MS patient database. We question whether βT4 cells show relative resistance during different stages of lesion progression by examining the abundance of βT4 cells in acute, chronic active and chronic lesions. We previously showed that OPCs are decreased in lesions of patients with long disease duration. In this experiment, we ask whether duration of disease or patient age correlates with the number of βT4 cells in chronic lesions.

Materials and Methods

Tissue Specimens for Development Studies

All specimens are from autopsies of live-born infants performed at the Cleveland Clinic Foundation or Akron Children's Hospital. Cases with history or gross or microscopic evidence of primary neurologic disease are excluded. Post-conception age is based upon clinical history. Specimens are collected prospectively and one cerebral hemisphere sliced in the coronal plane and fixed for a maximum of two days in 4% paraformaldehyde. Our existing collection consists of tissues from 19 infants and includes several specimens each from post conception ages 18-22, 26-30 and 36-40 weeks and one specimen each from postnatal term pregnancies with death at ages two, three and 17 months. Post mortem intervals are known for half of the cases and range from 12-29 hours.

MS Tissue

All MS brains are obtained by a rapid procurement protocol established at the CCF Mellen Center for Multiple Sclerosis Treatment and Research in 1997 and supported by P01 NS 38667, "Tissue Injury and Inflammation in MS" since 1999. Patients at risk for death and their families are informed about an advanced directive to donate brain and spinal cord tissue for research purposes (CCF IRB 2076). We have received 142 advanced directives and procured tissue from 39 MS patients thus far. Clinical features of the consenting patients are stored in a secure database. Of the 17 MS brains procured in the last three years, 11 were from females, age ranged from 45-79 years, disease duration from 9-51 years, and EDSS from 6-9.5. Fifteen had secondary progressive MS and two had primary progressive MS.

The MS tissue procurement protocol includes post mortem MRI and rapid preservation of hemispheric coronal sections and longitudinal segments of spinal cord by fixation in 4% paraformaldehyde or freezing. The average time from death to tissue preservation is less than 5 hours. MS lesions are identified macroscopically (and with the aid of the postmortem MRI) and processed for free-floating section immunohistochemistry. Plaque activity is classified by immunostain for myelin basic protein and MHC Class II.

Adult Control Tissue

The control tissues for the studies are obtained from redundant/residual material from complete autopsies of patients without neurologic disease performed at the Cleveland Clinic Foundation. Control tissues are procured by the same protocol as described above with the exception of post mortem MRI (CCF IRB 5102). In the past 4 years, we have procured control tissues from nine autopsies. Control brains are from four females and five males ranging in age from 47-77 years. Post mortem time ranged from 7-30 hours (median=12 hours). Causes of death were myocardial infarction or other cardiac arrest (n=5), respiratory failure, disseminated intravascular coagulation, multiorgan thrombosis, and mesenteric hemorrhage.

Immunohistochemistry

Immunohistochemistry is performed on paraformaldehyde-fixed free floating sections or formalin fixed paraffin embedded sections by methods established in the laboratory. We possess the majority of the antibodies proposed for use in these studies and have validated their performance. Antibodies for transcription factors, Olig1, Olig2, Dlx2, Mash1 and Nkx2.2 are available from commercial sources, are suitable for immunohistochemistry. All characterization of antigen distribution will be first performed using immunoperoxidase-DAB detection and bright field microscopy. Double immunofluorescence will be evaluated by confocal microscopy.

Data Analysis

All immunostains are interpreted in view of the histology seen by hematoxylin and eosin stain of a representative section from the tissue block. The histologic features are used to orient the specimen and define the coronal level of specific anatomic structures (e.g., caudate nucleus, septum, thalamus) in order to provide a basis of comparison between different samples. All results are recorded in the context of the relationship of the SVZ to adjacent anatomic structures.

For each region examined, βT4 cells are counted in a defined length parallel to the ventricle of representative areas of SVZ. Because the thickness of the SVZ varies dramatically during development and also appears to increase in thickness in the MS lesions, the thickness of the SVZ is recorded. The density of βT4 cells is expressed per unit SVZ length and per unit SVZ area. Similarly, since the size of the SVZ regions increase in total length during development, the total number of βT4 cells per region is also recorded. Quantitative analyses may be performed on both paraffin sections (10 microns) and free-floating sections (30 microns). When comparisons between these two types of sections are necessary, the data is normalized based upon nuclear density. In addition to immunocytochemistry, we routinely perform in situ hybridization on human brain sections. If antibodies are unavailable or fail to stain, we will localize mRNA as an alternative method to verify gene expression.

Example 11

A Stem Source for Myelination in the Adult Brain

A major goal of central nervous system (CNS) stem cell research is to provide a means for cell replacement in neurodegenerative diseases. The best documented example of central nervous system cell replacement and repair in adult human brain is the generation of new oligodendrocytes in lesions of multiple sclerosis (MS). We and others have demonstrated the presence of oligodendrocyte progenitor cells in the lesions of MS and have correlated this with the generation of new oligodendrocytes. Committed progenitor cells have a limited capacity for division prior to differentiation. While adult stem cells have slow rates of division, they are capable of both extended self renewal and production of transient amplifying cells which produce significant numbers of new progenitor cells. Therapeutic stimulation of stem cells, therefore, has greater potential for promoting endogenous oligodendrocyte production and remyelination over the lifespan of a patient with MS.

Gliogenesis and neurogenesis continually occur throughout adult life. It has been shown that multipotent stem cells can be isolated from adult brain, including from the subventricular zone (SVZ). One well-characterized population of neural stem cells is found in the SVZ, expresses glial fibrillary acidic protein (GFAP) and can generate multipotent neurospheres in vitro. While the GFAP-positive cell has been extensively studied, this population does not account for all neural precursor cells in the SVZ. Including the GFAP-positive cell, recent studies have demonstrated that oligodendrocyte precursor cells (OPCs) are derived from multiple origins in the developing brain. Additionally, neural stem cell proliferation is influenced by sonic hedgehog signaling and Shh has been shown to differentially affect some populations of cells as it acts as a mitogen in OPCs, but not neuronal progenitors. These multiple sources and fates of multipotent neural cells support the conclusion that the mammalian central nervous system may harbor several populations of stem cells with regionally and functionally specific potentials.

Because stem cells are defined by their potential, their characterization depends upon experimental manipulation, either in vitro or in vivo. Such manipulations have demonstrated that the relatively quiescent stem cells are able to produce large numbers of differentiated progeny (committed progenitor cells) via a rapidly proliferating intermediate called a transient amplifying cell. The most widely used model for studying neuroectodermal stem cells is the neurosphere assay, in which dissociated CNS cells are grown in suspension cultures in the presence of epidermal growth factor (EGF) and fibroblast growth factor-2 (FGF2). It was originally thought that stem cells formed cell aggregates (neurospheres) which produced differentiated CNS cells following plating in the same culture medium. It has been recently demonstrated that transient amplifying cells and committed progenitor cells can also produce neurospheres. It is impossible to conclude, therefore, whether stem, transient amplifying or committed progenitor cells are the original source of the differentiated neural cells produced by neurospheres. Development of an assay system that incorporates a selection process to enrich the stem cell population would represent a major advance in this area.

We have identified a population of cells within the SVZ of the adult human brain that are defined by expression of β4 tubulin. We report here that these cells appear during human prenatal development, persist within the normal adult SVZ and are increased adjacent to demyelinated lesions in MS brains. β4 tubulin-positive cells are present in neurospheres derived from the perinatal rat and can be enriched to 95% homogeneity under growth limiting conditions. Sonic hedgehog, a known mitogen for adult CNS stem cell, drives the division of βT4 cells. When βT4 cell-enriched neurospheres are induced to differentiate in vitro, they produce oligodendrocytes, neurons, and astrocytes and produce myelinating oligodendrocytes when transplanted into the myelin deficient (md) rat. Taken together, these studies document the existence of a previously undescribed cell with properties of a neuroectodermal stem cell.

Results

βIV Tubulin-Positive Cells in the Human SVZ

Figure 17:
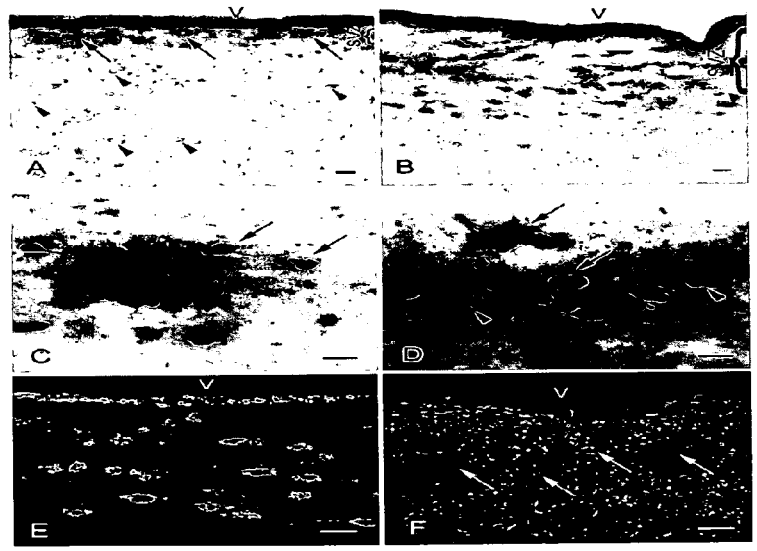
FIG. 17 illustrates antibodies to βIV tubulin identify a population of undifferentiated cells within the adult human subventricular zone (SVZ). In SVZ of both control (A) and MS (B) brains, βIV tubulin antibody detects immature appearing cells (arrows). Weaker βIV tubulin staining is also found on oligodendrocytes in myelinated white matter (A, arrowheads). Note that the SVZ in MS lesions (B) is wider than the SVZ of control brain (A). Some SVZ βT4 cells have a bipolar morphology with oval cell bodies (C, arrows); other βT4 cells have round cell bodies with several fine processes. βT4 cells tend to appear in clusters (D, arrows) or doublets (D, arrowheads). Confocal micrographs of a periventricular MS lesion show that βT4 cells express the transcription factor Olig2 (E) and do not express GFAP (F). V=lateral ventricle. Scale bars: 20 μm.

Our recent discovery that oligodendrocytes express beta IV tubulin in the rodent brain led us to investigate the utility of βIV tubulin antibodies to identify oligodendrocytes in CNS tissues from multiple sclerosis patients. In addition to oligodendrocytes, beta IV tubulin antibodies stained a population of undifferentiated cells within the adult human subventricular zone (SVZ) (FIG. 17). These cells, which we will refer to as βT4 cells, often appear as doublets or in small clusters, have sparse perinuclear cytoplasm and several thin processes (FIG. 17C, arrows). The SVZ βT4 cells are morphologically and geographically distinct from white matter oligodendrocytes, which are stained less intensely by NV tubulin antibodies (FIG. 17C, arrowheads). A possible association between βT4 cells and cells of the oligodendrocyte lineage is suggested by co-expression of the transcription factor, Olig2 (FIG. 17G); however, the sulfated proteoglycan, NG2, and proteolipid protein (PLP), which identify oligodendrocyte progenitor cells and premyelinating oligodendrocytes, respectively, were not detected in the βT4 cells in the SVZ (data not shown). βT4 cells did not express markers specific for microglia, astrocytes or neurons (data not shown). We investigated the possibility that βT4 is expressed by previously characterized cells that reside in the SVZ. GFAP (FIG. 17H) and PSA-NCAM markers associated with neuroectodermal stem cells and neuronal progenitor cells, respectively, were not detected in βT4 cells. Beta IV tubulin immunoreactivity was also detected in ependymal cells (FIGS. 17A,B) consistent with previous observations of this tubulin isoform in ciliated cells.

βT4 cells were detected in all lateral ventricular SVZ areas examined. The average number of βT4 cells in the SVZ of individuals without neurologic disease (14 randomly selected periventricular sections from four brains) was 4.8 cells/mm length of SVZ (Table 3). This number was not significantly different from normal appearing white matter adjacent to MS lesions (3.0 cells/mm, 10 sections from six patients). By contrast, the mean number of βT4 cells in MS lesions was 23 cells/mm SVZ. This increase was due both to an increase in number of doublets and clusters of βT4 cells in MS lesions and also in the width of the SVZ in these areas (FIG. 17B). These data support the concept that βT4 cells represent a dynamic cell population in the adult SVZ that can expand in response to demyelination in the adult human brain.

TABLE 3

|  | # of Pts | # sections | Cells/mm/patient (Mean ± SD) |
|---|---|---|---|
| Lesion SVZ | 8 | 20 | 23.0 ± 8.5*, # |
| SVZ adjacent to lesion | 6 | 10 | 3.0 ± 3.3 |
| Control SVZ | 4 | 14 | 4.8 ± 4.3 |

Figure 18:
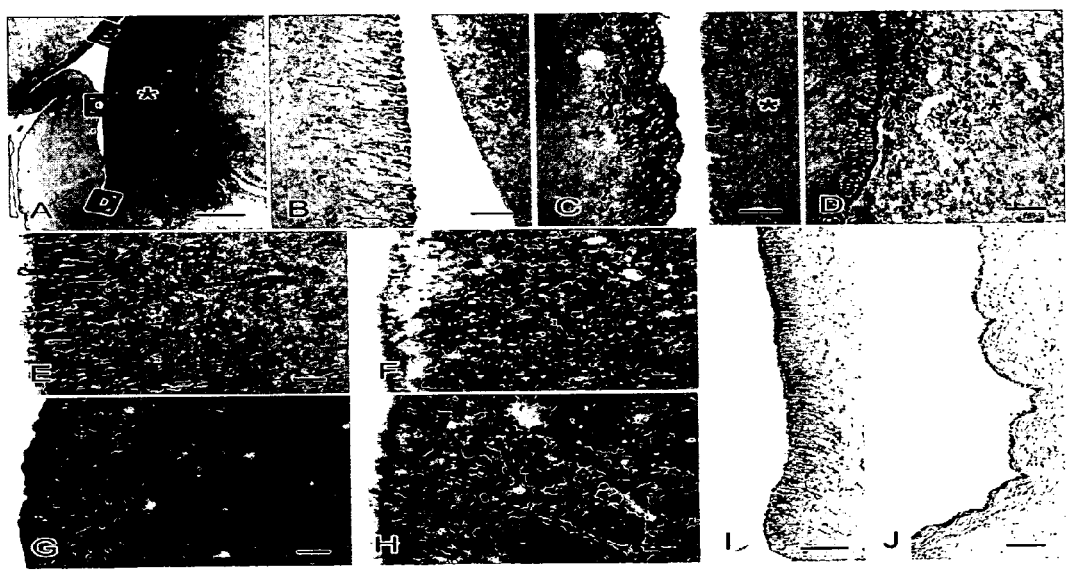
FIG. 18 illustrates βT4 cells show a dynamic spatial and temporal distribution in the developing telencephalon. Hematoxylin and eosin stained section of cerebrum surrounding lateral ventricle at 19 weeks post conception (A). Right is lateral, up is superior. The cellular area (* in A) is the expansion of the SVZ overlying the caudate nucleus that is normally present at this developmental age. Boxes in A identify the regions shown in panels B-D. βT4 cells are rare in the superior aspects of the lateral ventricular wall (* in B and C), but more frequent in the inferior aspect (* in D). They are more frequent in the subcallosal and septal walls than the lateral wall. The number of βT4 cells in the lateral wall increases during development. Panels E and G show SVZ regions corresponding to those shown in panels B and C, but from a brain at 28 wpc. The lateral SVZ is highly populated with βT4 cells. The distribution of βT4 cells is distinct from cells that label with antibodies to PSA-NCAM (F, H, sections adjacent to E, G, respectively). At 28 wpc, βT4 cells line all parts of the lateral ventricle, including the lateral angle (I). At 17 month post natal, βT4 cells throughout the lateral ventricle have a morphology and distribution similar to adults (J). Scale Bars: (A), 1 mm; (B-D), 50=μm; (E-H), 20 μm; (I,J), 100 p.m.

*Lesion SVZ vs. Control SVZ, unpaired two-tailed t-test, p = 0.0027 (or p < 0.005)
Lesion SVZ vs. SVZ adjacent to lesion, paired two-tailed t-test, p = 0.0003 (or p < 0.001).
Control SVZ vs. SVZ adjacent to lesion, unpaired two-tailed t-test, NS (p = 0.47).

βT4 Cells Show a Dynamic Spatial and Temporal Distribution in the Developing Telencephalon If βT4 cells represent a pre-progenitor cell related to oligodendrogenesis, it is reasonable to predict that these cells will have a predictable and dynamic distribution in the developing human brain. Generation of telencephalic glial progenitors occurs in several waves during mammalian brain development. An early wave originates from the medial ganglionic eminence and a latter wave originates from SVZ of the lateral ventricles. We investigated brain sections from immature liveborn infants who died at 19 and 28 weeks post-conception (wpc) and a 17 month old child to assess the distribution of βT4 cell during the latter stage of gliogenesis. FIG. 18A is an H&E stained section illustrating the histology of the brain surrounding the lateral ventricle at 19 wpc. Adjacent sections stained with antibodies to βT4 show that the distribution of βT4-positive cells is not uniform (FIG. 18B-D). βT4 cells are most numerous in inferior regions (FIG. 18D). Large numbers are also present on the medial (septal) and superior (callosal) sides of the ventricle (FIG. 18B,C). βT4 cells seem to arise in the ventricular zone but progressively take residence in the SVZ. βT4 cells are least abundant in the expanded SVZ (* in FIG. 18B,C) that overlies the caudate nucleus, but their numbers increase dramatically at 28 wpc (FIG. 18. E,G). Comparisons of the distribution of βT4 and PSA-NCAM positive cells indicate that these two cell types have distinct spatial distributions (FIG. 18E-H). Double label confocal microscopy confirmed that there was no evidence of overlap between βT4 cells and either PSA-NCAM or Tuj1 positive cells in the SVZ. Between 28 wpc and 17 month post natal, there is an increase in absolute number of βT4 cells as the ventricular surface expands, but the density of the cells does not change noticeably (FIG. 18 I,J). The overall density of βT4 cells in the section depicted in FIG. 8J is 9.3 cells/mm (23.5 mm length of SVZ counted). This density is slightly higher than that seen in adult controls.

βT4-Positive Cells are a Slowly Proliferating Multipotent Population of Cells in the Rodent Periventricular Forebrain.

To elucidate the possible function of βT4 cells, we investigated their phenotype in neurospheres generated from neonatal rat brain SVZ. Periventricular tissues from 4-day-old rat brain were dissociated and placed into a standard neurosphere culture medium containing EGF and FGF2, maintained for four days, plated onto coverslips and fixed in 4% paraformaldehyde. βT4-positive cells were present in approximately 20% of these primary neurospheres, where they represented the major cell type. Clues as to the possible role of βT4 cells in the SVZ came from BrdU labeling studies of primary neurosphere cells. Six hours after plating the neurospheres onto coverslips in the presence of BrdU, the majority of the cells in βT4-negative neurospheres were labeled, but the βT4-positive neurospheres contained few labeled cells (data not shown). Even after 20 hours in culture, the plated βT4-positive neurospheres remained relatively quiescent, but were surrounded by βT4-negative cells that showed rapid BrdU incorporation.

To extend these observations, we attempted to dissociate primary neurospheres prior to plating and observe their behavior in the absence or presence of the mitotic inhibitor, cytosine-β-D-arabinofuranoside (Ara-C). βT4-positive neurospheres were highly resistant to dissociation, whereas the other neurospheres were not. Relative resistance to disaggregation is a property commonly observed in cultures of pluripotent cells, such as embryonic stem cells and primordial germ cells. The "dissociated" cultures had growth properties similar to the plated primary neurospheres. Aggregates of βT4-positive cells were rapidly surrounded by βT4-negative cells. After 4 days in culture, only 0.03% of the cells were βT4 positive. In the presence of Ara-C, the number of βT4 positive cells increased to 83.2%. This represented a 2700 fold enrichment in βT4 cells. This enrichment persisted when Ara-C-treated cells were detached from the coverslips and put back into suspension culture in the presence of EGF and FGF2. After 4 days in suspension culture, greater than 95% of the neurospheres were βT4 positive. These observations support the idea that the βT4-positive neurospheres were composed of quiescent stem-like cells and not transient amplifying or committed progenitor cells, which also have the capacity to grow as aggregates in suspension culture.

We performed extensive immunophenotyping analyses on the βT4 cells in primary and secondary neurospheres. Immediately after plating, these cells showed robust staining with antibodies to Nkx2.1 and Olig2. Nkx2.1 is a transcription factor expressed by ancestors to the neurons and oligodendrocytes that arise from the medial ganglionic eminence. Olig2 is widely expressed by all stages of the oligodendrocyte lineage, but βT4-positive neurospheres did not express markers of committed oligodendrocyte progenitor cells or mature oligodendrocytes (data not shown). They also did not express markers of committed astrocytes, neurons, or microglial cells (data not shown). After 7-8 days in culture, however, O4-positive oligodendrocyte, GFAP-positive astrocytes and Tuj1-positive neurons differentiated from the βT4-positive secondary neurospheres. We investigated the possibility that βT4 is expressed by a previously characterized cell by testing over 30 other antibodies associated with stem and progenitor cells for double labeling with βT4-positive neurospheres, but have not obtained double labeling. These data support the interpretation the βT4-positive cells from the rodent perinatal SVZ represent a previously undescribed quiescent multipotent cell population.

Figure 19:
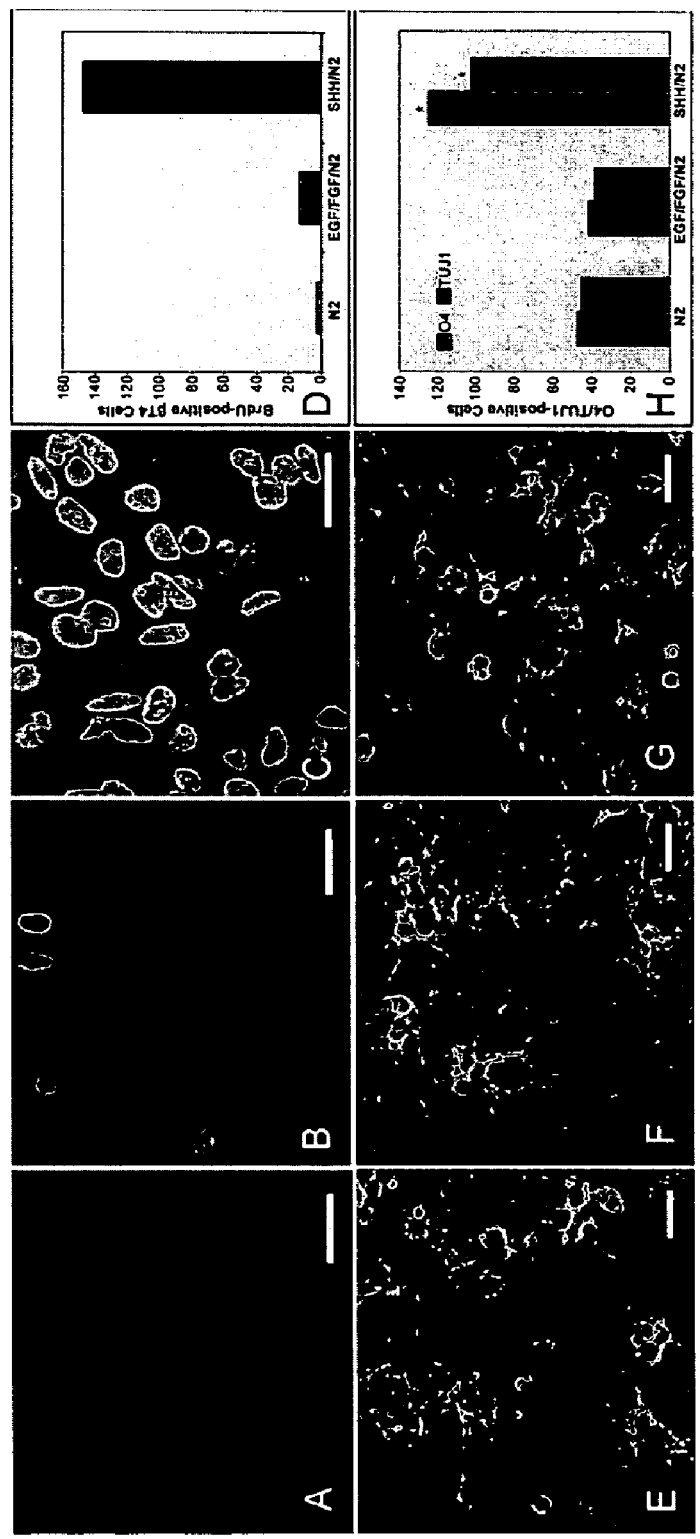
FIG. 19 illustrates sonic hedgehog (SHH) is a mitogen for βT4 cells. Secondary neurospheres were cultured in the presence of BrdU and either N2 (A), EGF/FGF2/N2 (neurosphere medium, B), or SHH/N2 (C) for 24 hours. The number of cells showing BrdU incorporation in the SHH-treated cultures was more than 7 times greater than that seen in the other media (D). The majority of the BrdU-positive cells were attached to the coverslip at the periphery of the plated neurospheres. When βT4-enriched secondary neurospheres were grown for 7 days in N2 (E), EGF/FGF2/N2 (F) or SHH/N2 (G), the number of O4-positive and Tuj1-positive cells varied. Secondary neurospheres cultured in SHH/N2 had over twice as many O4-positive oligodendrocytes and Tuj1-positive neurons than in either of the other media (H*, $p<0.001$). There was no significant difference in the numbers of O4- and Tuj1-positive cells in cultures grown in N2 or EGF/FGF2/N2 ($p>0.05$) Scale bars: (A-C,E-G), 20 μm.

Sonic Hedgehog Promotes Proliferation of βT4 Cells and Differentiation into Oligodendrocytes and Neurons If βT4 cells represent a CNS stem cell, growth factors should induce βT4 cell division and regulate the production of mature CNS cells. BrdU incorporation by secondary neurospheres in the presence of EGF/FGF2 (standard neurosphere medium) and sonic hedgehog (SHH), a proposed mitogen for stem cells in the SVZ of adult rat brain, was compared to neurospheres grown in the absence of these growth factors (serum-free medium containing N2 supplement). After 24 hours of culture in the presence of BrdU, neurospheres grown in N2 alone showed little evidence of proliferation (FIG. 19A). BrdU incorporation increased slightly in the presence of EGF and FGF2 (FIG. 19B), but dramatically in the presence of SHH (FIG. 19 C,D). Most of the BrdU-positive βT4 cells were present at the border of the secondary neurospheres and appeared to be migrating onto the surface of the coverslip (FIG. 19 C). We next determined if SHH had an effect on the generation of mature neural cells from βT4 cells. Secondary neurospheres were grown as described above for 7 days, and, while O4-positive oligodendrocytes, Tuj1-positive neurons (FIG. 19 E-G) and GFAP-positive astrocytes (not shown for all media) surrounded all neurospheres, their numbers varied extensively. Secondary neurospheres grown in SHH produced significantly more oligodendrocytes and neurons compared to the other media (FIG. 19H). We tested several concentrations of SHH and found that the effects on BrdU labeling and oligodendrocyte and neuron generation were optimal at 1000 ng/ml. Addition of PDGF-A, alone or in combination with SHH, had not effect on differentiation. These data support the hypothesis that SHH is a mitogen for βT4 cells and influences the generation of oligodendrocytes and neurons from βT4 cell-enriched secondary neurospheres.

Secondary Neurospheres Produce Oligodendrocytes In Vivo

Figure 20:
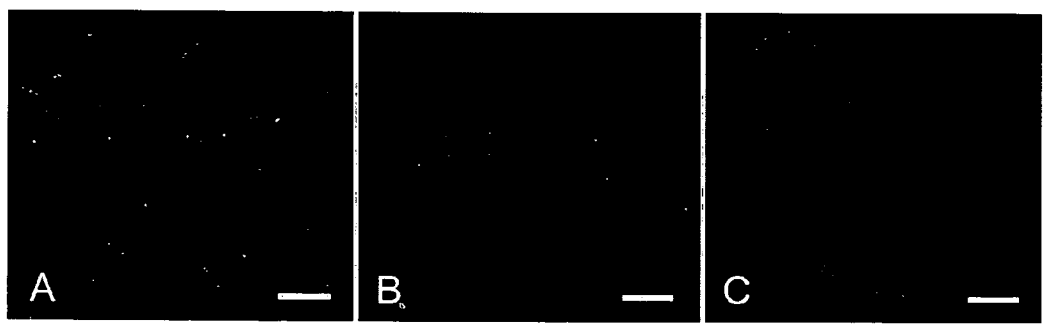
FIG. 20 illustrates secondary βT4 neurospheres differentiate into myelinating oligodendrocytes when transplanted into myelin deficient (md) rat brains. Secondary neurospheres were transplanted into the striatum of P3 pups, and brain sections were stained with antibodies to PLP 17 days later. Multiple foci of PLP-positive myelinating oligodendrocytes were seen in the corpus callosum (A), striatum (B), and cerebral cortex (C). Scale bar=20 μm.

To test the potential of βT4 cell-enriched secondary neurospheres to respond to in vivo cues and produce oligodendrocytes, we transplanted secondary neurospheres into the brains of myelin deficient (md) rats. The md rat has a mutation in the proteolipid (PLP) gene, severe hypomyelination and no detectable PLP surrounding axons. The presence of PLP immunoreactivity following transplantation, therefore, will reflect myelination by progeny of the secondary neurosphere cells. Forty neurospheres (~8,000 cells) were injected into the right striatum of 3 day-old md rat pups. Because of their limited lifespan, md pups were sacrificed at day 20 and examined for PLP-positive myelin sheaths. FIG. 20 illustrates PLP-positive myelin was found in striatum, corpus callosum and cerebral cortex. The myelinating cells were widely distributed on the injected side of the brain, but were not seen on the contralateral side. The transplanted oligodendrocytes often occurred in clusters with each extending several PLP-positive processes to individual myelin sheaths.

Discussion

Four major findings of this study support the concept that βT4 antibodies identify a stem cell in the mammalian brain. First, βT4 cells have a temporal and spatial distribution which correlates with the latter stage of telencephalic gliogenesis in the developing human brain. Second, βT4 cells were present at low densities in the SVZ of the lateral ventricles of the adult human brain and were increased 7-fold in the SVZ of MS lesions. Third, anti-mitotic treatment of rat brain primary neurospheres resulted in an 2.700-fold enrichment of βT4 cells. Fourth, generated by the enriched βT4-positive secondary neurospheres proliferated in response to SHH and produced oligodendrocytes, neurons and astrocytes in vitro and oligodendrocytes in vivo.

Our initial identification of SVZ βT4 cells was a result of testing whether βIV tubulin antibodies could identify oligodendrocytes in sections from MS brains. While βT4 antibodies weakly stained oligodendrocytes in adult human brain, an additional population of βT4 cells were present in the SVZ. Several observations suggested that these cells have stem cell characteristics. The most striking was the increase in βT4 cell doublets and density in the SVZ adjacent to lesions. This implied that these cells had the capacity to divide, albeit slowly because proliferation markers failed to label these cells and mitotic figures were not observed. The SVZ of MS lesions is a region where we consistently identify oligodendrocyte progenitor cells, but βT4 cells did not express specific markers of OPC or any other previously characterized CNS cells. On the other hand, BT4 cells expressed olig2, a transcription factor that is expressed by populations of undifferentiated neuroepithelial cells during development and throughout the oligodendrocyte lineage. For this reason, we investigated the origins of βT4 SVZ cells in the adult human CNS by analysis of the developing human brain.

Gliogenesis in the mammalian telencephalon occurs in a continuous wave that begins in embryonic ventral proliferative zones, such as the medial and lateral ganglionic eminences and progresses dorsally during the fetal and perinatal periods. The pattern of βT4 expression shows the same temporal and spatial distribution. The earliest age examined was 19 weeks post conception, which is developmentally roughly equivalent to the perinatal rodent. At this point βT4 cells were most numerous ventrally and progressively increased dorsally at later ages. In the postnatal brain the density is decreased to a level similar to the adult brain. The change in density could result from any combination of mechanisms, including cell death, differentiation and brain growth. The final result is a diffuse distribution of these cells throughout the SVZ of the lateral ventricles and positioned to be activated in response to demyelination of subventricular white matter of the adult brain.

While the distribution of βT4 cells support their association with gliogenesis in developing and diseased human brains, these correlations did not provide direct evidence for stem cell behavior. Therefore, we investigated rat βT4 cell behavior in vitro. By incorporating an arac selection step into the standard neurosphere assay, we were able to produce neurospheres that were nearly homogeneous for βT4 immunophenotype and differentiated into neurons, oligodendrocytes and astrocytes when placed into adherent cultures. These cells showed little evidence of proliferation in the presence of EGF and FGF2 but rapidly incorporated BrdU in response to Shh. In vivo fate mapping has shown that all lineages in adults can differentiate from Shh responsive cells. The most numerous derivatives of Shh responsive cells in this healthy rodent model were the neurons of the olfactory bulb and dentate gyrus that are constitutively produced throughout adulthood. Our transplantation studies demonstrating that myelinating oligodendrocytes are produced from βT4 cells and the apparent proliferation of βT4 cells in the lesions of MS suggest that βT4 cells in the adult SVZ can be activated to proliferate and differentiate in the setting of oligodendrocyte deficiency.

We were unable to identify any relationship of the βT4 cells described here to other SVZ cells with stem cell properties. The best characterized stem cell of the adult SVZ cell expresses GFAP. Although we have identified small numbers of GFAP positive cells in secondary βT4 enriched neurospheres, we have never observed co-expression of GFAP and βT4 in vivo or in vitro. It is possible that these antigens are expressed at different stages, and transgenic lineage tracing studies in progress will address this question. Regardless of the answer, this work has identified a model in vitro system for obtaining pure populations of a cell with stem cell properties and inducing rapid proliferation providing new avenues for investigation and development of therapeutics.

The potential of stem cell therapeutics to treat neurodegeneration disease will require better characterization of the adult stem cell in human brain. Adult CNS stem cell research has been limited by the lack of unambiguous markers and by the ability of transient amplifying and committed progenitor cells to produce neurospheres. We described here a SVZ cell in the human brain that has stem cell traits based upon a low rate of proliferation, adhesion upon enrichment, appropriate spatial, temporal and quantitative distributions in developing and diseased human brain, and the ability to produce differentiated neural cells in vitro and in vivo.

Materials and Methods
Tissue Specimens

Human subjects approvals. All human tissue studies were approved by the Cleveland Clinic Institutional Review Board.
Multiple Sclerosis Tissue All MS brains were obtained by a rapid post mortem procurement protocol from prospectively consented donors and characterized as previously described. A total of 20 lesions from 8 brains were examined in this study.
Adult Control Tissue The control tissues were obtained from redundant/residual material from complete autopsies of patients without neurologic disease performed at Cleveland Clinic. A total of 14 sections from 4 brains were examined.
Perinatal Control Tissue Development studies were performed on tissues from redundant/residual material from complete autopsies of live born infants performed at Cleveland Clinic (n=1, full term birth, post natal 17 months, cause of death: acute myocardial infarction secondary to congenital heart disease) or Akron Children's Hospital (n=12, ages 19-38 weeks post conception, other demographics unknown). Representative sections including the SVZ were available for examination.
Immunohistochemistry of Tissue Sections
Antibodies Tissue sections were immunostained with antibodies specific for the following molecules: Class III beta tubulin (Tuj1), Covance; Class IV beta tubulin, Sigma; GFAP, Dako, Glostrup, Denmark; Leukocyte common antigen (LCA), Dako, Glostrup, Denmark; MHC Class II (HLA-DP, DQ, DR Antigen), Dako, Glostrup, Denmark; Myelin basic protein (MBP), Sternberger Monoclonals, Baltimore, Md.; Ng2 Chondroitin Sulfate Proteoglycan (NG2), Chemicon International, Olig2, Gift from David Rowitch, John Alberta; Proteolipid protein (PLP), (Agmed, Bedford, Mass.); PSA-NCAM, Pharmingen, San Diego, Calif.

Procedure

Immunohistochemistry of tissue was performed on paraformaldehyde-fixed free floating sections (all adult specimens) or formalin fixed paraffin embedded sections (perinatal specimens) by methods established in the laboratory. Antigen retrieval was used when necessary. All characterization of antigen distribution in tissue was first performed using avidin biotin complex (Vector) and diaminobenzidine histochemistry and brightfield microscopy. Sections used for double-labeling experiments were incubated with two primary antibodies for 3-5 days followed by fluorescently-conjugated and biotinylated secondary antibodies (Jackson ImmunoResearch Laboratories, West Grove, Pa.) for 1-2 hours.
Quantitation of βT4 cells in SVZ The SVZ was defined as the region between the ependyma and subcortical white matter defined by axon and myelin immunostaining. MS lesion areas were defined by PLP staining in adjacent sections. βT4 cells were counted in sequential 0.5 mm fields using a 40× objective. For statistical comparison of MS and control βT4 cells, all counts from each brain were combined and non-paired Student's t-tests were used with Bonferroni correction for multiple comparisons. Paired t-tests were used for comparison of βT4 cells in lesion versus non-lesion areas. Significance was set at $p<0.05$.
Cell Culture
Primary Neurosphere Culture All studies on animals were approved in advance by Cleveland Clinic Institutional Animal Care and Use Committee. Postnatal day four (P4) Sprague Dawley rats were anesthetized by hypothermia and the brains rapidly removed and dissected. Periventricular tissue was isolated from a ~1 mm thickness coronal section of forebrain at level of the septum. It included ependyma and subependymal tissue from the medial and lateral walls of the lateral ventricle, but excluded the superior wall that underlies the subcortical white matter. The tissue was finely minced and incubated in Trypsin (0.05%, Mediatech Cellgro, Herndon, Va.) and DNase (250 U/ml, Sigma, St. Louis, Mo.) at 37° C. for 10 minutes. Digestion was stopped with 10% fetal bovine serum (FBS, Hyclone, Logan, Utah). The suspension was filtered with a 40 μm cell strainer (Becton-Dickinson, Bedford, Mass.), washed and centrifuged. The pellet was suspended using "neurosphere medium" composed of DMEM/F12 (Fisher), N2 supplement (1%, Invitrogen, Carlsbad, Calif.), epidermal growth factor (EGF, 20 ng/ml, Sigma), basic fibroblast growth factor (FGF2, 20 ng/ml, Sigma), Glutamax (1%, Gibco, Invitrogen, Carlsbad, Calif.) and Penicillin-Streptomycin (1%, Cellgro). Approximately $15 \times 10^5$ cells were plated per uncoated T75 flask and grown at 37° C. and 5% $CO_2$. After 3-4 days in culture, primary neurospheres were either analyzed by immunocytochemistry or used to produce secondary neurospheres.
Secondary Neurosphere Culture Primary neurospheres, generated as described above, were dissociated with trypsin and trituration and then plated onto poly-L-lysine-coated (P-1274, Sigma) coverslips ($10^5$ cells/12 mm coverslip). The coverslips were incubated in neurosphere medium with cytoarabinoside-C (Ara-C, 10 μM, Sigma) for 4 days. Cells were detached from the coverslips by incubation on ice. Following centrifugation, cells were resuspended and placed into T25 flasks for 3-4 days. The neurospheres resulting from these procedures are defined as secondary neurospheres and were analyzed by immunocytochemistry as described above or induced to differentiate.

Neurosphere Differentiation

Undissociated secondary neurospheres were plated onto PLL-coated coverslips and analyzed at either 24 hours or 7 days in vitro with DMEM/F12, Glutamax and Penicillin-Streptomycin (1%, Cellgro) with different supplements as follows: N2 (1%); N2 (1%) plus sonic hedgehog (SHH, 1000 ng/ml, R&D, Minneapolis, Minn.); "neurosphere medium" (N2 (1%), EGF (20 ng/ml), FGF2, 20 ng/ml).

Immunocytochemistry of Cell Cultures

Antibodies

Neurospheres were routinely immunostained with antibodies specific for the following molecules: BrdU, AbCam Ltd., Cambridge, Mass.; Class III beta tubulin (Tuj1), R&D, Minneapolis, Minn.; Class IV beta tubulin, Sigma, St. Louis, Mo.; GFAP, Dako, Glostrup, Denmark; Ng2 Chondroitin sulfate proteoglycan (NG2), Chemicon International, Temecula, Calif.; O4, Gift from Robert Miller; Olig2, Gift from David Rowitch, John Alberta; Proteolipid protein (PLP), Agmed, Bedford, Mass.; PSA-NCAM, BD Biosciences Pharmingen; TTF-1 (Nkx2.1), Santa Cruz Biotechnology, Inc., Santa Cruz, Calif. Fluorescently labeled secondary antibodies used were: goat-anti-mouse IgM FITC 1:200 (ICN/CAPPEL); goat anti-mouse IgG Alexa 1:400 (Molecular Probes); goat anti rabbit IgG Alexa 1:200 (Molecular Probes); goat anti-rabbit IgG FITC 1:200 (ICN/CAPPEL); goat anti rat IgG FITC, 1:200 (Jackson Laboratory). Neurospheres were also immunophenotyped with an extensive panel of antibodies known to react with stem and progenitor cells.

Procedure

In some experiments, primary neurospheres plated on coverslips were exposed to BrdU (20 µM, Sigma) for the last 6, 16, 20 or 88 hours before fixation and staining, and secondary neurospheres exposed to BrdU (20 µM, Sigma) for 1 to 3 days in the flasks. For immunocytochemistry, neurospheres were transferred to poly-L-lysine-coated coverslips and allowed to attach for at least 15 min prior to fixation. Coverslips were fixed with 4% paraformaldehyde for 30 minutes and permeabilized and blocked with 10% goat normal serum in 0.1% triton-X100/PBS (1 hour). Primary antibodies were applied at room temperature, except for BrdU (see below). For BrdU immunocytochemistry, the coverslips were incubated in 2N HCl (1 hour) followed by sodium borate, pH 8.6 (30 min). FITC conjugated monoclonal anti-BrdU antibody (1:20) was applied overnight at 4° C. DAPI was included in the mounting medium (Vectashield) for nuclear detection.

Quantitation of βT4 cells in vitro

βT4 positive cell percentage in control and Ara-C-treated cultures were quantified by counting 10 randomly selected fields using standard fluorescence microscopy and a 20× objective. βT4 positive primary neurosphere and secondary neurosphere percentage were quantified by counting 10 randomly selected fields using a 10× objective. BrdU incorporation over a 24 hours period (FIG. 17D) was quantified in secondary neurospheres by counting the total number of BrdU-positive cells in 18 neurospheres using a 20× objective (three independent experiments). Quantitation of O4- and Tuj1-positive cell density at seven days in vitro in different media (FIG. 17H) were quantified in two independent culture experiments by counting 5 randomly selected fields using standard fluorescence microscopy and a 20× objective.

Secondary Neurosphere Transplantation

Male myelin deficient rats (md rats, Wistar background) were used for transplantation of secondary neurospheres. These rats have a point mutation at position 75 (exon 3) of the PLP gene on the X-chromosome. These rats show evidence of PLP expression but do not form myelin in the central nervous system. Pups die within 30 days after birth. P3 pups were anesthetized by hypothermia and subjected to stereotactic injection with 5 microliters of neurospheres suspended by trituration (approximately 40 neurospheres, 10,000 cells). Injection coordinates targeting the left corpus striatum were 0.4 mm anterior to Bregma, 2.3 mm lateral to midline, 3.0 mm deep. Rats were allowed to survive for 17 days followed by intracardiac perfusion with 4% paraformaldehyde. Coronal free-floating sections were taken and stained with antibodies to PLP.

Microscopy and Image Capture

Brightfield images were obtained using a Leica DMR microscope (W. Nuhsbaum Inc, McHenry Ill.) equipped with an Optronix Magnafire digital camera (Goleta, Ca) and processed using Photoshop software (Adobe Corp, CA). Double immunofluorescence was evaluated by confocal microscopy using a Leica TCS-NT microscope (Leica Microsystems, Exton Pa.), equipped with an x63 1.4 NA lens followed by image processing with Scion image (Scion Corp, Frederick, Md.) and preparation in Photoshop.

From the above description of the invention, those skilled in the art will perceive improvements, changes and modifications. Such improvements, changes and modifications within the skill of the art are intended to be covered by the appended claims.

Having described the invention, we claim:

1. A method for enriching a population of neural stem cells, the method comprising the steps of:
    obtaining a population of uncultured cells containing at least one neural stem cell expressing βT4 and Olig2, and not expressing NG2, PLP and GFAP;
    culturing the cells in a first neurosphere forming medium to promote formation of neurospheres;
    treating cell of the neurospheres formed in the first neurosphere forming assay with an agent that kill actively dividing cells.

2. The method of claim 1, the uncultured cells being obtained neural tissue of a mammal.

3. The method of claim 2, the neural tissue being obtained from the subventricular zone of the telencephalon of the mammal's brain.

4. The method of claim 3, the agent comprising an antimetabolic agent.

5. The method of claim 3, the agent comprising cytosine-β-D-arabinofuranoside (Ara-C).

6. The method of claim 1, further comprising culturing the neurospheres formed in the first neurosphere forming medium in a second neurosphere forming medium, the second neurosphere forming medium including an agent that kills actively dividing cells.

7. The method of claim 1, further comprising culturing the cells treated with the agent in a second neurosphere forming medium and promotes formation of neurospheres.

8. The method of claim 1, the first neurosphere forming medium including epidermal growth factor (EGF) and basic fibroblast growth factor 2(FGF2).

9. The method of claim 6, the second neurosphere forming medium including epidermal growth factor (EGF) and basic fibroblast growth factor 2 (FGF2).

* * * * *